US010973681B2

(12) United States Patent
Andino et al.

(10) Patent No.: US 10,973,681 B2
(45) Date of Patent: Apr. 13, 2021

(54) DEVICES AND METHODS FOR ADJUSTING THE INSERTION DEPTH OF A NEEDLE FOR MEDICAMENT DELIVERY

(71) Applicant: Clearside Biomedical, Inc., Alpharetta, GA (US)

(72) Inventors: Rafael V. Andino, Grayson, GA (US); Shelley Eckert Hancock, Atlanta, GA (US)

(73) Assignee: CLEARSIDE BIOMEDICAL, INC., Alpharetta, GA (US)

( * ) Notice: Subject to any disclaimer, the term of this patent is extended or adjusted under 35 U.S.C. 154(b) by 124 days.

(21) Appl. No.: 15/675,035

(22) Filed: Aug. 11, 2017

(65) Prior Publication Data
US 2018/0042767 A1 Feb. 15, 2018

Related U.S. Application Data

(60) Provisional application No. 62/374,300, filed on Aug. 12, 2016.

(51) Int. Cl.
*A61F 9/00* (2006.01)
*A61M 37/00* (2006.01)
*A61M 5/46* (2006.01)

(52) U.S. Cl.
CPC ....... *A61F 9/0017* (2013.01); *A61M 37/0015* (2013.01); *A61M 5/46* (2013.01);
(Continued)

(58) Field of Classification Search
CPC ...... A61M 37/0015; A61M 2037/0023; A61M 2037/0061; A61M 2210/0612; A61M 5/46; A61F 9/0017
See application file for complete search history.

(56) References Cited

U.S. PATENT DOCUMENTS 2,187,259 A 1/1940 Barnhart
2,841,145 A 7/1958 Epps
(Continued)

FOREIGN PATENT DOCUMENTS

CA 2639322 3/2009
CN 1229679 A 9/1999
(Continued)

OTHER PUBLICATIONS

Office Action for Indian Application No. 10099/DELNP/2012, dated Jul. 2, 2019, 5 pages.
(Continued)

*Primary Examiner* — Tiffany Legette
(74) *Attorney, Agent, or Firm* — Cooley LLP

(57) ABSTRACT

An apparatus includes a housing, an adjustment member, and a microneedle. The housing can be coupled to a medicament container, and includes a hub surface that can contact a target surface. The adjustment member is within the housing and separates an inner volume of the housing into a first chamber and a second chamber. The first chamber is fluidically coupled with the medicament container. The adjustment member, which is coupled to the microneedle, can transition between a first configuration and a second configuration. A proximal end portion of the microneedle is fluidically coupled to the first chamber such that a substance can be conveyed from the medicament container through the microneedle. A distal tip of the microneedle extends from the hub surface by a first distance when the adjustment member is in the first configuration, and by a second distance when the adjustment member is in the second configuration.

21 Claims, 17 Drawing Sheets

(52) U.S. Cl.
CPC .............. *A61M 2037/0023* (2013.01); *A61M 2037/0061* (2013.01); *A61M 2210/0612* (2013.01)

(56) References Cited

U.S. PATENT DOCUMENTS

| | | | |
|---|---|---|---|
| 2,939,459 A | 6/1960 | Lazarte et al. | |
| 3,376,999 A | 4/1968 | De Hart et al. | |
| 3,477,432 A | 11/1969 | Shaw | |
| 3,739,947 A | 6/1973 | Baumann et al. | |
| 3,762,540 A | 10/1973 | Baumann et al. | |
| 3,788,320 A | 1/1974 | Dye | |
| 3,838,690 A | 10/1974 | Friedman | |
| 3,892,311 A | 7/1975 | Sneider | |
| 3,962,430 A | 6/1976 | O'Neill | |
| 3,964,482 A | 6/1976 | Gerstel et al. | |
| 4,226,328 A | 10/1980 | Beddow | |
| 4,377,897 A | 3/1983 | Eichenbaum et al. | |
| 4,383,530 A | 5/1983 | Bruno | |
| 4,417,887 A | 11/1983 | Koshi | |
| 4,432,964 A | 2/1984 | Shell et al. | |
| 4,501,363 A | 2/1985 | Isbey, Jr. | |
| 4,525,346 A | 6/1985 | Stark | |
| 4,564,016 A | 1/1986 | Maurice et al. | |
| 4,601,708 A | 7/1986 | Jordan | |
| 4,615,331 A | 10/1986 | Kramann | |
| 4,689,040 A | 8/1987 | Thompson | |
| 4,708,147 A | 11/1987 | Haaga | |
| 4,717,383 A | 1/1988 | Phillips et al. | |
| 4,736,850 A | 4/1988 | Bowman et al. | |
| 4,755,169 A | 7/1988 | Sarnoff et al. | |
| 4,795,432 A | 1/1989 | Karczmer | |
| 4,804,371 A | 2/1989 | Vaillancourt | |
| 4,826,490 A | 5/1989 | Byrne et al. | |
| 4,826,871 A | 5/1989 | Gressel et al. | |
| 4,889,529 A | 12/1989 | Haindl | |
| 4,941,874 A | 7/1990 | Sandow et al. | |
| 4,966,773 A | 10/1990 | Gressel et al. | |
| 5,015,240 A | 5/1991 | Soproni et al. | |
| 5,023,087 A | 6/1991 | Yau-Young | |
| 5,024,662 A | 6/1991 | Menes et al. | |
| 5,057,072 A | 10/1991 | Phipps | |
| 5,066,276 A | 11/1991 | Wang | |
| 5,098,389 A | 3/1992 | Cappucci | |
| 5,137,447 A | 8/1992 | Hunter | |
| 5,164,188 A | 11/1992 | Wong | |
| 5,172,807 A | 12/1992 | Dragan et al. | |
| 5,181,909 A | 1/1993 | McFarlane | |
| 5,206,267 A | 4/1993 | Shulman | |
| 5,273,530 A | 12/1993 | del Cerro et al. | |
| 5,279,564 A | 1/1994 | Taylor | |
| 5,295,972 A | 3/1994 | Mischenko | |
| 5,300,084 A | 4/1994 | Johnson | |
| 5,312,361 A | 5/1994 | Zadini et al. | |
| 5,320,609 A | 6/1994 | Haber et al. | |
| 5,354,286 A | 10/1994 | Mesa et al. | |
| 5,358,489 A | 10/1994 | Wyrick | |
| 5,364,373 A | 11/1994 | Waskonig et al. | |
| 5,364,374 A | 11/1994 | Morrison et al. | |
| 5,364,734 A | 11/1994 | Morrison et al. | |
| 5,395,310 A | 3/1995 | Untereker et al. | |
| 5,397,313 A | 3/1995 | Gross | |
| 5,399,159 A | 3/1995 | Chin et al. | |
| 5,407,070 A | 4/1995 | Bascos et al. | |
| 5,409,457 A | 4/1995 | del Cerro et al. | |
| 5,443,505 A | 8/1995 | Wong et al. | |
| 5,538,503 A | 7/1996 | Henley et al. | |
| 5,547,467 A | 8/1996 | Pliquett et al. | |
| 5,575,780 A | 11/1996 | Saito | |
| 5,632,740 A | 5/1997 | Koch et al. | |
| 5,658,256 A | 8/1997 | Shields | |
| D383,049 S | 9/1997 | Concari et al. | |
| 5,667,491 A | 9/1997 | Pliquett et al. | |
| 5,681,825 A | 10/1997 | Lindqvist et al. | |
| 5,752,942 A | 5/1998 | Doyle et al. | |
| 5,766,198 A | 6/1998 | Li | |
| 5,766,242 A | 6/1998 | Wong et al. | |
| 5,767,079 A | 6/1998 | Glaser et al. | |
| 5,779,668 A | 7/1998 | Grabenkort | |
| 5,788,679 A | 8/1998 | Gravlee, Jr. | |
| 5,792,099 A | 8/1998 | DeCamp et al. | |
| 5,817,075 A | 10/1998 | Giungo | |
| 5,824,072 A | 10/1998 | Wong | |
| 5,911,223 A | 6/1999 | Weaver et al. | |
| 5,919,158 A | 7/1999 | Saperstein et al. | |
| 5,952,378 A | 9/1999 | Stjernschantz et al. | |
| 5,968,022 A | 10/1999 | Saito | |
| 6,059,111 A | 5/2000 | Davila et al. | |
| 6,083,199 A | 7/2000 | Thorley et al. | |
| 6,143,329 A | 11/2000 | Kim | |
| 6,159,218 A | 12/2000 | Aramant et al. | |
| 6,280,470 B1 | 8/2001 | Peyman | |
| 6,299,603 B1 | 10/2001 | Hecker et al. | |
| 6,309,347 B1 | 10/2001 | Takahashi et al. | |
| 6,309,374 B1 | 10/2001 | Hecker et al. | |
| 6,319,225 B1 | 11/2001 | Sugita et al. | |
| 6,319,240 B1 | 11/2001 | Beck | |
| 6,334,856 B1 | 1/2002 | Allen et al. | |
| 6,378,526 B1 | 4/2002 | Bowman et al. | |
| 6,387,078 B1 | 5/2002 | Gillespie, III | |
| 6,397,849 B1 | 6/2002 | Bowman et al. | |
| 6,413,245 B1 | 7/2002 | Yaacobi et al. | |
| 6,432,090 B1 | 8/2002 | Brunel | |
| 6,494,865 B1 | 12/2002 | Alchas | |
| 6,503,231 B1 | 1/2003 | Prausnitz et al. | |
| 6,517,523 B1 | 2/2003 | Kaneko et al. | |
| 6,524,581 B1 | 2/2003 | Adamis | |
| 6,530,904 B1 | 3/2003 | Edwards et al. | |
| 6,540,725 B1 | 4/2003 | Ponzi | |
| 6,551,299 B2 | 4/2003 | Miyoshi et al. | |
| 6,558,361 B1 | 5/2003 | Yeshurun | |
| 6,564,630 B1 | 5/2003 | Klemp | |
| 6,569,123 B2 | 5/2003 | Alchas et al. | |
| 6,611,707 B1 | 8/2003 | Prausnitz et al. | |
| 6,622,864 B1 | 9/2003 | Debbs et al. | |
| 6,738,526 B1 | 5/2004 | Betrisey et al. | |
| 6,743,211 B1 | 6/2004 | Prausnitz et al. | |
| 6,773,916 B1 | 8/2004 | Thiel et al. | |
| D499,153 S | 11/2004 | Kuo | |
| 6,883,222 B2 | 4/2005 | Landau | |
| 6,918,889 B1 | 7/2005 | Brunel | |
| 6,929,623 B2 | 8/2005 | Stone | |
| 6,936,053 B1 | 8/2005 | Weiss | |
| 6,979,316 B1 | 12/2005 | Rubin et al. | |
| 7,025,774 B2 | 4/2006 | Freeman et al. | |
| 7,150,735 B2 | 12/2006 | Hickle | |
| 7,207,965 B2 | 4/2007 | Simon | |
| 7,207,980 B2 | 4/2007 | Christian et al. | |
| 7,211,062 B2 | 5/2007 | Kwon | |
| 7,214,212 B2 | 5/2007 | Pommereau et al. | |
| 7,226,439 B2 | 6/2007 | Prausnitz et al. | |
| 7,316,676 B2 | 1/2008 | Peyman et al. | |
| 7,425,207 B2 | 9/2008 | Miller et al. | |
| 7,435,237 B2 | 10/2008 | Tan | |
| 7,468,057 B2 | 12/2008 | Ponzi | |
| D590,690 S | 4/2009 | Bertini | |
| D598,543 S | 8/2009 | Vogel et al. | |
| 7,569,035 B1 | 8/2009 | Wilmot et al. | |
| 7,615,041 B2 | 11/2009 | Sullivan et al. | |
| 7,648,482 B2 | 1/2010 | Edwards et al. | |
| 7,678,077 B2 | 3/2010 | Harris et al. | |
| 7,678,078 B1 | 3/2010 | Peyman et al. | |
| 7,722,581 B2 | 5/2010 | Peyman | |
| 7,914,803 B2 | 3/2011 | Chowhan et al. | |
| 7,918,814 B2 | 4/2011 | Prausnitz et al. | |
| 7,918,874 B2 | 4/2011 | Siegal | |
| 7,947,660 B2 | 5/2011 | Clark et al. | |
| 7,967,772 B2 | 6/2011 | McKenzie et al. | |
| 8,003,124 B2 | 8/2011 | Varner et al. | |
| 8,009,162 B2 | 8/2011 | Takatori | |
| 8,099,162 B2 | 1/2012 | Roy | |
| 8,114,110 B2 | 2/2012 | Bednarek et al. | |
| 8,128,960 B2 | 3/2012 | Kabra et al. | |
| 8,137,312 B2 | 3/2012 | Sundar et al. | |

(56) References Cited

U.S. PATENT DOCUMENTS

| | | |
|---|---|---|
| 8,172,830 B2 | 5/2012 | Christian et al. |
| 8,173,617 B2 | 5/2012 | Clark et al. |
| 8,192,408 B2 | 6/2012 | Nazzaro et al. |
| 8,197,435 B2 | 6/2012 | Prausnitz et al. |
| 8,197,443 B2 | 6/2012 | Sundar et al. |
| 8,221,353 B2 | 7/2012 | Cormier et al. |
| 8,235,967 B2 | 8/2012 | Chevallier et al. |
| D667,111 S | 9/2012 | Robinson |
| 8,287,494 B2 | 10/2012 | Ma |
| 8,303,599 B2 | 11/2012 | Hess et al. |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,403,941 B2 | 3/2013 | Peterson et al. |
| 8,430,862 B2 | 4/2013 | Peyman et al. |
| 8,448,786 B2 | 5/2013 | Tomes et al. |
| 8,460,242 B2 | 6/2013 | Paques et al. |
| 8,506,515 B2 | 8/2013 | Burns et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,617,121 B2 | 12/2013 | Lanin et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,727,117 B2 | 5/2014 | Maasarani |
| 8,747,365 B2 | 6/2014 | De Sausmarez Lintell |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,047 B2 | 11/2015 | Andino et al. |
| D750,223 S | 2/2016 | Andino et al. |
| 9,539,139 B2 | 1/2017 | Andino et al. |
| 9,572,800 B2 | 2/2017 | Zarnitsyn et al. |
| 9,636,253 B1 | 5/2017 | Andino et al. |
| 9,636,332 B2 | 5/2017 | Zarnitsyn et al. |
| 9,770,361 B2 | 9/2017 | Andino et al. |
| 9,788,995 B2 | 10/2017 | Prausnitz et al. |
| 9,931,330 B2 | 4/2018 | Zarnitsyn et al. |
| 9,937,075 B2 | 4/2018 | Andino et al. |
| 9,956,114 B2 | 5/2018 | Andino et al. |
| 10,188,550 B2 | 1/2019 | Andino et al. |
| 10,390,901 B2 | 8/2019 | Godfrey et al. |
| 10,517,756 B2 | 12/2019 | Andino et al. |
| 10,555,833 B2 | 2/2020 | Andino et al. |
| 10,632,013 B2 | 4/2020 | Prausnitz et al. |
| 10,722,396 B2 | 7/2020 | Andino et al. |
| 2001/0008961 A1 | 7/2001 | Hecker et al. |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0108875 A1 | 8/2002 | Feinberg et al. |
| 2002/0112981 A1 | 8/2002 | Cooper et al. |
| 2002/0142459 A1 | 10/2002 | Williams et al. |
| 2002/0156413 A1 | 10/2002 | Williams et al. |
| 2003/0009113 A1 | 1/2003 | Olson |
| 2003/0050602 A1 | 3/2003 | Pettis et al. |
| 2003/0083645 A1 | 5/2003 | Angel et al. |
| 2003/0139729 A1 | 7/2003 | Stegmann et al. |
| 2003/0171722 A1 | 9/2003 | Paques et al. |
| 2003/0233070 A1 | 12/2003 | De La Serna et al. |
| 2004/0019331 A1 | 1/2004 | Yeshurun |
| 2004/0039253 A1 | 2/2004 | Peyman et al. |
| 2004/0049150 A1 | 3/2004 | Dalton et al. |
| 2004/0059256 A1 | 3/2004 | Perez |
| 2004/0072105 A1 | 4/2004 | Yeshurun et al. |
| 2004/0106904 A1 | 6/2004 | Gonnelli et al. |
| 2004/0122359 A1 | 6/2004 | Wenz et al. |
| 2004/0141925 A1 | 7/2004 | Bosch et al. |
| 2004/0164454 A1 | 8/2004 | Gartstein et al. |
| 2004/0186084 A1 | 9/2004 | Alam et al. |
| 2004/0199130 A1 | 10/2004 | Chornenky et al. |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0009910 A1 | 1/2005 | Hughes et al. |
| 2005/0033230 A1 | 2/2005 | Alchas et al. |
| 2005/0055083 A1 | 3/2005 | Carranza et al. |
| 2005/0065137 A1 | 3/2005 | Jani et al. |
| 2005/0070819 A1 | 3/2005 | Poux et al. |
| 2005/0089545 A1 | 4/2005 | Kuwano et al. |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0148034 A1 | 7/2005 | Hariri et al. |
| 2005/0171507 A1 | 8/2005 | Christian et al. |
| 2005/0181017 A1 | 8/2005 | Hughes et al. |
| 2005/0203575 A1 | 9/2005 | Carson et al. |
| 2005/0209565 A1 | 9/2005 | Yuzhakov et al. |
| 2005/0244462 A1 | 11/2005 | Farooq |
| 2005/0244463 A1 | 11/2005 | Huang et al. |
| 2005/0244469 A1 | 11/2005 | Whitcup et al. |
| 2005/0245906 A1 | 11/2005 | Makower et al. |
| 2005/0256499 A1 | 11/2005 | Pettis et al. |
| 2005/0281862 A1 | 12/2005 | Karakelle et al. |
| 2006/0013859 A1 | 1/2006 | Yamada et al. |
| 2006/0032768 A1 | 2/2006 | Hamai et al. |
| 2006/0036318 A1 | 2/2006 | Foulkes |
| 2006/0055090 A1 | 3/2006 | Lee et al. |
| 2006/0084942 A1 | 4/2006 | Kim et al. |
| 2006/0086689 A1 | 4/2006 | Raju |
| 2006/0089607 A1 | 4/2006 | Chen |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0202385 A1 | 9/2006 | Xu et al. |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0016103 A1 | 1/2007 | Calasso et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093877 A1 | 4/2007 | Beecham et al. |
| 2007/0149944 A1 | 6/2007 | Tashiro et al. |
| 2007/0151882 A1 | 7/2007 | Cocheteux et al. |
| 2007/0178197 A1 | 8/2007 | Larue et al. |
| 2007/0191863 A1 | 8/2007 | De Juan et al. |
| 2007/0202116 A1 | 8/2007 | Burnie et al. |
| 2007/0202186 A1 | 8/2007 | Yamamoto et al. |
| 2007/0224278 A1 | 9/2007 | Lyons et al. |
| 2007/0225654 A1 | 9/2007 | Hess et al. |
| 2007/0233037 A1 | 10/2007 | Gifford, III et al. |
| 2007/0260201 A1 | 11/2007 | Prausnitz et al. |

(56) References Cited

U.S. PATENT DOCUMENTS

| | | |
|---|---|---|
| 2007/0270745 A1 | 11/2007 | Nezhat et al. |
| 2007/0270768 A1 | 11/2007 | Dacquay et al. |
| 2007/0282405 A1 | 12/2007 | Wong et al. |
| 2007/0287985 A1 | 12/2007 | Estes et al. |
| 2007/0299386 A1 | 12/2007 | Peyman |
| 2008/0008762 A1 | 1/2008 | Robinson et al. |
| 2008/0033351 A1 | 2/2008 | Trogden et al. |
| 2008/0058704 A1 | 3/2008 | Hee et al. |
| 2008/0058717 A1 | 3/2008 | Spector |
| 2008/0065002 A1 | 3/2008 | Lobl et al. |
| 2008/0071246 A1 | 3/2008 | Nazzaro et al. |
| 2008/0082841 A1 | 4/2008 | Juenemann et al. |
| 2008/0097335 A1 | 4/2008 | Trogden et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0152694 A1 | 6/2008 | Lobl et al. |
| 2008/0177239 A1 | 7/2008 | Li et al. |
| 2008/0200883 A1 | 8/2008 | Tomono |
| 2008/0228127 A1 | 9/2008 | Burns et al. |
| 2008/0234625 A1 | 9/2008 | Dacquay et al. |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0082321 A1 | 3/2009 | Edelman et al. |
| 2009/0088721 A1 | 4/2009 | Bizemont et al. |
| 2009/0105749 A1 | 4/2009 | De Juan et al. |
| 2009/0148527 A1 | 6/2009 | Robinson |
| 2009/0187167 A1 | 7/2009 | Sexton et al. |
| 2009/0259180 A1 | 10/2009 | Choi |
| 2009/0287161 A1 | 11/2009 | Traub et al. |
| 2009/0312782 A1 | 12/2009 | Park |
| 2010/0010004 A1 | 1/2010 | Van Emelen et al. |
| 2010/0010452 A1* | 1/2010 | Paques ............... A61F 9/0017 604/192 |
| 2010/0012537 A1 | 1/2010 | Farrar et al. |
| 2010/0015158 A1 | 1/2010 | Robinson et al. |
| 2010/0057011 A1 | 3/2010 | Charles |
| 2010/0074957 A1 | 3/2010 | Robinson et al. |
| 2010/0098772 A1 | 4/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0173866 A1 | 7/2010 | Hee et al. |
| 2010/0191176 A1 | 7/2010 | Ho et al. |
| 2010/0211079 A1 | 8/2010 | Aramant |
| 2010/0241102 A1 | 9/2010 | Ma |
| 2010/0256597 A1 | 10/2010 | Prausnitz et al. |
| 2010/0312120 A1 | 12/2010 | Meier |
| 2011/0004265 A1 | 1/2011 | Wenger et al. |
| 2011/0060310 A1 | 3/2011 | Prestrelski et al. |
| 2011/0112546 A1 | 5/2011 | Juan, Jr. et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0243999 A1 | 10/2011 | Dellamary et al. |
| 2011/0282298 A1 | 11/2011 | Again et al. |
| 2011/0295152 A1 | 12/2011 | Sasaki et al. |
| 2011/0306923 A1 | 12/2011 | Roy |
| 2012/0004245 A1 | 1/2012 | May et al. |
| 2012/0008327 A1 | 1/2012 | Brennan et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0078224 A1 | 3/2012 | Lerner et al. |
| 2012/0083727 A1 | 4/2012 | Barnett |
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123386 A1 | 5/2012 | Tsals |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'dea et al. |
| 2012/0136318 A1 | 5/2012 | Lanin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0197218 A1 | 8/2012 | Timm |
| 2012/0220917 A1 | 8/2012 | Silvestrini et al. |
| 2012/0226260 A1 | 9/2012 | Prausnitz et al. |
| 2012/0232522 A1 | 9/2012 | Prausnitz et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2013/0035662 A1 | 2/2013 | Decker et al. |
| 2013/0040895 A1 | 2/2013 | Robinson et al. |
| 2013/0041265 A1 | 2/2013 | Sostek et al. |
| 2013/0060202 A1 | 3/2013 | Thorley et al. |
| 2013/0065888 A1 | 3/2013 | Cetina-Cizmek et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0218269 A1 | 8/2013 | Schachar et al. |
| 2013/0226103 A1 | 8/2013 | Papiorek |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0253416 A1 | 9/2013 | Rotenstreich |
| 2013/0289545 A1 | 10/2013 | Baerveldt et al. |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0010823 A1 | 1/2014 | Robinson et al. |
| 2014/0012226 A1 | 1/2014 | Hochman |
| 2014/0027326 A1 | 1/2014 | Peruzzo |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0078854 A1 | 3/2014 | Head et al. |
| 2014/0088552 A1 | 3/2014 | Soni et al. |
| 2014/0094752 A1 | 4/2014 | Hiles |
| 2014/0102927 A1 | 4/2014 | Liversidge |
| 2014/0107566 A1 | 4/2014 | Prausnitz et al. |
| 2014/0114243 A1 | 4/2014 | Smith et al. |
| 2014/0135716 A1 | 5/2014 | Clarke et al. |
| 2014/0194834 A1 | 7/2014 | Passaglia et al. |
| 2014/0200518 A1 | 7/2014 | Ekman et al. |
| 2014/0224688 A1 | 8/2014 | Slemmen et al. |
| 2014/0231287 A1 | 8/2014 | Tomes et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0276482 A1 | 9/2014 | Astafieva et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2014/0353190 A1 | 12/2014 | Okihara et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1* | 2/2015 | Andino ............... A61M 5/3293 604/117 |
| 2015/0045731 A1 | 2/2015 | Gupta et al. |
| 2015/0045744 A1 | 2/2015 | Gupta et al. |
| 2015/0051545 A1 | 2/2015 | Henderson et al. |

(56) References Cited

U.S. PATENT DOCUMENTS

| | | |
|---|---|---|
| 2015/0051581 A1 | 2/2015 | Andino et al. |
| 2015/0110717 A1 | 4/2015 | Distel et al. |
| 2015/0129456 A1 | 5/2015 | Miller et al. |
| 2015/0133415 A1 | 5/2015 | Whitcup |
| 2015/0157359 A1 | 6/2015 | Shinzato et al. |
| 2015/0209180 A1 | 7/2015 | Prausnitz et al. |
| 2015/0223977 A1 | 8/2015 | Oberkircher et al. |
| 2015/0258120 A1 | 9/2015 | Zarnitsyn et al. |
| 2015/0297609 A1 | 10/2015 | Shah et al. |
| 2015/0320596 A1 | 11/2015 | Gifford, III et al. |
| 2016/0015895 A1 | 1/2016 | Blondino et al. |
| 2016/0015908 A1 | 1/2016 | Uemura et al. |
| 2016/0022486 A1 | 1/2016 | Clauson et al. |
| 2016/0106584 A1 | 4/2016 | Andino et al. |
| 2016/0106587 A1 | 4/2016 | Jarrett et al. |
| 2016/0166819 A1 | 6/2016 | Simmers |
| 2016/0193080 A1 | 7/2016 | Hammack et al. |
| 2016/0199581 A1 | 7/2016 | Cachemaille et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2016/0331738 A1 | 11/2016 | Jarrett et al. |
| 2017/0086725 A1 | 3/2017 | Woo et al. |
| 2017/0095369 A1 | 4/2017 | Andino et al. |
| 2017/0216228 A1 | 8/2017 | Asgharian et al. |
| 2017/0224435 A1 | 8/2017 | Godfrey et al. |
| 2017/0224534 A1 | 8/2017 | Andino et al. |
| 2017/0273827 A1 | 9/2017 | Prausnitz et al. |
| 2017/0290702 A1 | 10/2017 | Yamamoto et al. |
| 2017/0333416 A1 | 11/2017 | Zarnitsyn et al. |
| 2017/0340560 A1 | 11/2017 | Yamamoto et al. |
| 2018/0028358 A1 | 2/2018 | Andino et al. |
| 2018/0028516 A1 | 2/2018 | Zarnitsyn et al. |
| 2018/0042765 A1 | 2/2018 | Noronha et al. |
| 2018/0092897 A1 | 4/2018 | Zarnitsyn et al. |
| 2018/0325884 A1 | 11/2018 | Zarnitsyn et al. |
| 2018/0333297 A1 | 11/2018 | Andino et al. |
| 2019/0000669 A1 | 1/2019 | Hammack et al. |
| 2019/0231592 A1 | 8/2019 | Andino et al. |
| 2019/0240208 A1 | 8/2019 | Zarnitsyn et al. |
| 2019/0269702 A1 | 9/2019 | White et al. |
| 2019/0290485 A1 | 9/2019 | Andino et al. |
| 2019/0307606 A1 | 10/2019 | Andino et al. |
| 2019/0350755 A1 | 11/2019 | Andino et al. |
| 2020/0030143 A1 | 1/2020 | Andino et al. |
| 2020/0061357 A1 | 2/2020 | Jung et al. |
| 2020/0237556 A1 | 7/2020 | Prausnitz et al. |

FOREIGN PATENT DOCUMENTS

| | | |
|---|---|---|
| CN | 1604799 A | 4/2005 |
| CN | 1608587 A | 4/2005 |
| CN | 1681547 A | 10/2005 |
| CN | 1706365 | 12/2005 |
| CN | 1736474 | 2/2006 |
| CN | 1946445 A | 4/2007 |
| CN | 101052434 A | 10/2007 |
| CN | 101351239 A | 1/2009 |
| CN | 201192452 Y | 2/2009 |
| CN | 101559249 A | 10/2009 |
| CN | 201356711 Y | 12/2009 |
| CN | 201591741 U | 9/2010 |
| CN | 101854891 A | 10/2010 |
| CN | 101959519 A | 1/2011 |
| CN | 103037802 A | 4/2013 |
| CN | 103209733 A | 7/2013 |
| CN | 103857431 A | 6/2014 |
| CN | 204364577 U | 6/2015 |
| EA | 006961 | 6/2006 |
| EP | 1188456 A1 | 3/2002 |
| EP | 1568359 | 8/2005 |
| EP | 2193821 | 6/2010 |
| EP | 2307055 | 4/2011 |
| JP | 2001-525826 | 12/2001 |
| JP | 2007-510744 | 4/2007 |
| JP | 2007-518804 | 7/2007 |
| JP | 2009-183441 | 8/2009 |
| JP | 2009-531298 | 9/2009 |
| JP | 2010-234034 | 10/2010 |
| JP | 2013-543418 | 12/2013 |
| RU | 14351 U1 | 7/2000 |
| RU | 2344767 | 1/2009 |
| RU | 2353393 | 4/2009 |
| RU | 2428956 | 9/2011 |
| WO | WO 92/08406 | 5/1992 |
| WO | WO 92/20389 | 11/1992 |
| WO | WO 94/01124 | 1/1994 |
| WO | WO 94/12217 | 6/1994 |
| WO | WO 96/09838 | 4/1996 |
| WO | WO 98/51348 | 11/1998 |
| WO | WO 2000/007530 | 2/2000 |
| WO | WO 2000/007565 | 2/2000 |
| WO | WO 2001/041685 | 6/2001 |
| WO | WO 2002/058769 | 8/2002 |
| WO | WO 2003/002094 | 1/2003 |
| WO | WO 2003/024507 | 3/2003 |
| WO | WO 2003/039633 | 5/2003 |
| WO | WO 2005/011741 | 2/2005 |
| WO | WO 2005/032510 | 4/2005 |
| WO | WO 2005/046641 | 5/2005 |
| WO | WO 2005/069831 | 8/2005 |
| WO | WO 2005/072701 | 8/2005 |
| WO | WO 2005/074942 | 8/2005 |
| WO | WO 2005/107845 | 11/2005 |
| WO | WO 2006/004595 | 1/2006 |
| WO | WO 2006/042252 | 4/2006 |
| WO | WO 2006/058189 | 6/2006 |
| WO | WO 2006/128034 | 11/2006 |
| WO | WO 2006/138719 | 12/2006 |
| WO | WO 2007/069697 A1 | 6/2007 |
| WO | WO 2007/100745 | 9/2007 |
| WO | WO 2007/130105 | 11/2007 |
| WO | WO 2007/131050 | 11/2007 |
| WO | WO 2007/150018 | 12/2007 |
| WO | WO 2008/082637 | 7/2008 |
| WO | WO 2009/067325 | 5/2009 |
| WO | WO 2009/105534 | 8/2009 |
| WO | WO 2009/114521 | 9/2009 |
| WO | WO 2010/009034 | 1/2010 |
| WO | WO 2010/054660 | 5/2010 |
| WO | WO 2010/132751 | 11/2010 |
| WO | WO 2011/057065 | 5/2011 |
| WO | WO 2011/123722 | 10/2011 |
| WO | WO 2011/139713 | 11/2011 |
| WO | WO 2012/019136 | 2/2012 |
| WO | WO 2012/051575 | 4/2012 |
| WO | WO 2012/118498 | 9/2012 |
| WO | WO 2012/125869 | 9/2012 |
| WO | WO 2012/125872 | 9/2012 |
| WO | WO 2012/162459 | 11/2012 |
| WO | WO 2013/050236 | 4/2013 |
| WO | WO 2013/098166 | 7/2013 |
| WO | WO 2013/151904 | 10/2013 |
| WO | WO 2014/028285 | 2/2014 |
| WO | WO 2014/036009 | 3/2014 |
| WO | WO 2014/074823 | 5/2014 |
| WO | WO 2014/179698 | 11/2014 |
| WO | WO 2014/197317 | 12/2014 |
| WO | WO 2015/015467 | 2/2015 |
| WO | WO 2015/095772 | 6/2015 |
| WO | WO 2015/195842 | 12/2015 |
| WO | WO 2015/196085 | 12/2015 |
| WO | WO 2016/042162 | 3/2016 |
| WO | WO 2016/042163 | 3/2016 |
| WO | WO 2017/120600 | 7/2017 |
| WO | WO 2017/120601 | 7/2017 |
| WO | WO 2017/139375 | 8/2017 |
| WO | WO 2017/190142 | 11/2017 |
| WO | WO 2017/192565 | 11/2017 |

(56) References Cited

OTHER PUBLICATIONS

Office Action for U.S. Appl. No. 15/708,779, dated Jul. 15, 2019, 8 pages.
Office Action for Canadian Application No. 2,882,184, dated May 1, 2019, 3 pages.
Office Action for U.S. Appl. No. 14/894,161, dated Apr. 6, 2018, 19 pages.
Examination Report No. 1 for Australian Application No. 2014259694, dated May 24, 2018, 2 pages.
First Office Action for Chinese Application No. 201480025034.4, dated Apr. 24, 2018, 10 pages.
Office Action for Eurasian Application No. 201592109, dated Jan. 31, 2018, 2 pages.
Office Action for European Application No. 14791646.4, dated Sep. 17, 2018, 5 pages.
Office Action for Israeli Application No. 242395, dated May 7, 2019, 7 pages.
Notice of Reasons for Rejection for Japanese Application No. 2016-512068, dated Mar. 26, 2018, 4 pages.
Office Action for New Zealand Application No. 714172, dated Feb. 1, 2018, 4 pages.
Office Action for New Zealand Application No. 714172, dated Jul. 24, 2018, 4 pages.
Office Action for New Zealand Application No. 714172, dated Dec. 12, 2018, 3 pages.
Partial European Search Report for European Application No. 18176172.7, dated Oct. 30, 2018, 13 pages.
Extended European Search Report for European Application No. 18176172.7, dated Feb. 6, 2019, 11 pages.
Notice of Reasons for Rejection for Japanese Application No. 2018-142345, dated Jun. 6, 2019, 6 pages.
Office Action for U.S. Appl. No. 15/946,838, dated Jun. 27, 2019, 7 pages.
Office Action for U.S. Appl. No. 16/381,213, dated May 31, 2019, 7 pages.
Examination Report No. 1 for Australian Application No. 2015277133, dated Mar. 29, 2019, 6 pages.
First Office Action for Chinese Application No. 201580044250.8, dated Apr. 24, 2018, 14 pages.
Second Office Action for Chinese Application No. 201580044250.8, dated Jan. 2, 2019, 7 pages.
Third Office Action for Chinese Application No. 201580044250.8, dated Jul. 17, 2019, 9 pages.
Notice of Reasons for Rejection for Japanese Application No. 2016-573927, dated Mar. 26, 2019, 10 pages.
Office Action for Russian Application No. 2017101236/14, dated Jan. 18, 2019, 4 pages.
Office Action and Search Report for Russian Application No. 2017101236/14, dated May 16, 2019, 16 pages.
Office Action for U.S. Appl. No. 15/319,045, dated Jul. 13, 2018, 13 pages.
Office Action for U.S. Appl. No. 15/319,045, dated Apr. 2, 2019, 14 pages.
Extended European Search Report for European Application No. 15810459.6, dated Apr. 16, 2018, 11 pages.
Notice of Reasons for Rejection for Japanese Application No. 2016-574090, dated Mar. 4, 2019, 18 pages.
Office Action for Russian Application No. 2017101660, dated Mar. 5, 2019, 7 pages.
Office Action for Brazilian Application No. PI 0708133-2, dated Feb. 26, 2019, 11 pages.
Office Action for U.S. Appl. No. 11/709,941, dated Dec. 14, 2018, 17 pages.
Extended European Search Report for European Application No. 18176149.5, dated Jan. 22, 2019, 11 pages.
Office Action for U.S. Appl. No. 15/398,538, dated Jul. 20, 2018, 12 pages.
Office Action for U.S. Appl. No. 15/398,538, dated Apr. 16, 2019, 8 pages.
Extended European Search Report for European Application No. 18199418.7, dated Jul. 5, 2019, 9 pages.
Extended European Search Report for European Application No. 17750694.6, dated Sep. 2, 2019, 6 pages.
Office Action for U.S. Appl. No. 15/427,823, dated Jul. 20, 2018, 11 pages.
International Search Report and Written Opinion for International Application No. PCT/US2017/065796, dated Apr. 12, 2018, dated Apr. 12, 2018, 9 pages.
Falkenstein, I. A. et al., "Comparison of visual acuity in macular degeneration patients measured with Snellen and Early Treatment Diabetic Retinopathy study charts," Ophthalmology 115(2):319-323 (Feb. 2008).
Furrer, P. et al., "Ocular tolerance of preservatives and alternatives," European Journal of Pharmaceutics and Biopharmaceutics, 53(3):263-280 (2002).
Haller, J. A., "Intraocular Steroids in the Office. New formulations offer preservative-free triamcinolone without relying on compounding pharmacies," Retinal Physician [online]. Retrieved from the Internet: <URL: https://www.retinalphysician.com/supplements/2009/february-2009/special-edition/intraocular-steroids-in-the-office>, Feb. 1, 2009, 4 pages.
Haller, J. A. et al., "Evaluation of the safety and performance of an applicator for a novel intravitreal dexamethasone drug delivery system for the treatment of macular edema," Retina, 29(1):46-51 (2009).
Kadam, R. S. et al., "Suprachoroidal delivery in a rabbit ex vivo eye model: influence of drug properties, regional differences in delivery, and comparison with intravitreal and intracameral routes," Molecular Vision, 19:1198-1210 (May 2013).
Karim, R. et al., "Interventions for the treatment of uveitic macular edema: a systematic review and meta-analysis," Clinical Ophthalmology, 7:1109-1144 (2013).
Sallam, A. et al., "Repeat intravitreal triamcinolone acetonide injections in uveitic macular oedema," Acta Ophthalmologica, 90(4):e323-e325 (2012).
Office Action for U.S. Appl. No. 11/743,535, dated Aug. 19, 2010, 7 pages.
Office Action for U.S. Appl. No. 11/743,535, dated Dec. 29, 2009, 6 pages.
International Search Report and Written Opinion for International Application No. PCT/US2007/068055, dated Nov. 7, 2007, 13 pages.
Office Action for Canadian Application No. 2797258, dated Nov. 21, 2016, 3 pages.
Extended European Search Report for European Application No. 11777924.9, dated Feb. 4, 2015, 7 pages.
Office Action for Russian Application No. 2012147341, dated Feb. 26, 2015, 8 pages.
Office Action for U.S. Appl. No. 12/767,768, dated Jun. 10, 2011, 5 pages.
International Search Report and Written Opinion for International Application No. PCT/US2011/033987, dated Feb. 14, 2012, 7 pages.
Examination Report No. 1 for Australian Application No. 2015230874, dated Jul. 28, 2017, 11 pages.
Office Action for Japanese Application No. 2016-068174, dated Mar. 1, 2017, 8 pages.
Office Action for U.S. Appl. No. 13/447,246, dated Oct. 28, 2013, 5 pages.
Office Action for U.S. Appl. No. 13/453,407, dated Mar. 20, 2013, 5 pages.
Office Action for U.S. Appl. No. 14/136,657, dated Dec. 16, 2016, 7 pages.
Extended Search Report for European Application No. 13833318.2, dated Apr. 1, 2016, 7 pages.
Office Action for U.S. Appl. No. 14/424,685, dated Jun. 10, 2016, 10 pages.
Office Action for U.S. Appl. No. 14/424,685, dated Dec. 12, 2016, 15 pages.
International Search Report and Written Opinion for International Application No. PCT/US2013/056863, dated Nov. 26, 2013, 8 pages.

(56) References Cited

OTHER PUBLICATIONS

Supplementary European Search Report for European Application No. 14808034.4, dated Jan. 23, 2017, 7 pages.
Office Action for European Application No. 14808034.4, dated Nov. 8, 2017, 4 pages.
Office Action for U.S. Appl. No. 14/894,161, dated Dec. 27, 2016, 17 pages.
Office Action for U.S. Appl. No. 14/894,161, dated Sep. 20, 2017, 21 pages.
International Search Report and Written Opinion for International Application No. PCT/US2014/040254, dated Oct. 31, 2014, 9 pages.
Office Action for Eurasian Application No. 201592109, dated Apr. 1, 2016, 4 pages.
Extended Search Report for European Application No. 14791646.4, dated Nov. 21, 2016, 6 pages.
Office Action for European Application No. 14791646.4, dated Dec. 4, 2017, 5 pages.
Search Report and Written Opinion for Singapore Application No. 11201509051V, dated Nov. 2, 2016, 6 pages.
Examination Report for Singapore Application No. 11201509051V, dated Feb. 1, 2017, 4 pages.
International Search Report and Written Opinion for International Application No. PCT/US2014/036590, dated Dec. 10, 2014, 10 pages.
Office Action for U.S. Appl. No. 14/268,687, dated May 19, 2016, 6 pages.
Office Action for U.S. Appl. No. 14/523,243, dated Feb. 27, 2015, 14 pages.
Extended European Search Report for European Application No. 15808944.1, dated Jan. 19, 2018, 14 pages.
International Search Report and Written Opinion for International Application No. PCT/US2015/036299, dated Nov. 10, 2015, 11 pages.
Partial Supplementary European Search Report for European Application No. 15810459.6, dated Dec. 22, 2017, 13 pages.
Office Action for U.S. Appl. No. 15/383,582, dated May 5, 2017, 10 pages.
International Search Report and Written Opinion for International Application No. PCT/US2015/036715, dated Jan. 19, 2016, 9 pages.
Office Action for Canadian Application No. 162010, dated Aug. 25, 2015, 1 page.
International Search Report and Written Opinion for International Application No. PCT/US2014/071623, dated Jun. 25, 2015, 18 pages.
Office Action for Chinese Application No. 200780014501.3, dated Mar. 11, 2010, 6 pages.
Office Action for Chinese Application No. 200780014501.3, dated Aug. 26, 2010, 10 pages.
Office Action for European Application No. 07751620.1, dated Sep. 13, 2013, 7 pages.
Extended European Search Report for European Application No. 07751620.1, dated Jan. 15, 2013, 10 pages.
Office Action for European Application No. 07751620.1, dated Dec. 11, 2014, 5 pages.
Invitation pursuant to Article 94(3) and Rule 71(1) for European Application No. 07751620.1, dated Feb. 29, 2016, 3 pages.
Summons to Attend Oral Proceedings Pursuant to Rule 115(1) EPC for European Application No. 07751620.1, mailed Jun. 13, 2017, 8 pages.
Office Action for Japanese Application No. 2008-556462, dated Jul. 24, 2012, 15 pages.
Office Action for India Application No. 3345/KOLNP/2008, dated May 21, 2015, 3 pages.
Office Action for Singapore Application No. 200805936-2, dated Oct. 15, 2012, 7 pages.
Search Report and Written Opinion for Singapore Application No. 200805936-2, dated Jun. 8, 2010, 13 pages.
Supplementary Search Report for Singapore Application No. 200805936-2, dated May 6, 2011, 8 pages.
Supplementary Search Report for Singapore Application No. 200805936-2, dated May 26, 2011, 8 pages.
Office Action for U.S. Appl. No. 11/709,941, dated Jun. 24, 2014, 11 pages.
Office Action for U.S. Appl. No. 11/709,941, dated Mar. 23, 2011, 9 pages.
Office Action for U.S. Appl. No. 11/709,941, dated Feb. 11, 2015, 14 pages.
Office Action for U.S. Appl. No. 11/709,941, dated Oct. 27, 2011, 8 pages.
Office Action for U.S. Appl. No. 11/709,941, dated Apr. 12, 2016, 25 pages.
Office Action for U.S. Appl. No. 11/709,941, dated Dec. 27, 2016.
Office Action for U.S. Appl. No. 11/709,941, dated Jan. 16, 2018, 32 pages.
International Search Report and Written Opinion for International Application No. PCT/US2007/004874, dated Jun. 4, 2008, 6 pages.
Office Action for Chinese Application No. 201110093644.6, dated Mar. 26, 2012, 11 pages.
Office Action for Chinese Application No. 201110093644.6, dated Sep. 7, 2012, 8 pages.
Office Action for Chinese Application No. 201110093644.6, dated Dec. 14, 2012, 3 pages.
Office Action for U.S. Appl. No. 13/842,218, dated Jul. 5, 2016, 11 pages.
Office Action for U.S. Appl. No. 13/842,288, dated Oct. 6, 2015, 10 pages.
First Office Action for Chinese Application No. 201180060268.9, dated Oct. 10, 2014, 9 pages.
Second Office Action for Chinese Application No. 201180060268.9, dated Jun. 18, 2015, 4 pages.
Third Office Action for Chinese Application No. 201180060268.9, dated Feb. 5, 2016, 6 pages.
Examination Report for European Application No. 11776049.6, dated Oct. 25, 2016, 4 pages.
Office Action for Japanese Application No. 2013-534049, dated Sep. 1, 2015, 11 pages.
Office Action for U.S. Appl. No. 13/273,775, dated Feb. 12, 2015, 13 pages.
Office Action for U.S. Appl. No. 13/273,775, dated Jul. 3, 2014, 12 pages.
International Search Report and Written Opinion for International Application No. PCT/US2011/056433, dated Apr. 25, 2012, 17 pages.
Office Action for Chinese Application No. 201510144330.2, dated Apr. 5, 2016, 17 pages.
Second Office Action for Chinese Application No. 201510144330.2, dated Dec. 20, 2016, 13 pages.
Third Office Action for Chinese Application No. 201510144330.2, dated Jun. 28, 2017, 3 pages.
Office Action for U.S. Appl. No. 14/821,310, dated Jul. 14, 2017, 11 pages.
First Office Action for Chinese Application No. 201610805842.3, dated Jul. 21, 2017, 4 pages.
Office Action for U.S. Appl. No. 15/427,823, dated Apr. 20, 2017, 8 pages.
Office Action for U.S. Appl. No. 15/427,823, dated Sep. 27, 2017, 7 pages.
International Search Report and Written Opinion for International Application No. PCT/US2017/017014, dated Apr. 27, 2017, 13 pages.
International Search Report and Written Opinion for International Application No. PCT/US2017/030609, dated Oct. 6, 2017, 12 pages.
International Search Report and Written Opinion for International Application No. PCT/US2017/030439, dated Aug. 1, 2017, 12 pages.
International Search Report and Written Opinion for International Application No. PCT/US2017/046553, dated Dec. 13, 2017, 14 pages.
Abbott Medical Optics (HEALON5@OVD on http://abbottmedicaloptics.com/products/cataract/ovds/healon5-viscoelastic (2004).

(56) References Cited

OTHER PUBLICATIONS

Anthem, Medical Policy, Suprachoroidal Injection of a Pharmacologic Agent, Nov. 14, 2013, Retrieved from the Internet: <URL: http://www.anthem.com/medicalpolicies/policies/mp_pw_b076412.htm>, 3 pages.

Beer, P. J. et al., "Photographic Evidence of Vitreous Wicks After Intravitreal Injections," Retina Today, 2(2):24-39 (Mar. 2007).

Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E-Abstract 5330 (2010), 2 pages.

Brown, D. M., "Aflibercept for Treatment of Diabetic Macular Edema," Retina Today, Jul./Aug. 2011, pp. 59-60.

Careforde Healthcare, B Braun Glass Loss-Of-Resistance Syringes #332155—5cc Glass Loss-Of-Resistance Syringe, Luer Lock Metal Tip, 10/cs, [online], <http://careforde.com/b-braun-glass-loss-of-resistance-syringes-332155-5cc-glass-loss-of-r . . . > (2014), 2 pages.

Careforde Healthcare, B Braun Glass Loss-Of-Resistance Syringes #332158—10cc Glass Loss-Of-Resistance Syringe, Luer Slip Metal Tip, 10/cs, (2014), 2 pages.

Careforde Healthcare, B Braun Perifix Plastic Loss-Of-Resistance Syringes #332152—8cc Plastic Luer Lock Loss-of-Resistance Syringe, 50/cs, [online], <http://careforde.com/b-braun-perifix-plastic-loss-of-resistance-syringes-332152-8cc-plasti . . . > (2014), 2 pages.

Cho, S. W. et al., "Drug delivery to the suprachoroidal space," Chap. 12 in: Ocular Drug Delivery Systems: Barriers and Application of Nanoparticulate Systems, Thassu, D. et al. (eds.), CRC Press, pp. 235-258 (2012).

Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).

Claims filed in copending U.S. Appl. No. 15/454,636, on Mar. 9, 2017, pp. 1-30.

Dinning, W. J., "Steroids and the eye-indications and complications," Postgraduate Medical Journal, vol. 52, 1976, pp. 634-638.

Edwards, A. et al., "Fiber matrix model of sclera and corneal stroma for drug delivery to the eye," AIChE Journal, 44(1):214-225 (1998).

Einmahl, S. et al., "Evaluation of a novel biomaterial in the suprachoroidal space of the rabbit eye," Invest. Ophthalmol. Vis. Sci., 43(5):1533-1539 (2002).

Einmahl, S. et al., "Ocular biocompatibility of a poly(ortho ester) characterized by autocatalyzed degradation," J. Biomed. Mater. Res., 67(1):44-53 (2003).

"Epidural," Wikipedia [online], retrieved from the internet on Sep. 3, 2014, <URL: http:/en.wikipedia.org/wiki/Epidural>, 21 pages.

Feldkamp, L. A. et al., "Practical cone-beam algorithm," J. Opt. Soc. Am. A, 1(6):612-619 (1984).

Geroski, D. H. et al., "Drug delivery for posterior segment eye disease," Invest. Ophthalmol. Vis. Sci., 41(5):961-964 (2000).

Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).

Gilger, et al., "A Novel Bioerodible Deep Scleral Lamellar Cyclosporine Implant for Uveitis," Invest Ophthalmol Vis Sci, vol. 47, Issue 6, 2006, pp. 2596-2605.

Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, Arvo (2002), 2 pages.

Heller, J., Ocular delivery using poly(ortho esters), Adv. Drug. Deliv. Rev., 57(14):2053-2062 (2005).

Hoagan et al., Chapter Eight, Choroid, In Histology of the Human Eye, 9 pages (1971).

Jain, A., "Pseudo loss of resistance in epidural space localization: A complication of subcutaneous emphysema or simply a faulty technique," Saudi J. Anaseth, 5(1):108-109 (2011) (Abstract).

Jiang, J. et al., "Measurement and Prediction of Lateral Diffusion within Human Sclera," Investigative Ophthalmology & Visual Science, 47(7):3011-3016 (2006).

Jiang, J. et al., "Coated Microneedles for Drug Delivery to the Eye," Investigative Ophthalmology & Visual Science, 48(9):4038-4043 (2007).

Jiang, J. et al., "Intrascleral drug delivery to the eye using hollow microneedles," Pharmaceutical Research, 26(2):395-403 (2009).

Lee, S-B et al., "Drug delivery through the sclera: effects of thickness, hydration and sustained release systems," Experimental Eye Research, 78:599-607 (2004).

Lee et al., "Thixotropic property in pharmaceutical formulations," Journal of Controlled Release (2009) 136:88-98.

Lindfield, D. et al., "Suprachoroidal Devices in Glaucoma. The Past, Present, and Future of Surgery for Suprachoroidal Drainage," Cataract & Refractive Surgery Today [online], Oct. 2013, Retrieved from the Internet: <URL: http://bmctoday.net/crstodayeurope/2013/10/article.asp?f=suprachoroidal-devices-in-glau . . . >, 3 pages.

Loewen, N., "The suprachoroidal space in glaucoma surgery," Jul. 2012, 4 pages.

Maurice, D., "Review: Practical Issues in Intravitreal Drug Delivery," J. Ocul. Pharmacol. Ther., 17(4):393-401 (2001).

McAllister, D. V. et al., "Microfabricated needles for transdermal delivery of macromolecules and nanoparticles: Fabrication methods and transport studies," Proc. Nat'l Acad. Sci USA, 100(24):13755-13760 (2003).

Norman, D., Epidural analgesia using loss of resistance with air versus saline: Does it make a difference? Should we reevaluate our practice?, AANA Journal, 71(6):449-453 (Dec. 2003).

Olsen, T. W. et al., "Cannulation of the Suprachoroidal Space: A Novel Drug Delivery Methodology to the Posterior Segment," American J. Opthamology, 142(5):777-787 (2006).

Olsen, , T., "Drug Delivery to the Suprachoroidal Space Shows Promise," Retina Today, pp. 36-39 (Mar./Apr. 2007).

Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).

Patel, S. R. et al., "Targeted administration into the suprachoroidal space using a microneedle for drug delivery to the posterior segment of the eye," Investigative Ophthalmology & Visual Science, 53(8):4433-4441 (Jul. 2012).

Patel, S. et al., "Suprachoroidal Drug Delivery Using Microneedles," Invest. Ophthalmol. Vis. Sci., 49:E-Abstract 5006 (2008), 2 pages.

Patel, S. et al., "Drug Binding to Sclera," Invest Ophthalmol Vis Sci., 50:E-Abstract 5968 (2009), 2 pages.

Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.

Patel, S. R. et al., "Suprachoroidal drug delivery to the back of the eye using hollow microneedles," Pharmaceutical Research, 28(1):166-176 (2011). Published online: Sep. 21, 2010.

Penkov, M. A. et al., "A ten-year experience with usage of the method of supra-choroidal administration of medicinal substances," Oftalmol. Zh., 35(5):281-285 (1980).

Prausnitz, M. R. et al., "Permeability of cornea, sclera and conjunctiva: A literature analysis for drug delivery to the eye," Journal of Pharmaceutical Sciences, 87(12):1479-1488 (1998).

Prausnitz, M. R. et al., "Measurement and prediction of transient transport across sclera for drug delivery to the eye," Industrial and Engineering Chemistry Research, 37(8):2903-2907 (1998).

Prausnitz, M. R., "Microneedles for Ocular Drug Delivery," Review of Olsen, T., Drug Delivery to the Suprachoroidal Space Shows Promise, Retina Today, Mar./Apr. 2007, p. 39.

Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.

Saberski, L. R. et al., "Identification of the epidural space: Is loss of resistance to air a safe technique? A review of the complications related to the use of air," Regional Anesthesia, 22(1):3-15 (1997).

Scott, I. U. et al., "Baseline characteristics and response to treatment of participants with hemiretinal compared with branch retinal or

(56) References Cited

OTHER PUBLICATIONS central retinal vein occlusion in the standard care vs. corticosteroid for retinal vein occlusion (SCORE)," Arch. Ophthalmol., 130(12):1517-1524 (Dec. 2012).

Shuler, R. K. et al., "Scleral Permeability of a Small, Single-Stranded Oligonucleotide," Journal of Ocular Pharmacology and Therapeutics, 20(2):159-168 (2004) (Abstract).

Wang, P. M. et al., "Minimally Invasive Extraction of Dermal Interstitial Fluid for Glucose Monitoring Using Microneedles," Diabetes Technology & Therapeutics, 7(1):131-141 (2005).

You, X. D. et al., "Chitosan drug delivery system implanting into suprachoroidal space for perforating ocular injury in rabbits," International Journal of Ophthalmology, 5(1):74-76 (2005) [English Abstract].

Office Action for European Application No. 11777924.9, dated Oct. 1, 2019, 5 pages.

Office Action for U.S. Appl. No. 16/826,443, dated Jun. 1, 2020, 6 pages.

Office Action for Canadian Application No. 2,882,184, dated Jan. 24, 2020, 6 pages.

Office Action for Canadian Application No. 2,882,184, dated Aug. 18, 2020, 3 pages.

Office Action for European Application No. 13833318.2, dated Aug. 26, 2020, 5 pages.

Office Action for U.S. Appl. No. 15/619,065, dated Jun. 13, 2019, 30 pages.

Office Action for U.S. Appl. No. 15/619,065, dated Jan. 28, 2020, 24 pages.

Preliminary Office Action for Brazilian Application No. 112015027762-4, dated Jan. 17, 2020, 6 pages.

Office Action for Canadian Application No. 2,911,290, dated Jun. 18, 2020, 5 pages.

Office Action for European Application No. 14791646.4, dated Feb. 11, 2020, 5 pages.

Office Action for Israeli Application No. 242395, dated Aug. 10, 2020, 12 pages.

Office Action for Mexican Application No. MX/a/2015/015282, dated May 15, 2019, 8 pages.

Office Action for European Application No. 18176172.7, dated Feb. 7, 2020, 4 pages.

Office Action for U.S. Appl. No. 16/591,067, dated Nov. 18, 2019, 7 pages.

Office Action for U.S. Appl. No. 15/872,206, dated May 1, 2020, 8 pages.

Office Action for U.S. Appl. No. 15/872,206, dated Oct. 19, 2020, 9 pages.

Office Action for U.S. Appl. No. 16/178,162, dated Jun. 10, 2020, 18 pages.

Extended European Search Report for European Application No. 17880800.2, dated Jun. 2, 2020, 13 pages.

Doncaster and Bassetlaw Hospitals, NHS Foundation Trust, Department of Ophthalmology, "Intravitreal injection of triamcinolone," Jul. 2010, [online]. Retrieved from the Internet: <URL: http://www.dbh.nhs.uk/Library/Patient_Information_Leaflets/WPR32110%20IIT%20No%20crops.pdf>, 2 pages.

HomeCEU, "How Does Iontophoresis Work?", [Online], Retrieved from the Internet: <https://www.homeceuconnection.com/blog/how-does-iontophoresis-work/, 2018, 5 pages.

First Office Action for Chinese Application No. 201780062253.3, dated Dec. 25, 2020, 22 pages.

\* cited by examiner

200

```
┌─────────────────────────────────────────────────────┐
│ Insert a distal tip of a puncture member of a       │
│ medical injector into a first region of a target    │
│ tissue. The medical injector includes a medicament  │
│ container, a hub, and the puncture member, a distal │
│ tip of the puncture member extending from a distal  │
│ end surface of the hub before and during the        │
│ inserting                                           │
│ 202                                                 │
└─────────────────────────────────────────────────────┘
                         │
                         ▼
┌─────────────────────────────────────────────────────┐
│ Manually exert a force on a proximal end portion of │
│ an actuation rod to move a distal end portion of    │
│ the actuation rod within the medicament container,  │
│ movement of the distal end portion of the actuation │
│ rod causing:                                        │
│ 204                                                 │
└─────────────────────────────────────────────────────┘
                         │
                         ▼
┌─────────────────────────────────────────────────────┐
│ The distal tip of the puncture member to move in a  │
│ distal direction relative to the distal end surface │
│ of the hub from the first region of the target      │
│ tissue to a second region of the target tissue. The │
│ force being insufficient to produce a flow of the   │
│ substance through the puncture member when the      │
│ distal tip of the puncture member is within the     │
│ first region of the target tissue                   │
│ 204A                                                │
└─────────────────────────────────────────────────────┘
                         │
                         ▼
┌─────────────────────────────────────────────────────┐
│ The substance to flow from the pressure chamber     │
│ through the puncture member when the distal tip of  │
│ the puncture member is within a second region of    │
│ the target tissue                                   │
│ 204B                                                │
└─────────────────────────────────────────────────────┘
```

FIG. 24

DEVICES AND METHODS FOR ADJUSTING THE INSERTION DEPTH OF A NEEDLE FOR MEDICAMENT DELIVERY

CROSS-REFERENCE TO RELATED APPLICATIONS

This application priority to and the benefit of U.S. Provisional Application Ser. No. 62/374,300, entitled "Multi-Length Infinitely Adjustable Microneedle," filed Aug. 12, 2016, which is incorporated herein by reference in its entirety.

BACKGROUND

The embodiments described herein relate generally to the field of ophthalmic therapies and more particularly to ocular injection devices for delivery and/or removal of a substance, such as a fluid therapeutic agent, into and/or from ocular tissues for treatment of the eye.

Although needles are used in transdermal and intraocular drug delivery, there remains a need for improved microneedle devices and methods, particularly for delivery of substances (e.g., drugs) into the posterior region of the eye. Many inflammatory and proliferative diseases in the posterior region (or other regions) of the eye require long-term pharmacological treatment. Examples of such diseases include macular degeneration, diabetic retinopathy, and uveitis. It is often difficult to deliver effective doses of a drug to the back of the eye using conventional delivery methods such as topical application or an intravitreal administration (IVT), which has poor efficacy, and systemic administration, which often causes significant side effects. For example, while eye drops are useful in treating conditions affecting the exterior surface of the eye or tissues at the front of the eye, the eye drops are often not sufficiently conveyed to the back of the eye, as may be required for the treatment of some of the retinal diseases listed above.

Although there have been advances in the past decade regarding the utilization of systemically delivered substances, there are obstacles to wide spread adoption of such methods. For example, in certain situations, direct injection into the eye (e.g., into the vitreous) using conventional 27 gauge or 30 gauge needles and syringes can be effective. Direct injection, however, can be associated with significant safety risks, and physicians often require professional training to effectively perform such methods. Moreover, in some instances, targeted injection of a therapeutic agent is desirable. In such instances, however, the relatively small anatomic structures of the eye often result in significant challenges to placing a needle at a target location using known devices and methods, especially as they pertain to placing the distal end of the needle at the desired depth within the eye. Furthermore, IVT administration can have side effects such as increased intraocular pressure or faster onset of cataract formation.

Some known devices for ocular injection do not provide the mechanism for adjusting needle length so that the needle can be inserted into the eye to the desired depth. Some known systems also do not provide an efficient and reliable mechanism for determining when the needle tip is in the desired location, for example, the suprachoroidal space (SCS) of the eye. For example, some known methods of injecting substances into ocular tissue include using complicated visualization system or sensors to control the placement of the needle or cannula within the eye, which can necessitate such methods being performed at a surgical center.

Moreover, such shortcomings in known systems and methods are exacerbated because the size and thickness of various layers included in the eye can vary substantially from one person to another. For example, the thickness of the conjunctiva and the sclera can be substantially different and their true value cannot easily be predetermined via standard techniques. Furthermore, the thickness of these layers can also be different in different portions of the eye and at different times of the day in the same eye and location. Therefore, using known systems and methods it can be challenging to determine and/or adjust the length of the needle for puncturing the eye, such that a tip of the needle is at the desired depth, for example, the SCS. If the inserted needle length is too short, penetration through the sclera may not be achieved. Conversely, if the inserted needle length is too long, the tip can traverse beyond the SCS and damage the retina of the eye. Further, known systems do not provide a convenient way to detect the position of the needle tip within the eye.

In addition to the issues associated with placing the needle tip in the desired location, injection of a drug into different target layers of the eye can cause variability in the amount of the force required for insertion of the needle and/or injection of the medicament. Different layers of the eye can have different densities. For example, the sclera generally has a higher density (or lower tissue porosity) than the conjunctiva or the SCS. Differences in the density of the target region or layer can produce different backpressure resisting the distal movement of the needle into the tissue and also resisting the flow of the medicament from the needle exit. Thus, injection into a relatively dense ocular material such as sclera requires more motive pressure to expel the medicament from the needle than is required when injecting a medicament into the SCS. In addition to overcoming the resistance of the bodily tissue, the resistance (i.e., frictional losses) of the injection system must also be overcome for successful repeatable drug delivery. Thus, the injection force to expel the medicament also depends on the density and viscosity of the liquid medicament, the length of the needle, and/or the diameter of the needle. To inject certain medicaments into the eye via desired needles (e.g., 27 gauge, 30 gauge, or even smaller) can require more force than many practitioners are comfortable (or capable of) applying.

Thus, a need exists for improved injection devices and methods, which can assist in facilitating injection of a viscous medicament into ocular tissue.

SUMMARY

Devices and methods for ocular injection are described herein. In some embodiments, an apparatus includes a housing, an adjustment member, and a puncture member. A proximal end portion of the housing can be coupled to a medicament container, and a distal end portion of the housing includes a hub surface. The hub surface is configured to contact a target surface of a target tissue. The adjustment member is within the inner volume such that the inner volume is separated into a first chamber and a second chamber. The first chamber is in fluid communication with the medicament container. The adjustment member is configured to transition within the inner volume between a first configuration and a second configuration. The puncture member is coupled to the adjustment member. A proximal end portion of the puncture member is fluidically coupled to the first chamber such that a substance can be conveyed from the medicament container through the puncture member via the first chamber. A distal tip of the puncture member extends from the hub surface by a first distance when the adjustment member is in the first configuration, and by a second distance when the adjustment member is in the second configuration. The second distance is greater than the first distance.

In some embodiments, a method includes inserting a distal tip of a puncture member of a medical injector into a first region of a target tissue. The medical injector includes a medicament container, a hub, and the puncture member. A distal tip of the puncture member extends from a distal end surface of the hub by a first distance before and during the inserting. A substance is conveyed from the medicament container into a pressure chamber defined within the hub when the distal tip is within the target tissue to produce a pressure within the pressure chamber. The pressure causes the distal tip of the puncture member to move within the first region of the target tissue such that the distal tip of the puncture member extends from the distal end surface of the hub by a second distance greater than the first distance. The pressure is insufficient to produce a flow of the substance from the pressure chamber through the puncture member when the distal tip of the puncture member is within the first region of the target tissue. The pressure produces the flow of the substance from the pressure chamber through the puncture member when the distal tip of the puncture member is within a second region of the target tissue.

BRIEF DESCRIPTION OF THE DRAWINGS

FIG. 24 is a flow chart of a method of injecting a medicament according to an embodiment.

DETAILED DESCRIPTION

Figure 1:
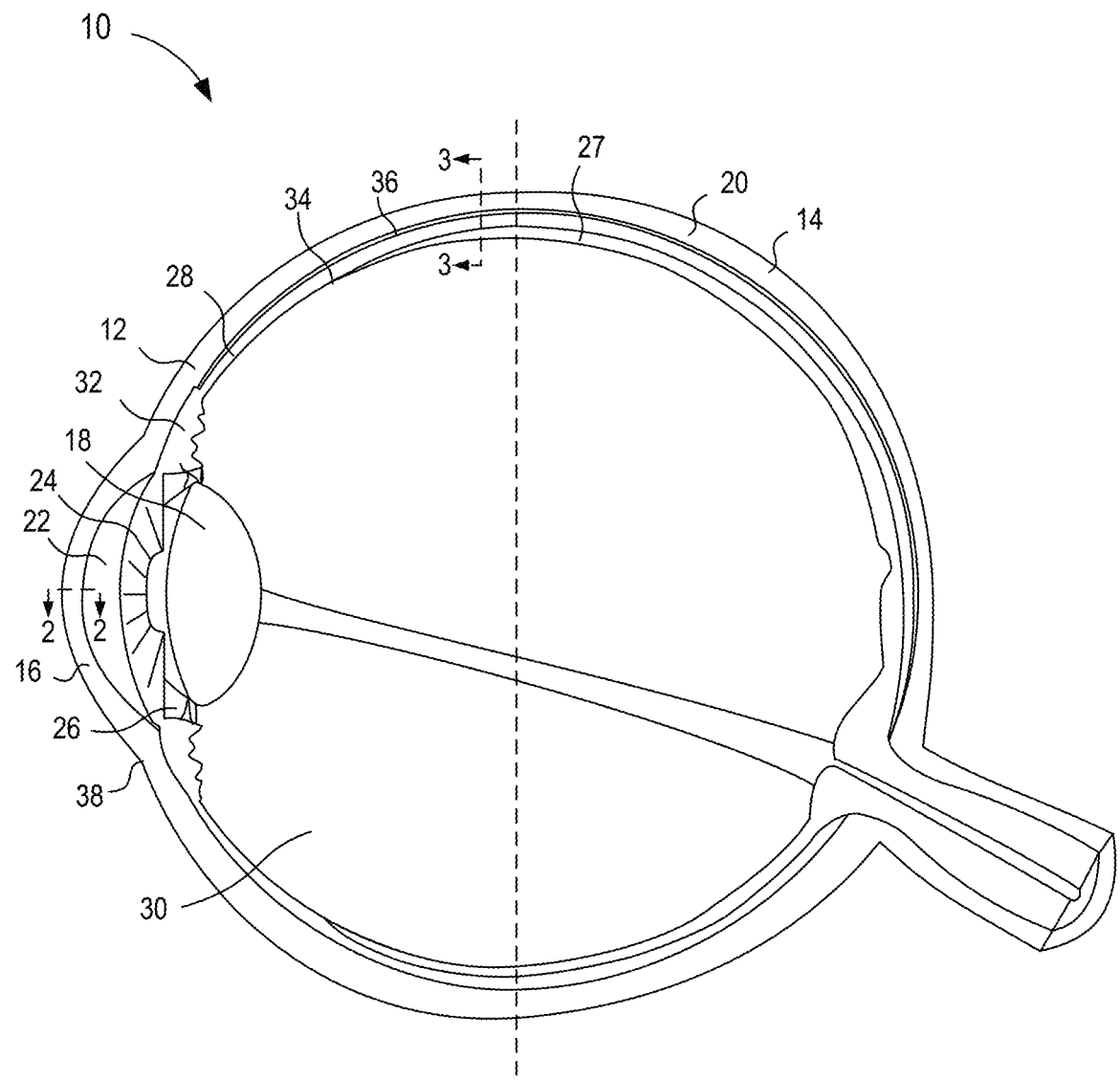
FIG. 1 is a cross-sectional view of an illustration of the human eye.

Devices and methods for ocular injection are described herein. In some embodiments, an apparatus includes a housing, an adjustment member, and a puncture member. A proximal end portion of the housing can be coupled to a medicament container, and a distal end portion of the housing includes a hub surface. The hub surface is configured to contact a target surface of a target tissue. The adjustment member is within the inner volume such that the inner volume is separated into a first chamber and a second chamber. The first chamber is in fluid communication with the medicament container. The adjustment member is configured to transition within the inner volume between a first configuration and a second configuration. The puncture member is coupled to the adjustment member. A proximal end portion of the puncture member is fluidically coupled to the first chamber such that a substance can be conveyed from the medicament container through the puncture member via the first chamber. A distal tip of the puncture member extends from the hub surface by a first distance when the adjustment member is in the first configuration, and by a second distance when the adjustment member is in the second configuration. The second distance is greater than the first distance.

In some embodiments, an apparatus includes a housing, an adjustment member, and a puncture member. The has an inner surface defining an inner volume. A proximal end portion of the housing is configured to be coupled to a medicament container. A distal end portion of the housing includes a hub surface that can contact a target surface of a target tissue (e.g., during an injection operation). The adjustment member is within the inner volume such that the inner surface and a proximal surface of the adjustment member define a pressure chamber. The pressure chamber is in fluid communication with the medicament container when the proximal end portion of the housing is coupled to the medicament container. The adjustment member is configured to move within the inner volume and relative to the medicament container between a first position and a second position. The puncture member is coupled to the adjustment member and has a proximal end portion in fluid communication with the pressure chamber such that a substance can be conveyed from the medicament container through the puncture member via the pressure chamber. A distal tip of the puncture member extends from the hub surface by a first distance when the adjustment member is in the first position, and by a second distance when the adjustment member is in the second position. The second distance greater than the first distance.

In some embodiments, a method includes inserting a distal tip of a puncture member of a medical injector into a first region of a target tissue. The medical injector includes a medicament container, a hub, and the puncture member. A distal tip of the puncture member extends from a distal end surface of the hub by a first distance before and during the inserting. A substance is conveyed from the medicament container into a pressure chamber defined within the hub when the distal tip is within the target tissue to produce a pressure within the pressure chamber. The pressure causes the distal tip of the puncture member to move within the first region of the target tissue such that the distal tip of the puncture member extends from the distal end surface of the hub by a second distance greater than the first distance. The pressure is insufficient to produce a flow of the substance from the pressure chamber through the puncture member when the distal tip of the puncture member is within the first region of the target tissue. The pressure produces the flow of the substance from the pressure chamber through the puncture member when the distal tip of the puncture member is within a second region of the target tissue.

In some embodiments, a method includes inserting a distal tip of a puncture member of a medical injector into a first region of a target tissue. The medical injector includes a medicament container, a hub, and the puncture member. A distal tip of the puncture member extends from a distal end surface of the hub before and during the inserting. A force is exerted on a proximal end portion of an actuation rod to move a distal end portion of the actuation rod within the medicament container. The movement of the distal end portion of the actuation rod causes: A) the distal tip of the puncture member to move in a distal direction relative to the distal end surface of the hub from the first region of the target tissue to a second region of the target tissue; and B) the substance to flow from the pressure chamber through the puncture member when the distal tip of the puncture member is within a second region of the target tissue. The force is insufficient to produce a flow of the substance from the pressure chamber through the puncture member when the distal tip of the puncture member is within the first region of the target tissue.

The term "about" when used in connection with a referenced numeric indication means the referenced numeric indication plus or minus up to 10 percent of that referenced numeric indication. For example, "about 100" means from 90 to 110.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a microneedle or injection device described herein first inserted inside the patient's body would be the distal end, while the opposite end of the microneedle or injection device (e.g., the end of the medical device being manipulated by the operator) would be the proximal end of the microneedle.

The term "fluid-tight" is understood to encompass both a hermetic seal (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at a constant position and at fluid pressures of less than about 5 pounds per square inch gauge (psig).

As used herein, a "set" can refer to multiple features or a singular feature with multiple parts. For example, when referring to set of walls, the set of walls can be considered as one wall with distinct portions, or the set of walls can be considered as multiple walls.

As used herein, the terms "medicament container," and "medicament containment chamber" are used interchangeably to refer to an article configured to contain a volume of a substance, for example, a medicament. A medicament container can include a vial, ampule (or ampoule), inner portion of a syringe, or the like.

As used herein, the terms "delivery member," "puncture member," and "puncturing member" are used interchangeably to refer to an article configured to pierce tissue layers and deliver a substance to (or remove the substance from) a target tissue layer. Examples of a puncture member include a needle or a microneedle.

As used in this specification and the appended claims, the terms "drug" or "medicament" include any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

As used herein, "non-surgical" ocular drug delivery devices and methods refer to methods and devices for drug delivery that do not require general anesthesia and/or retrobulbar anesthesia (also referred to as a retrobulbar block). Alternatively or additionally, a "non-surgical" ocular drug delivery method is performed with an instrument having a diameter of 28 gauge or smaller. Alternatively or additionally, "non-surgical" ocular drug delivery methods do not require a guidance mechanism that is typically required for ocular drug delivery via a shunt or cannula.

The non-surgical treatment methods and devices described herein are particularly useful for the local delivery of drugs to the posterior region of the eye, for example the retinochoroidal tissue, macula, retinal pigment epithelium (RPE) and optic nerve in the posterior segment of the eye. In some embodiments, the non-surgical methods and microneedles provided herein can be used to target drug delivery to specific posterior ocular tissues or regions within the eye or in neighboring tissue. In some embodiments, the methods described herein deliver drug specifically to the sclera, the choroid, the Brach's membrane, the retinal pigment epithelium, the subretinal space, the retina, the macula, the optic disk, the optic nerve, the ciliary body, the trabecular meshwork, the aqueous humor, the vitreous humor, and/or other ocular tissue or neighboring tissue in the eye of a human subject in need of treatment. The methods and microneedle assemblies provided herein can be used to target drug delivery to specific posterior ocular tissues or regions within the eye or in neighboring tissue.

In some embodiments, the methods described herein can be used for the treatment of a patient in need of treatment of macular edema associated with uveitis (e.g., infectious, non-infectious, intermediate, posterior or pan uveitis), macular edema associated with RVO (e.g., branch retinal vein occlusion (BRVO), hemiretinal vein occlusion (HRVO), or central retinal vein occlusion (CRVO)). In such embodiments, any of the devices or methods described herein can be used to non-surgically administer a drug, e.g., an anti-inflammatory drug (e.g., triamcinolone) or a vascular endothelial growth factor (VEGF) modulator (e.g., VEGF antagonist) to the suprachoroidal space of one or both eyes for at least one dosing session. Non-surgical administration can be achieved by inserting a microneedle having an infinitely variable length (within a range) into one or both eyes of the patient, for example the sclera, and injecting or infusing a drug formulation through the inserted microneedle and into the suprachoroidal space of the eye. In some embodiments, the effective amount of the drug administered to the SCS provides higher therapeutic efficacy of the drug, compared to the therapeutic efficacy of the drug when the identical dosage is administered intravitreally, topically, intracamerally, parenterally or orally. In some embodiments, the microneedle drug delivery methods described herein precisely deliver the drug into the SCS for subsequent local delivery to nearby posterior ocular tissues (e.g., the retina and choroid) in need of treatment. The drug may be released into the ocular tissues from the infused volume (or, e.g., from microparticles or nanoparticles in the drug formulation) for an extended period, e.g., several hours or days or weeks or months, after the non-surgical drug administration has been completed. This beneficially can provide increased bioavailability of the drug relative, for example, to delivery by topical application of the drug formulation to ocular tissue surfaces, or increased bioavailability compared to oral, parenteral on intravitreal administration of the same drug dosage.

According to the methods and using the needle assemblies described herein, the SCS drug delivery methods advantageously include precise control of the depth of insertion into the ocular tissue, so that the microneedle tip can be placed into the eye. This allows the drug formulation to flow into the suprachoroidal space and into one or more posterior ocular tissues surrounding the SCS, e.g., the choroid and retina. In some embodiments, insertion of the microneedle is in the sclera of the eye. The microneedle can then move, as a result of the fluid pressure within the injection device, to achieve the desired depth for SCS delivery. In some embodiments, drug flow into the SCS is accomplished without contacting underlying tissues with the microneedle, such as choroid and retina tissues.

The term "suprachoroidal space," is used interchangeably with suprachoroidal, SCS, suprachoroid and suprachoroidia, and describes the potential space in the region of the eye disposed between the sclera and choroid. This region primarily is composed of closely packed layers of long pigmented processes derived from each of the two adjacent tissues; however, a space can develop in this region as a result of fluid or other material buildup in the suprachoroidal space and the adjacent tissues. Those skilled in the art will appreciate that the suprachoroidal space frequently is expanded by fluid buildup because of some disease state in the eye or as a result of some trauma or surgical intervention. In the present description, however, the fluid buildup is intentionally created by infusion of a drug formulation into the suprachoroid to create the suprachoroidal space (which is filled with drug formulation). Not wishing to be bound by theory, it is believed that the SCS region serves as a pathway for uveoscleral outflow (i.e., a natural process of the eye moving fluid from one region of the eye to the other through) and becomes a real space in instances of choroidal detachment from the sclera.

Figure 2:
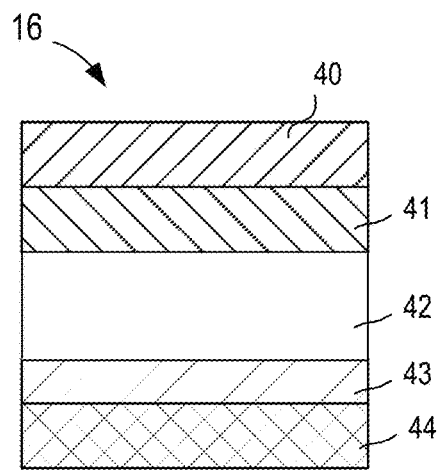
FIG. 2 is a cross-sectional view of a portion of the human eye of FIG. 1 taken along the line 2-2.
Figure 3:
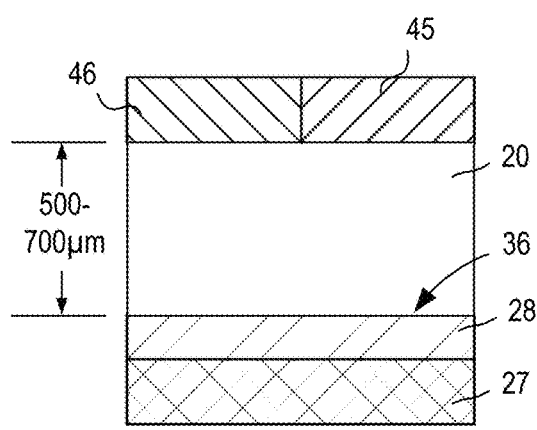
FIGS. 3 and 4 are cross-sectional views of a portion of the human eye of FIG. 1 taken along the line 3-3, illustrating the suprachoroidal space without and with, respectively, the presence of a fluid.
Figure 4:
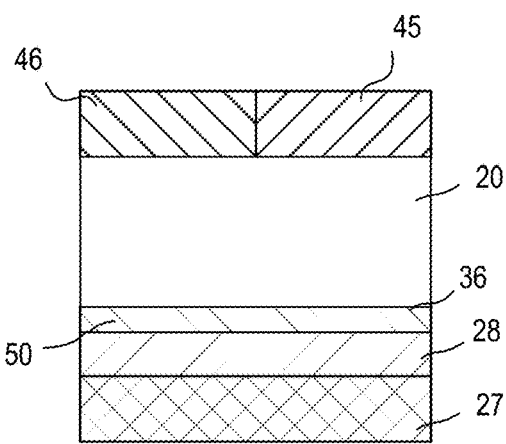

As used herein, "ocular tissue" and "eye" include both the anterior segment of the eye (i.e., the portion of the eye in front of the lens) and the posterior segment of the eye (i.e., the portion of the eye behind the lens). For reference, FIGS. 1-4 are various views of an eye 10 (with FIGS. 2-4 being cross-sectional views). While specific regions are identified, those skilled in the art will recognize that the proceeding identified regions do not constitute the entirety of the eye 10, rather the identified regions are presented as a simplified example suitable for the discussion of the embodiments herein. The eye 10 includes both an anterior segment 12 (the portion of the eye in front of and including the lens) and a posterior segment 14 (the portion of the eye behind the lens). The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The cornea 16 and the sclera 20 collectively form a limbus 38 at the point at which they meet. The exposed portion of the sclera 20 on the anterior segment 12 of the eye is protected by a clear membrane referred to as the conjunctiva 45 (see e.g., FIGS. 2 and 3). Underlying the sclera 20 is the choroid 28 and the retina 27, collectively referred to as retinachoroidal tissue. A vitreous humour 30 (also referred to as the "vitreous") is disposed between a ciliary body 32 (including a ciliary muscle and a ciliary process) and the retina 27. The anterior portion of the retina 27 forms an ora serrata 34. The loose connective tissue, or potential space, between the choroid 28 and the sclera 20 is referred to as the suprachoroid. FIG. 2 illustrates the cornea 16, which is composed of the epithelium 40, the Bowman's layer 41, the stroma 42, the Descemet's membrane 43, and the endothelium 44. FIG. 3 illustrates the sclera 20 with surrounding Tenon's Capsule 46 or conjunctiva 45, suprachoroidal space 36, choroid 28, and retina 27, substantially without fluid and/or tissue separation in the suprachoroidal space 36 (i.e., the in this configuration, the space is "potential" suprachoroidal space). As shown in FIG. 3, the sclera 20 has a thickness between about 500 µm and 700 µm. FIG. 4 illustrates the sclera 20 with the surrounding Tenon's Capsule 46 or the conjunctiva 45, suprachoroidal space 36, choroid 28, and retina 27, with fluid 50 in the suprachoroidal space 36.

The dashed line in FIG. 1 represents the equator of the eye 10. In some embodiments, the insertion site of any of the microneedles and/or methods described herein is between the equator and the limbus 38 (i.e., in the anterior portion 12 of the eye 10) For example, in some embodiments, the insertion site is between about two millimeters and 10 millimeters (mm) posterior to the limbus 38. In other embodiments, the insertion site of the microneedle is at about the equator of the eye 10. In still other embodiments, the insertion site is posterior the equator of the eye 10. In this manner, a drug formulation can be introduced (e.g., via the microneedle) into the suprachoroidal space 36 at the site of the insertion and can flow through the suprachoroidal space 36 away from the site of insertion during an infusion event (e.g., during injection).

Figure 5:
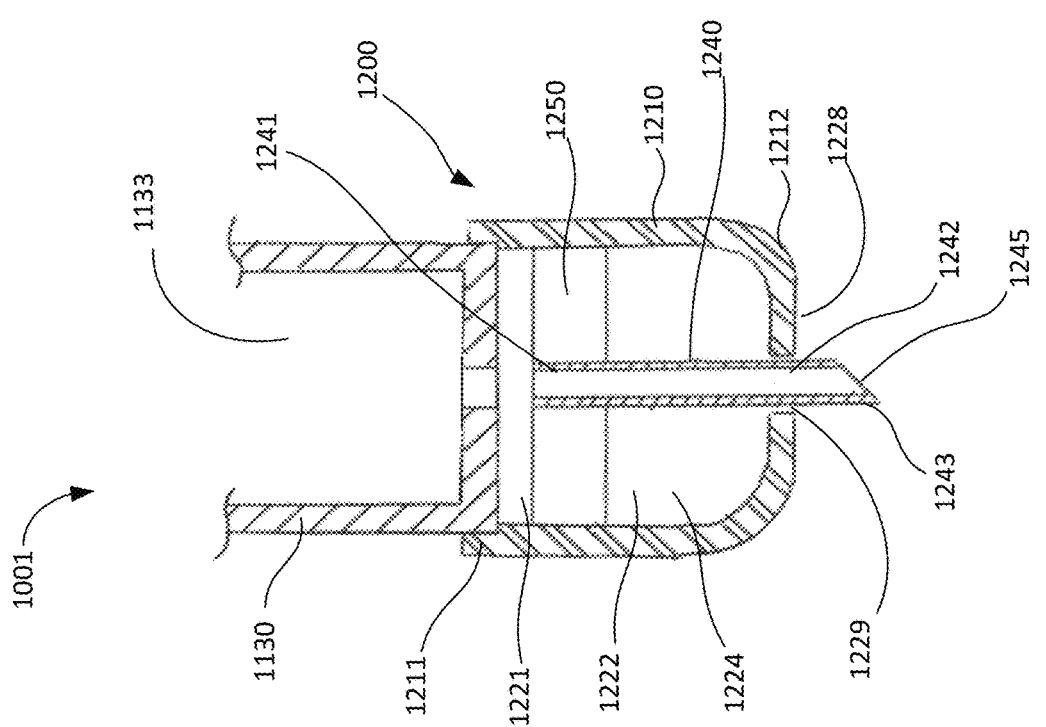
FIG. 5 is a schematic illustration of an injector assembly according to an embodiment.

In some embodiments, an injector assembly can be configured for non-surgical use, and can provide for precise control of the depth of insertion of a delivery member or puncture member (e.g., a microneedle) into a target tissue. In this manner, the delivery member or puncture member can move, relative to a hub, during the insertion/injection operation such that the tip of the delivery member can be placed in the desired position within the target tissue. Such placement can allow the drug formulation to flow into the desired portion of the target tissue. For example, FIG. 5 is a schematic illustration of an injector assembly 1001 according to an embodiment. The injector assembly 1001 includes a medicament container 1130, a housing 1210, an adjustment member 1250, and a puncture member 1240.

The housing 1210 includes a proximal end portion 1211 and a distal end portion 1212. The proximal end portion 1211 can be coupled to the medicament container 1130. The medicament container 1130 can be any suitable container that defines a reservoir or volume 1133 within which a drug (also referred to as a medicament) can be contained. For example, in some embodiments, the medicament container 1130 can be a syringe that includes an actuation rod (not shown in FIG. 5) within the volume 1133. In such embodiments, the actuation rod can be reciprocated within the volume 1133 to either produce a vacuum within the medicament container 1130 (e.g., to draw a medicament into the volume 1133) or produce a pressure within the medicament container 1130 (e.g., to expel the medicament from the volume 1133). In some embodiments, the medicament container 1130 can be a prefilled (or prefillable) syringe, that includes one or more doses of any suitable substance (the medicament or drug) within the volume 1133. For example, in some embodiments, the medicament container contains at least one of a VEGF, a VEGF inhibitor, a PDGFR inhibitor, or a combination of any of the VEGF, the VEGF inhibitor, and the PDGFR inhibitor.

The proximal end portion 1211 of the housing 1210 can be coupled to the medicament container 1130 in any suitable manner. For example, in some embodiments, the housing 1210 can be removably coupled to the medicament container 1130, for example, by a Luer connector, a threaded joint, a snap-fit, a latch, a friction (or press-on) fit, or any other suitable coupling features. In this manner, the housing 1210 (and therefore the puncture member 1240) can be removed from the medicament container 1130 to allow a vial or other container to be coupled to the medicament container (e.g., to allow a dose of drug to be conveyed into the volume 1133). For example, in some embodiments, the injector assembly 1001 can be included within a kit that includes a needle assembly (e.g., the housing 1210, the puncture member 1240, and the adjustment member 1250), one or more drug vials, a vial adapter, and the medicament container 1130 (e.g., a syringe). In some embodiments, the injector assembly 1001 (or any of the injector assemblies described herein) can be included in any of the kits shown and described in U.S. patent application Ser. No. 15/427,823, entitled "Ocular Injection Kit, Packaging, and Methods of Use," Filed Feb. 8, 2017, which is incorporated by reference herein in its entirety. In other embodiments, the housing 1210 can be permanently coupled to the medicament container 1130. Similarly stated, in some embodiments, the housing 1210 can be coupled to the medicament container 1130 in a manner that precludes removal of the housing 1210 from the medicament container 1130 during the intended (or "normal") use of the injector assembly 1001. In such embodiments, the housing 1210 can be permanently coupled to the medicament container 1130 by a weld joint, an adhesive, a bond, or the like. In yet other embodiments, the housing 1210 and the medicament container 1130 can be monolithically constructed.

The distal end portion 1212 of the housing 1210 includes a hub surface 1228 and defines an opening 1229 within the hub surface 1228. The hub surface 1228 is a contact surface having any suitable shape and/or size configured to contact a target surface S of a target tissue T during an injection operation (see FIGS. 6 and 7). For example, in some embodiments, the hub surface 1228 is configured to deform the target surface S (e.g., the conjunctiva of the eye) when the distal end portion 1212 is brought into contact with the target surface S. In some embodiments, the hub surface 1228 can have a substantially convex shape, for example, a hemispherical shape, and can define a sealing portion that forms a substantially fluid-tight seal with the target surface S when the distal end portion 1212 is brought into contact with the target surface S. For example, in some embodiments, the hub surface 1228 can deform the target surface S to produce a substantially fluid-tight seal between the housing 1210 and the target surface S, about the opening 1229. In some embodiments, the hub surface 1228 can include any of the characteristics of any of the hubs or hub surfaces shown and described in U.S. Pat. No. 9,180,047, entitled "Apparatus and Methods for Ocular Injection," which is incorporated herein by reference in its entirety.

Figure 6:
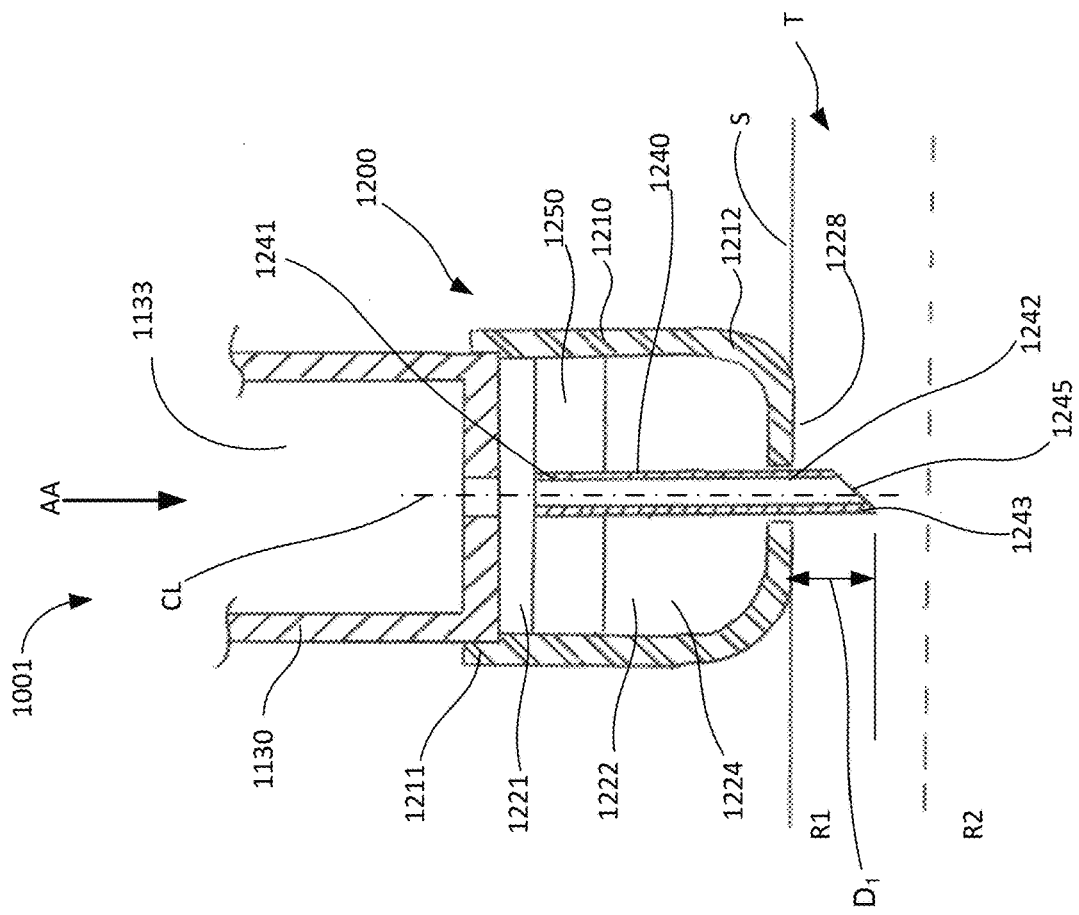
FIGS. 6 and 7 are schematic illustrations of the injector assembly shown in FIG. 5, in a first configuration and a second configuration, respectively.
Figure 7:
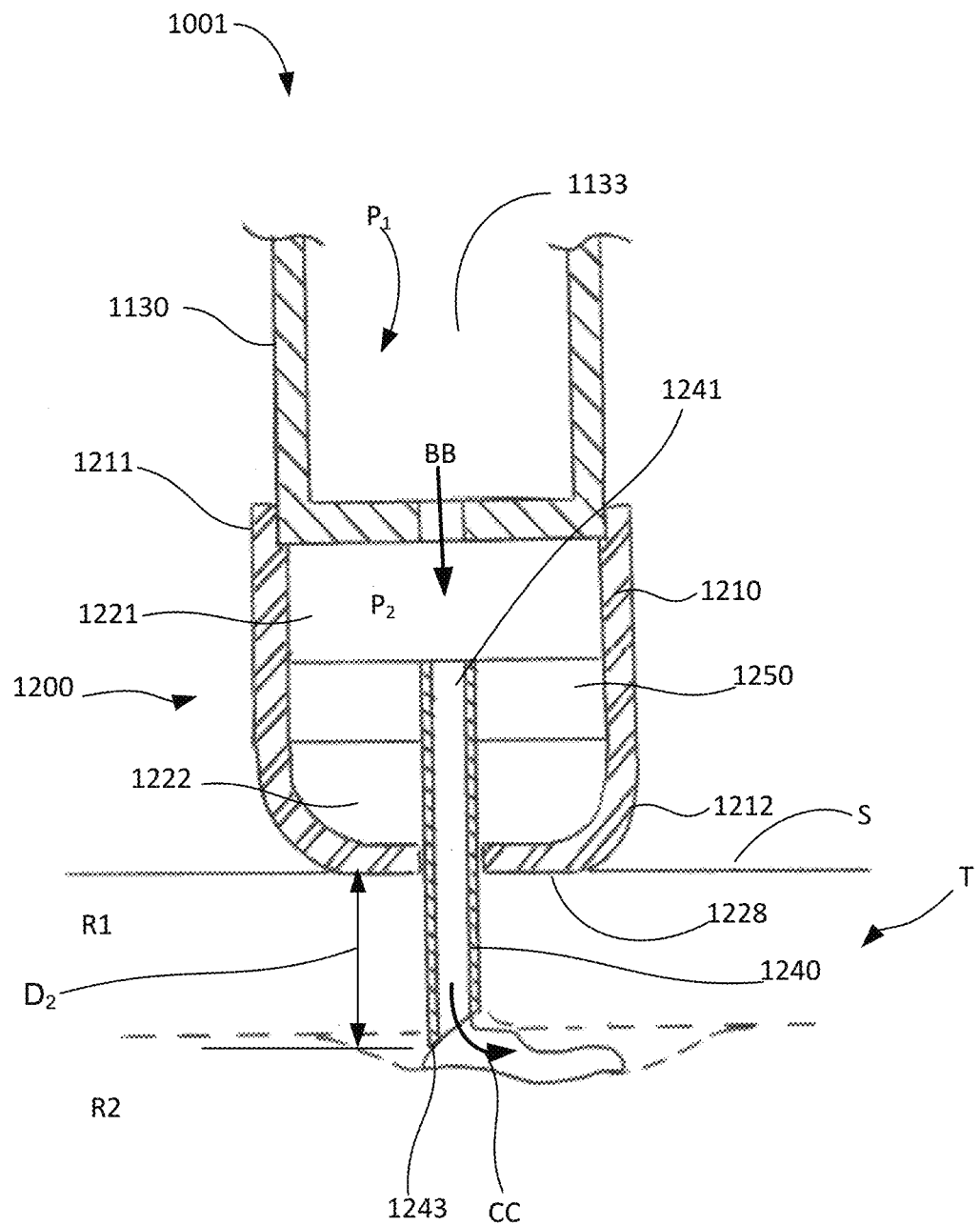

The adjustment member 1250 is disposed within an inner volume 1224 defined by the housing 1210, and separates the inner volume into a first chamber 1221 (also referred to as a pressure chamber) and a second chamber 1222. As shown, the first (or pressure) chamber 1221 is in fluid communication with the medicament container 1130 (and/or the volume 1133) when the housing 1210 is coupled to the medicament container 1130. In this manner, as described herein, a medicament from the medicament container 1130 can be conveyed into the first chamber 1221. Moreover, the medicament within the first chamber 1221 can be pressurized to transition the adjustment member between a first configuration (FIGS. 5 and 6) and a second configuration (FIG. 7). Transitioning the adjustment member 1250 produces movement of the puncture member 1240, as described below. In some embodiments, the adjustment member 1250 can fluidically isolate the first chamber 1221 from the second chamber 1222 (e.g., via a seal or the like).

The puncture member 1240 can be any suitable device to puncture the target surface S and define a passageway within the target tissue T. The puncture member 1240 also provides a lumen through which the medicament can be delivered into the target tissue T (see FIG. 7, with medicament delivery indicated by the arrow CC). As shown, the puncture member 1240 includes a proximal end portion 1241 and a distal end portion 1242, and defines a lumen through which the medicament can be conveyed from the medicament container 1130 and/or the first chamber 1221. The puncture member 1240 is coupled to the adjustment member 1250 such that the proximal end portion 1241 is in fluid communication with the first chamber 1221. In this manner, a substance (e.g., a drug or medicament) can be conveyed from the medicament container 1130 through the puncture member 1240 via the first chamber 1221. The distal end portion 1242 of the puncture member 1240 includes a distal end surface 1245 that is beveled or a sharpened to facilitate puncturing the target tissue T. The distal end surface 1245 can have any suitable shape, size and/or geometry (e.g., bevel angle, bevel height, bevel aspect ratio or the like). For example, in some embodiments, the puncture member 1240 (and any of the puncture members described herein, including the puncture members 2240, 3240, and 4240) can include any of the beveled surfaces shown and described in International Patent Application Publication No. WO2014/036009, entitled, "Apparatus and Methods for Drug Delivery Using Microneedles," filed on Aug. 27, 2013, the disclosure of which is incorporated by reference herein in its entirety.

The distal end surface 1245 includes a distal tip 1243. Similarly stated, the distal tip 1243 is formed by the intersection of the distal end surface 1245 and an outer side wall of the puncture member 1240. Referring to FIG. 6, the distal tip 1243 of the puncture member extends from the hub surface 1228 (or through the opening 1229) by a first distance $D_1$ when the adjustment member 1250 is in the first configuration. Referring to FIG. 7, the distal tip 1243 of the puncture member extends from the hub surface 1228 (or through the opening 1229) by a second distance $D_2$ when the adjustment member 1250 is in the second configuration. In this manner, the position of the puncture member 1240 relative to the hub surface 1228 (also referred to as the effective length) can change during an injection operation to ensure that the distal tip 1243 (and therefore the opening in the beveled distal end surface 1245) is placed within the desired region of (or at the desired depth within) the target tissue T during medicament delivery. Moreover, as described herein, the position of the distal tip 1243 relative to the hub surface 1228 is changed automatically and in an infinite number of positions (within a predefined range). Said another way, the position of the distal tip 1243 relative to the hub surface 1228 is changed in response to the user actuating the device without any additional input from the user. Thus, the user need not separately manipulate any needle adjustment features, and need not monitor the actual depth of the distal tip 1243 within the target tissue T.

The operation of the injector assembly is described with reference to FIGS. 6-9. To initiate an injection, the injector assembly 1001 is moved distally towards the target surface S when the adjustment member 1250 is in its first configuration (or position) within the housing 1210. Because the distal tip 1243 extends from the hub surface 1228 by the distance $D_1$, the distal tip 1243 is the first portion of the injector assembly to contact the target surface S. Thus, further distal movement of the injector assembly 1001, as shown by the arrow AA in FIG. 6, causes the distal tip 1243 to be inserted into a first region R1 of the target tissue. The insertion of the distal tip 1243 when the adjustment member is in its first configuration (or position) is referred to as the initial insertion operation.

In some embodiments, the initial insertion operation can include inserting the distal tip 1243 until hub surface 1228 contacts the target surface S. Thus, the insertion depth of the puncture member 1240 after the initial insertion is the same as the effective length of the puncture member 1240 (which is the distance $D_1$). In some embodiments, the distal tip 1243 can be inserted until hub surface 1228 deforms the target surface S. For example, in some embodiments, the target tissue T is the eye 10. By deforming the target surface S and/or underlying target tissue T, the hub surface 1228 can form a substantially fluid-tight seal with the conjunctiva around the insertion site.

In some embodiments, the initial insertion operation can be performed such that a centerline CL of the puncture member 1240 and a surface line tangent to the target surface S define an angle of entry of between about 75 degrees and about 105 degrees. Similarly stated, an insertion angle of the puncture member 1240 relative to the target surface S is within the range of between about 75 degrees and about 105 degrees, inclusive of all ranges therebetween. In this manner, the size of the insertion zone can be reduced, thereby minimizing injury and inflammation, which can be caused by any lateral travel of the puncture member 1240 within the target tissue T. Furthermore, insertion of the puncture member 1240 substantially normal to the target surface S can also provide the shortest path for the distal tip 1243 to reach the desired depth within target tissue.

In some embodiments, the housing 1210 and/or the adjustment member 1250 can include a mechanism to limit and/or prevent proximal movement of the distal tip 1243. Said another way, in some embodiments, the housing 1210 and/or the adjustment member 1250 can include a mechanism to prevent transition of the adjustment member (either distally towards the second configuration, or proximally towards a configuration that is further proximal from the first configuration). For example, in some embodiments, the housing 1210 can include a shoulder (not shown) that engages a corresponding shoulder (not shown) of the adjustment member 1250 to prevent proximal movement of the distal tip 1243. In this manner, the proximal force exerted by the target tissue T on the distal end surface 1245 during initial insertion does not reduce the effective length to an amount less than the distance $D_1$. Thus, the effective length of the puncture member is maintained at the distance $D_1$ during the initial insertion operation.

The injector assembly 1001 can be moved distally to complete the initial insertion operation in any suitable manner. For example, in some embodiments, the user can manually apply a force to a portion of the medicament container 1130 and/or the housing 1210. Said another way, the initial insertion operation can be a manual operation that does not rely on any stored energy device (e.g., springs, compressed gas containers, or the like) to produce the force to move the medicament container 1130 and/or the housing 1250.

After the initial insertion operation, a portion of the medicament from within the medicament container 1130 can then be conveyed from the volume 1133 of the medicament container 1130 into the first chamber 1221, as shown by the arrow BB in FIG. 7. Specifically, the medicament within the volume 1133 can be pressurized (e.g., shown by the pressure $P_1$), and the medicament within the first chamber 1221 can be pressurized (e.g., shown by the pressure P2). By pressurizing the first chamber 1221, the forces acting on the adjustment member 1250 and the puncture member 1240 can, under certain circumstances, become unbalanced, causing the adjustment member 1250 to transition from its first configuration (FIG. 6) to its second configuration (FIG. 7). Similarly stated, the puncture member 1240 and the adjustment member 1250 are collectively configured such that the adjustment member 1250 can move within the housing 1210 from its first configuration (or position) towards its second configuration (or position) when the pressure $P_2$ within the first chamber 1221 is greater than a threshold pressure.

Figure 8:
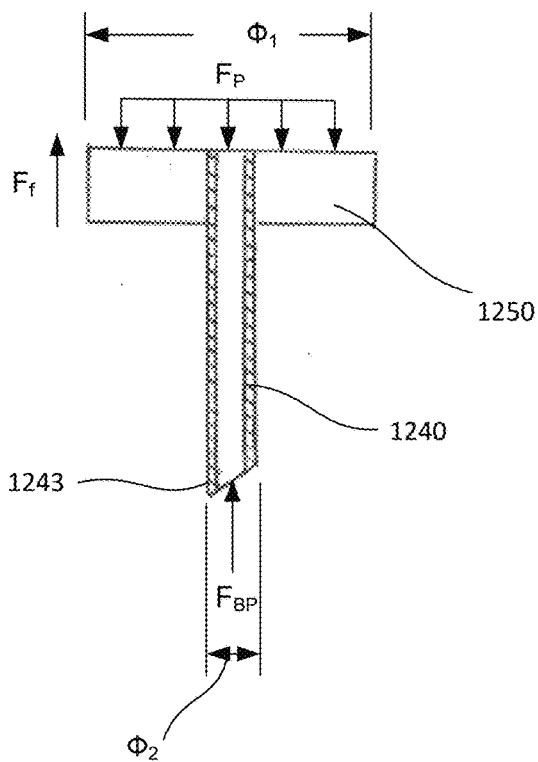
FIG. 8 is a schematic illustration of an adjustment member of the injector assembly shown in FIG. 5, showing forces applied to the adjustment member during use.

Referring to FIG. 8, after the first chamber 1221 is pressurized, the primary forces acting on the adjustment member 1250 include the pressure force $F_P$, the friction force $F_f$, and the tissue back-pressure force $F_{BP}$. The pressure force $F_P$ is produced by the pressurized medicament in the first chamber 1221, and acts in a distal direction on a proximal surface of the adjustment member 1250, as shown by the arrows $F_P$. The magnitude of the pressure force $F_P$ can be influenced by, among other things, the magnitude of the pressure $P_2$ and the area or diameter $\Phi_1$ of the proximal surface. The friction force $F_P$ is the force opposing motion between the portions of the adjustment member 1250 that are in contact with the inner surface of the housing 1210. The magnitude of the friction force can be influenced by the static coefficient of friction (also referred to as "sticktion force") and the kinetic coefficient of friction between the mating pieces, as well as the area of contact. The tissue back-pressure force $F_{BP}$ is the force exerted by the target tissue T on both the distal end surface 1245 and the medicament present at the distal end surface 1245. Specifically, the target tissue T must deform and/or otherwise "make room" for both movement of the distal end surface and any bolus of medicament exiting the distal end surface 1245. Thus, the resistance of the tissue to deform exerts an opposing force on the distal end surface 1245 and the medicament. The tissue back-pressure force $F_{BP}$ is influenced by the area (or diameter $\Phi_2$) of the distal end surface 1245, the properties of the target tissue T within which the distal tip 1243 is disposed, and the properties of the medicament. Specifically, target tissue T having a low density and/or a high porosity results in a lower tissue back-pressure force $F_{BP}$ than that which is produced within tissue having a high density and/or a low porosity. Similarly, a highly viscous medicament results a higher back-pressure force $F_{BP}$ than that which is produced in connection with a less viscous medicament.

Thus, when the pressure force $F_P$ is greater than the sum of the friction force $F_f$ and the tissue back-pressure force $F_{BP}$, the adjustment member 1250 transitions from its first configuration (FIG. 6) towards its second configuration (FIG. 7). When the pressure $P_2$ is reduced such that the pressure force $F_P$ is less than the sum of the friction force $F_f$ and the tissue back-pressure force $F_{BP}$, however, the transition of the adjustment member 1250 stops. Thus, depending on the region of tissue (e.g., the first region R1 or the second region R2) within which the distal tip 1243 is disposed and the pressure $P_2$ applied within the first chamber 1221, the adjustment member 1250 can transition between the first configuration, the second configuration, and an infinite number of configurations therebetween. This, in turn, causes the distal tip 1243 to move distally within the target tissue. The additional insertion of the distal tip 1243 when the adjustment member 1250 is transitioned towards its second configuration (or position) is referred to as the secondary insertion operation.

The pressure force $F_P$ also acts to produce a flow of the medicament from the first chamber 1221 through the puncture member 1240, and into the target tissue T. To produce a flow of the medicament, the pressure $P_2$ must be sufficient to overcome both the internal resistance (or friction loss) through the puncture member and the tissue back-pressure force $F_{BP}$, discussed above. In certain circumstances, the pressure $P_2$ of the medicament within the first chamber 1221 can be modeled by the Hagen-Poiseuille law, as indicated below:

$$P_2 = (8 * \mu * L * Q)/(\Pi * R^4) \qquad (1)$$

where $P_2$ is the pressure of the medicament within the first chamber 1221, $\mu$, is the viscosity of the medicament, L is the length of the puncture member 1240, Q is the flow rate of the medicament through the puncture member 1240, and R is the radius of the lumen defined by the puncture member 1240. Because the pressure (and/or force) required to inject a high viscosity fluid through a small-bore the puncture member 1240 is proportional to the inverse of the radius of the lumen of the needle to the fourth power, the pressure of the medicament within the medicament container necessary to achieve the desired flow rate can, at times, be relatively high.

In some embodiments, puncture member 1240 and the adjustment member 1250 are collectively configured such that the adjustment member 1250 transitions from the first configuration towards the second configuration when the pressure $P_2$ within the first chamber 1221 is greater than the threshold pressure. Additionally, the puncture member 1240 is configured such that the substance is maintained within the first chamber 1221 when: A) the distal tip 1243 of the puncture member 1240 is within a region (e.g., the first region R1) of the target tissue having a density greater than a threshold density, and B) the pressure $P_2$ within the first chamber 1221 is greater than the threshold pressure. Similarly stated, in some embodiments, when the distal tip 1243 is within a region of tissue having a higher density and/or lower porosity and when the pressure $P_2$ is greater than a threshold pressure, the balance of forces acting on the adjustment member 1250 and the puncture member 1240 can be such that the adjustment member 1250 transitions towards its second configuration, but a flow of medicament through the puncture member 1240 is prevented. In this manner, even though the medicament is pressurized, the distal tip 1243 can move distally (i.e., the secondary insertion) without the medicament flowing out of the puncture member 1240. Said another way, in some embodiments, the injector assembly 1001 can be actuated to pressurize the first chamber 1221 at a pressure that is sufficient to move the distal tip 1243 within the target tissue, while maintaining the medicament within the first chamber 1221 and/or puncture member 1240.

This arrangement can facilitate injection of the drug within a specific region of the target tissue, such as, for example, the SCS. For example, in some embodiments, the first region R1 of the target location T can have a first density and the second region R2 can have a second density, which is lower than the first density. Thus, the first region R1 of the target location T produces a first tissue back-pressure ($F_{BP}$) on the distal end surface 1245, and the second region R2 produces a second tissue back-pressure ($F_{BP}$) on the distal end surface 1245, which is lower than the first tissue back-pressure. In other words, the first region R1 of the target location T produces a first pressure that resists and/or opposes flow from the puncture member 1240, and the second region R2 produces a second pressure that resists and/or opposes flow from the puncture member 1240, which is less than the first pressure. In some embodiments, the target location T can be an eye, the first region R1 is a sclera of the eye, and the second region R2 is a suprachoroidal space of the eye. After the initial insertion (see, e.g., FIG. 6), the medicament within the container 1130 is pressurized. As described above, the pressure $P_2$ can be such that the adjustment member 1250 transitions towards the second configuration, thereby moving the distal tip 1243 further into the target tissue (see, e.g., FIG. 7 showing the secondary insertion). Moreover, because the first region R1 (e.g., the sclera) has a higher density, the pressure $P_2$ is insufficient to cause the medicament to flow out of the puncture member 1240. This is shown graphically in FIG. 9, which is a conceptual plot showing both the pressure P2 and the flow rate of the medicament Q as a function of the position of the distal tip 1243. As shown, the pressure $P_2$ initially increases to overcome the static friction (or "sticktion") of the stationary adjustment member 1250. Then, while the distal tip moves within the first region R2, the pressure $P_2$ remains substantially constant. The medicament is maintained within the first chamber 1221, and thus the flow rate Q is substantially zero.

Figure 9:
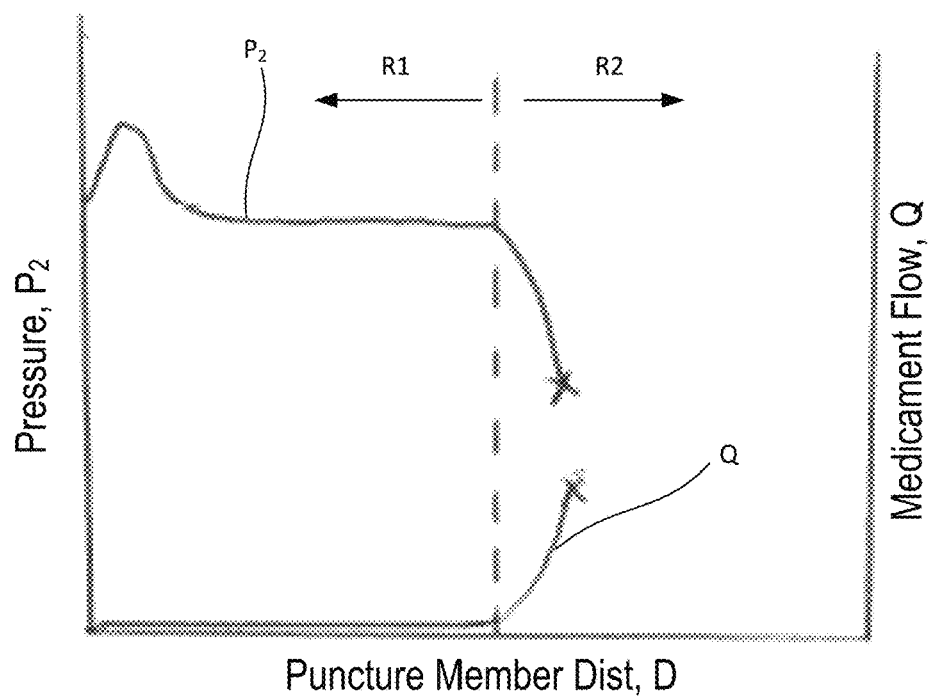
FIG. 9 is a graph showing the variation in pressure within the injector assembly and the flow of medicament from the injector assembly as a function of the position of the puncture member.

When the distal tip 1243 advances through the first region R1 (e.g., the sclera) and into the SCS (or the region at which the SCS will be produced), the density of the target tissue decreases, and the tissue back-pressure ($F_{BP}$) on the distal end surface 1245 also decreases. Accordingly, the lower tissue back-pressure allows the medicament to flow from the first chamber 1221 and through the puncture member 1240. This is shown in FIG. 9 by the increase in the flow rate Q after the distal tip 1243 reaches the second region R2 (e.g., the SCS). The flow of the medicament also causes the pressure $P_2$ within the first chamber 1221 to decrease, thereby slowing and/or stopping the transition (or movement) of the adjustment member 1250. This is shown in FIG. 9 by the decrease in the pressure $P_2$ after the distal tip 1243 reaches the second region R2 (e.g., the SCS). Thus, when the distal tip 1243 reaches the second region R2, movement of the distal tip 1243 slows or stops, and the medicament flows into the second region (as indicated by the arrow CC in FIG. 7). Although the second region R2 is described as the SCS, in other embodiments, the second region R2 can include at least one of a suprachoroidal space, a lower portion of the sclera, a choroid of the eye, a subretinal space of the eye, or a retina of the eye.

The pressure $P_1$ within the medicament container 1130 and/or the pressure $P_2$ within the first chamber 1221 can be produced in any manner. For example, in some embodiments, the pressure $P_1$ and/or the pressure $P_2$ can be produced by moving an actuation rod (not shown) within the medicament container 1130. Similarly stated, in some embodiments, the pressure $P_1$ and/or the pressure $P_2$ can be produced in response to a force exerted on a proximal end portion of an actuation rod. In some such embodiments, the force can have magnitude of less than about 6N, which is a force threshold above which users generally do not like to apply to the eye during ocular injection.

As shown in FIGS. 5-7, when the adjustment member 1250 transitions from the first configuration to the second configuration, the adjustment member 1250 moves within the housing 1210 and relative to the housing 1210 and the medicament container 1130. Thus, when the adjustment member 1250 transitions from the first configuration to the second configuration, the puncture member 1240 also moves relative to the housing 1210 and the medicament container 1130. In this manner, the movement of the distal tip 1243 from its first effective length (e.g., the distance $D_1$) to its second effective length (e.g., the distance $D_2$) occurs when the housing 1210 (including the hub surface 1228) and the medicament container 1130 are in a fixed position relative to the target surface S. This arrangement improves the precision of the second insertion operation, and also allows the hub surface 1228 to remain in firm contact with the target surface S.

Figure 11:
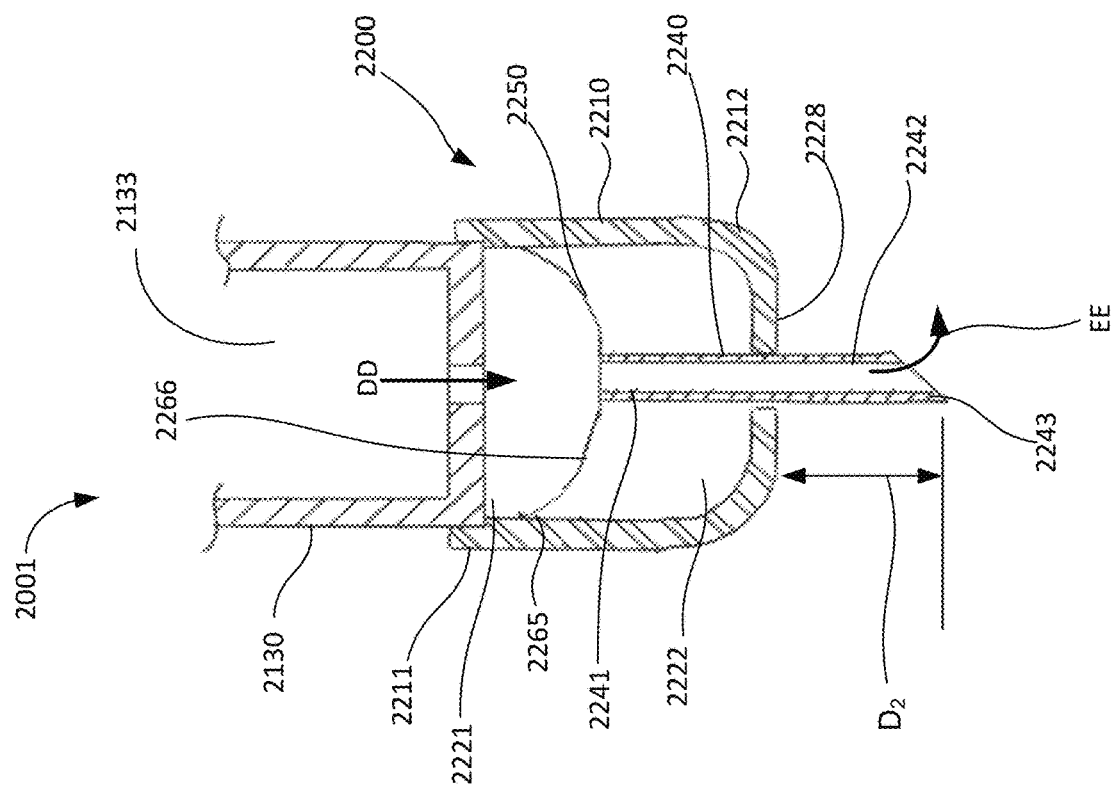
FIGS. 10 and 11 are schematic illustrations of an injector assembly according to an embodiment, in a first configuration and a second configuration, respectively.
Figure 10:
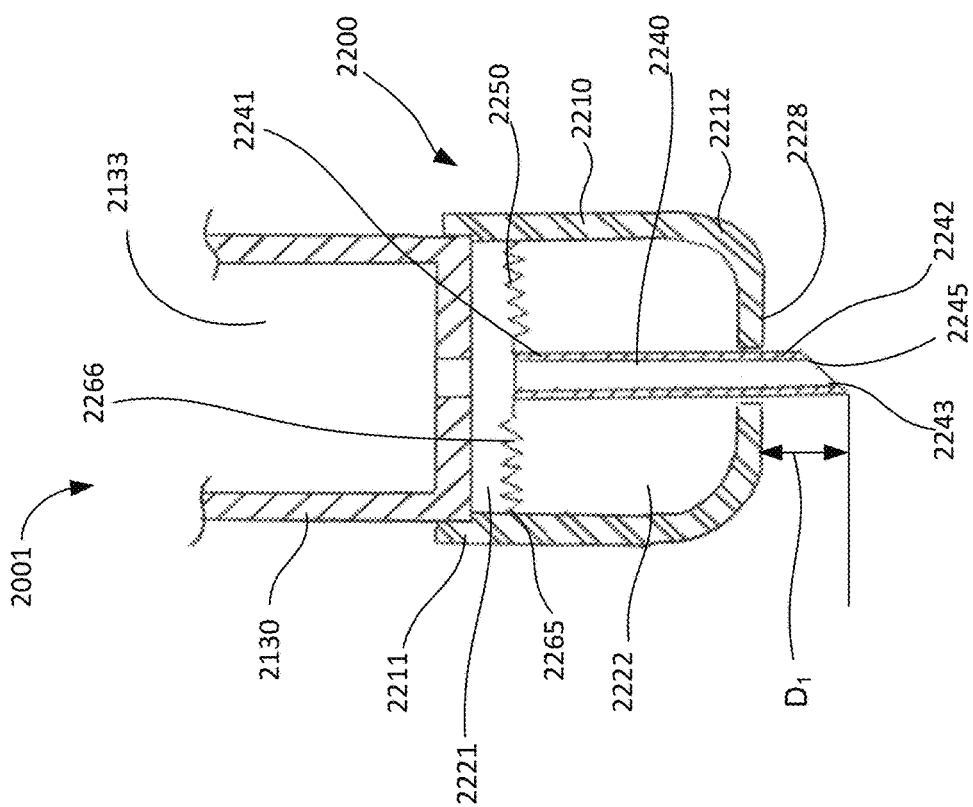

Although the adjustment member 1250 is shown as moving linearly within the housing 1210 from a first position to a second position when the adjustment member 1250 transitions from the first configuration to the second configuration, in other embodiments, an injection assembly can include an adjustment member that does not move linearly when transitioning. For example, in some embodiments, an injection assembly can include an adjustment member that rotates when transitioning from a first configuration to a second configuration. In other embodiments, an injection assembly can include an adjustment member that deforms (e.g., expands) when transitioning from a first configuration to a second configuration. For example, FIGS. 10 and 11 are schematic illustrations of an injector assembly 2001 according to an embodiment. The injector assembly 2001 includes a medicament container 2130, a housing 2210, an adjustment member 2250, and a puncture member 2240.

The housing 2210 includes a proximal end portion 2211 and a distal end portion 2212. The proximal end portion 2211 can be coupled to the medicament container 2130. The medicament container 2130 can be any suitable container that defines a reservoir or volume 2133 within which a drug (also referred to as a medicament) can be contained. For example, in some embodiments, the medicament container 2130 can be a syringe that includes an actuation rod (not shown in FIGS. 10 and 11) within the volume 2133. In such embodiments, the actuation rod can be reciprocated within the volume 2133 to either produce a vacuum within the medicament container 2130 (e.g., to draw a medicament into the volume 2133) or produce a pressure within the medicament container 2130 (e.g., to expel the medicament from the volume 2133). In some embodiments, the medicament container 2130 can be a prefilled (or prefillable) syringe, that includes one or more doses of any suitable substance (the medicament or drug) within the volume 2133. For example, in some embodiments, the medicament container contains at least one of a VEGF, a VEGF inhibitor, a PDGFR inhibitor, or a combination of any of the VEGF, the VEGF inhibitor, and the PDGFR inhibitor.

The proximal end portion 2211 of the housing 2210 can be coupled to the medicament container 2130 in any suitable manner. For example, in some embodiments, the housing 2210 can be removably coupled to the medicament container 2130, for example, by a Luer connector, a threaded joint, a snap-fit, a latch, a friction (or press-on) fit, or any other suitable coupling features. In this manner, the housing 2210 (and therefore the puncture member 2240) can be removed from the medicament container 2130 to allow a vial or other container to be coupled to the medicament container (e.g., to allow a dose of drug to be conveyed into the volume 2133). In some embodiments, the injector assembly 2001 (or any of the injector assemblies described herein) can be included in any of the kits shown and described in U.S. patent application Ser. No. 15/427,823, entitled "Ocular Injection Kit, Packaging, and Methods of Use," Filed Feb. 8, 2017, which is incorporated by reference herein in its entirety. In other embodiments, the housing 2210 can be permanently coupled to the medicament container 2130. Similarly stated, in some embodiments, the housing 2210 can be coupled to the medicament container 2130 in a manner that precludes removal of the housing 2210 from the medicament container 2130 during the intended (or "normal") use of the injector assembly 2001. In such embodiments, the housing 2210 can be permanently coupled to the medicament container 2130 by a weld joint, an adhesive, a bond, or the like. In yet other embodiments, the housing 2210 and the medicament container 2130 can be monolithically constructed.

The distal end portion 2212 of the housing 2210 includes a hub surface 2228, which is a contact surface having any suitable shape and/or size configured to contact a target surface of a target tissue during an injection operation (the target tissue is not shown in FIGS. 10 and 11, but can be similar to the target tissue shown in FIGS. 6 and 7). For example, in some embodiments, the hub surface 2228 is configured to deform the target surface (e.g., the conjunctiva of the eye) when the distal end portion 2212 is brought into contact with the target surface. In some embodiments, the hub surface 2228 can have a substantially convex shape, for example, a hemispherical shape, and can define a sealing portion that forms a substantially fluid-tight seal with the target surface when the distal end portion 2212 is brought into contact with the target surface S. For example, in some embodiments, the hub surface 2228 can deform the target surface to produce a substantially fluid-tight seal between the housing 2210 and the target surface. In some embodiments, the hub surface 2229 can include any of the characteristics of any of the hubs or hub surfaces shown and described in U.S. Pat. No. 9,180,047, entitled "Apparatus and Methods for Ocular Injection," which is incorporated herein by reference in its entirety.

The adjustment member 2250 is disposed within an inner volume defined by the housing 2210, and separates the inner volume into a first chamber 2221 (also referred to as a pressure chamber) and a second chamber 2222. As shown, the first chamber 2221 is in fluid communication with the medicament container 2130 (and/or the volume 2133) when the housing 2210 is coupled to the medicament container 2130. In this manner, as described herein, a medicament from the medicament container 2130 can be conveyed into the first chamber 2221. Moreover, the medicament within the first chamber 2221 can be pressurized to transition the adjustment member between a first configuration (FIG. 10) and a second configuration (FIG. 11). Transitioning the adjustment member 2250 produces movement of the puncture member 2240, as described below.

As shown, the adjustment member 2250 includes an edge 2265 and an expandable portion 2266. The edge 2265 is fixedly coupled to an inner surface of the housing 2210 to fluidically isolate the first (or pressure) chamber 2221 from the second chamber 2222. The edge 2265 can be fixed to the inner surface of the housing 2210 in any suitable manner. For example, in some embodiments, the edge 2265 can be coupled within the housing 2210 by an adhesive, by a plastic weld, by a thermal bonding process, or the like. The expandable portion 2266 is constructed from a material that expands to transition the adjustment member from its first configuration to its second configuration when the first (pressure) chamber 2221 is pressurized (see FIG. 11). In some embodiments, the expandable portion 2266 can be constructed from a compliant material, such as an elastomer (e.g., polyurethane, Nylon elastomers, thermoplastic elastomers, or the like), that stretches or elastically deforms when the pressure within the first chamber 2211 is increased. In other embodiments, the expandable portion 2266 can be constructed from a substantially non-compliant material, such as polyethylene terephthalate (PET). By using a non-compliant expandable portion, the overall shape of the adjustment member 2250 can be maintained relatively independent of the pressure within the first chamber 2211.

The puncture member 2240 can be any suitable device to puncture the target surface and define a passageway within the target tissue (not shown in FIGS. 10 and 11). The puncture member 2240 also provides a lumen through which the medicament can be delivered into the target tissue (shown by the arrow EE in FIG. 11). As shown, the puncture member 2240 includes a proximal end portion 2241 and a distal end portion 2242, and defines a lumen through which the medicament can be conveyed from the medicament container 2130 and/or the first chamber 2221 (shown by the arrow DD in FIG. 11). The puncture member 2240 is coupled to the adjustment member 2250 such that the proximal end portion 2241 is in fluid communication with the first chamber 2221. In this manner, a substance (e.g., a drug or medicament) can be conveyed from the medicament container 2130 through the puncture member 2240 via the first chamber 2221. The distal end portion 2242 of the puncture member 2240 includes a distal end surface 2245 that is beveled or a sharpened to facilitate puncturing the target tissue. The distal end surface 2245 can have any suitable shape, size and/or geometry (e.g., bevel angle, bevel height, bevel aspect ratio or the like).

The distal end surface 2245 includes a distal tip 2243. Similarly stated, the distal tip 2243 is formed by the intersection of the distal end surface 2245 and an outer side wall of the puncture member 2240. Referring to FIG. 10, the distal tip 2243 of the puncture member extends from the hub surface 2228 by a first distance $D_1$ when the adjustment member 2250 is in the first configuration. Referring to FIG. 11, the distal tip 2243 of the puncture member extends from the hub surface 2228 by a second distance $D_2$ when the adjustment member 2250 is in the second configuration. In this manner, the position of the puncture member 2240 relative to the hub surface 2228 (i.e., the effective length) can change during an injection operation to ensure that the distal tip 2243 (and therefore the opening in the beveled distal end surface 2245) is placed within the desired region of (or at the desired depth within) the target tissue during medicament delivery. Moreover, as described herein, the position of the distal tip 2243 relative to the hub surface 2228 is changed automatically and in an infinite number of positions (within a predefined range). Said another way, the position of the distal tip 2243 relative to the hub surface 2228 is changed in response to the user actuating the device without any additional input from the user. Thus, the user need not separately manipulate any needle adjustment features, and need not monitor the actual depth of the distal tip 2243 within the target tissue.

The operation of the injector assembly 2001 is similar in many respects to the operation of the injector assembly 1001 as described above, and is therefore not described in detail below. For example, the initial insertion operation of the injector assembly 2001 is similar to that described above for use of the injector assembly 2001. Specifically, in some embodiments, the initial insertion operation can include inserting the distal tip 2243 until hub surface 2228 contacts the target surface. Thus, the insertion depth of the puncture member 2240 after the initial insertion is the same as the effective length of the puncture member 2240 (which is the distance $D_1$). Moreover, as with the injector assembly 1001, in some embodiments, the injector assembly 2001 can include a mechanism to limit and/or prevent proximal movement of the distal tip 2243. Said another way, in some embodiments, the housing 2210 and/or the adjustment member 2250 can include a mechanism to prevent transition of the adjustment member (either distally towards the second configuration, or proximally towards a configuration that is further proximal from the first configuration).

After the initial insertion operation, a portion of the medicament from within the medicament container 2130 can then be conveyed from the volume 2133 of the medicament container 2130 into the first chamber 2221, as shown by the arrow DD in FIG. 11. Specifically, the medicament within the volume 2133 can be pressurized, which, in turn, pressurizes the medicament within the first chamber 2221. By pressurizing the first chamber 2221, the forces acting on the adjustment member 2250 (including the expandable portion 2266) and the puncture member 2240 can, under certain circumstances, cause the adjustment member 2250 to transition from its first configuration (FIG. 10) to its second configuration (FIG. 11). Similarly stated, the puncture member 2240 and the adjustment member 2250 are collectively configured such that the adjustment member 2250 can transition within the housing 2210 from its first configuration (or position) towards its second configuration (or position) when the pressure $P_2$ within the first chamber 2221 is greater than a threshold pressure.

After the first chamber 2221 is pressurized, the primary forces acting on the adjustment member 2250 include the pressure force (similar to the pressure force $F_P$ described with reference to FIG. 8) and the tissue back-pressure force (similar to the back-pressure force $F_{BP}$ described with reference to FIG. 8). The pressure force is produced by the pressurized medicament in the first chamber 2221, and acts in a distal direction on a proximal surface of the adjustment member 2250. Because the adjustment member 2250 is fixedly coupled to the inner surface of the housing 2210, there is no friction force acting to resist the distal movement of the adjustment member 2250. Instead, the material properties of the adjustment member 2250, including the expandable portion 2266 resist the transition (or expansion) of the adjustment member 2250. As described above, the tissue back-pressure force is the force exerted by the target tissue on both the distal end surface 2245 and the medicament present at the distal end surface 2245.

Thus, when the pressure force is greater than the sum of the internal forces produced by the adjustment member and the tissue back-pressure force, the adjustment member 2250 transitions from its first configuration (FIG. 10) towards its second configuration (FIG. 11). When the pressure within the pressure chamber 2221 is reduced such that the pressure force is less than the sum of the internal force and the tissue back-pressure force, however, the transition of the adjustment member 2250 stops. Thus, depending on the region of tissue within which the distal tip 2243 is disposed and the pressure applied within the first chamber 2221, the adjustment member 2250 can transition between the first configuration, the second configuration, and an infinite number of configurations therebetween. This, in turn, causes the distal tip 2243 to move distally within the target tissue during a secondary insertion operation.

In some embodiments, puncture member 2240 and the adjustment member 2250 are collectively configured such that the adjustment member 2250 transitions from the first configuration towards the second configuration when the pressure within the first chamber 2221 is greater than a threshold pressure. Additionally, the puncture member 2240 is configured such that the substance is maintained within the first chamber 2221 when: A) the distal tip 2243 of the puncture member 2240 is within a region (e.g., a sclera) of the target tissue having a density greater than a threshold density, and B) the pressure $P_2$ within the first chamber 2221 is greater than the threshold pressure. Similarly stated, in some embodiments, when the distal tip 2243 is within a region of tissue having a higher density and/or lower porosity and when the pressure within the pressure chamber 2221 is greater than a threshold pressure, the balance of forces acting on the adjustment member 2250 and the puncture member 2240 can be such that the adjustment member 2250 transitions towards its second configuration, but a flow of medicament through the puncture member 2240 is prevented. In this manner, even though the medicament is pressurized, the distal tip 2243 can move distally (i.e., the secondary insertion) without the medicament flowing out of the puncture member 2240. Said another way, in some embodiments, the injector assembly 2001 can be actuated to pressurize the first chamber 2221 at a pressure that is sufficient to move the distal tip 2243 within the target tissue, while maintaining the medicament within the first chamber 2221 and/or puncture member 2240. This arrangement can facilitate injection of the drug within a specific region of the target tissue, such as, for example, the SCS, as described above.

Any of the needle assemblies described herein (e.g., the needle assembly that includes the housing 1210, the puncture member 1240, and the adjustment member 1250 or the needle assembly that includes the housing 2210, the puncture member 2240, and the adjustment member 2250) can be included with any suitable injector assembly and can be used to perform any of the methods described herein. For example, in some embodiments, any of the needle assemblies described herein can be used with any of the injector assemblies (or to perform any of the methods) described in International Patent Application No. WO2015/195842, entitled "METHODS AND DEVICES FOR TREATING POSTERIOR OCULAR DISORDERS" and U.S. Pat. No. 9,180,047, entitled "APPARATUS AND METHODS FOR OCULAR INJECTION," each of which is incorporated herein by reference in its entirety.

FIGS. 12-20 show an injector assembly 3001 according to an embodiment that can be configured for non-surgical use, and can provide for precise control of the depth of insertion of a microneedle into a target tissue. As described, the microneedle 3240 can move, relative to the hub housing 3210 and/or the medicament container 3130, during the insertion/injection operation such that the tip of the microneedle can be placed in the desired position within the target tissue. Such placement can allow the drug formulation to flow into the desired portion of the target tissue. Specifically, the injector assembly 3001 includes a handle 3110, a medicament container (also referred to as a barrel) 3130, an actuation rod 3120, and a needle assembly 3200 (also referred to as a hub or hub assembly).

Figure 14:
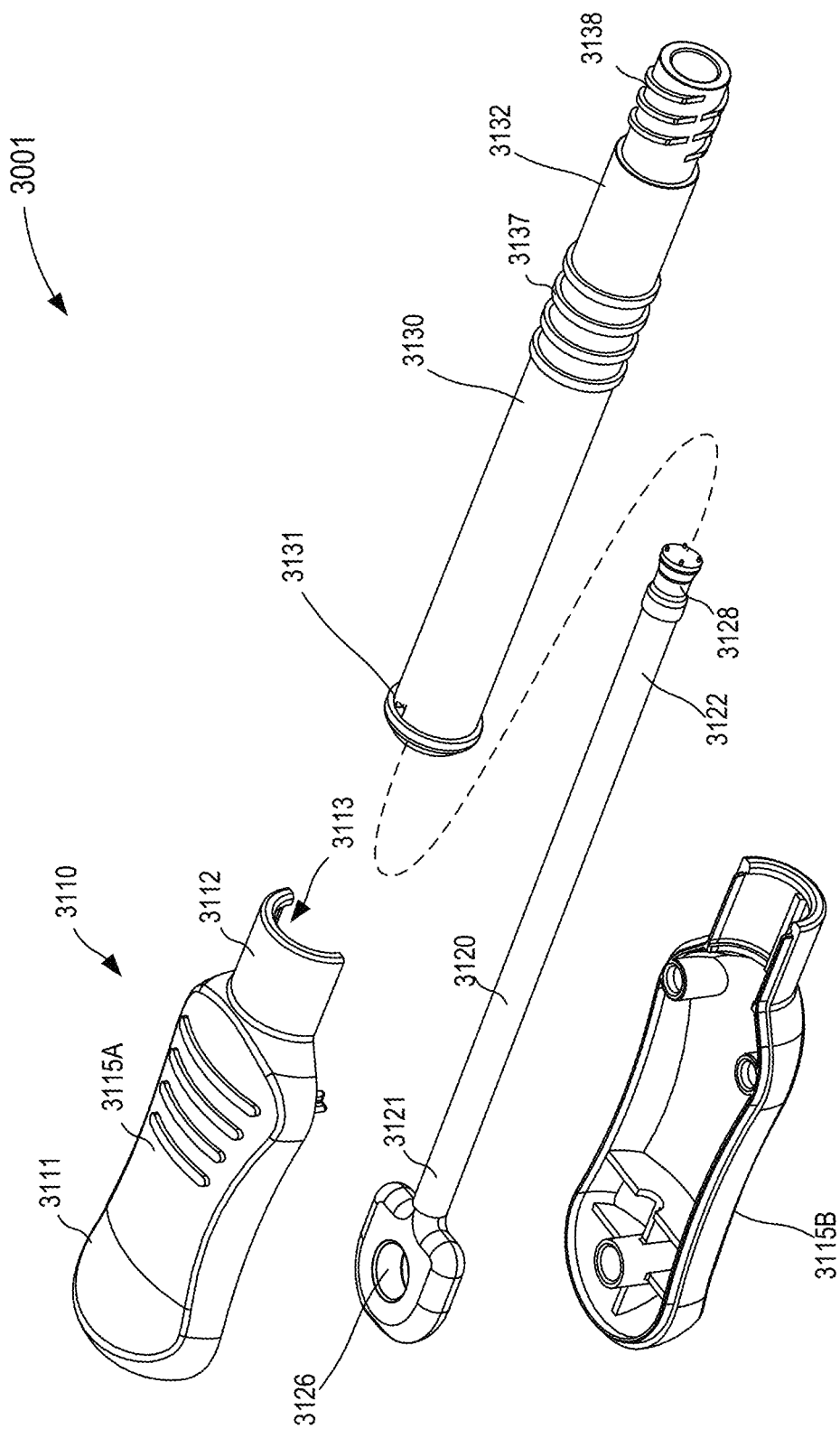
FIG. 14 is an exploded view of a portion of the injector assembly shown in FIGS. 12 and 13.
Figure 15:
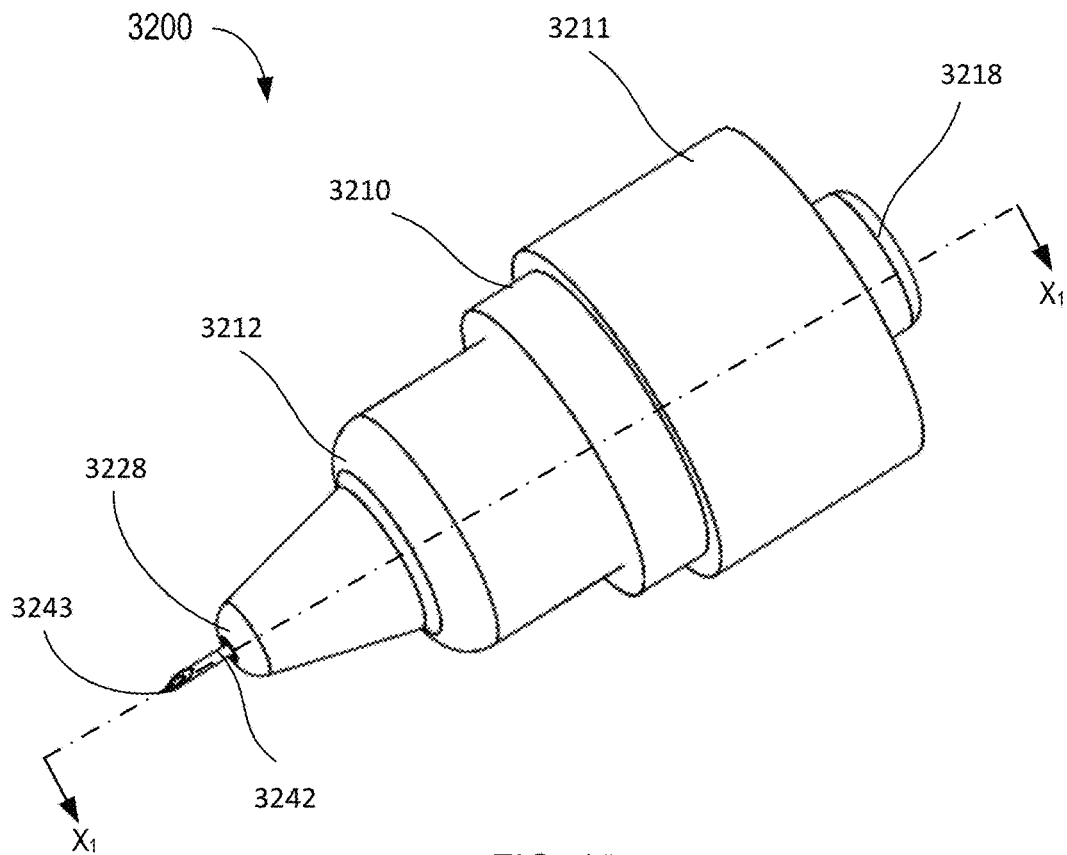
FIGS. 15 and 16 are perspective views of a needle assembly of the injector assembly shown in FIGS. 12 and 13.
Figure 16:
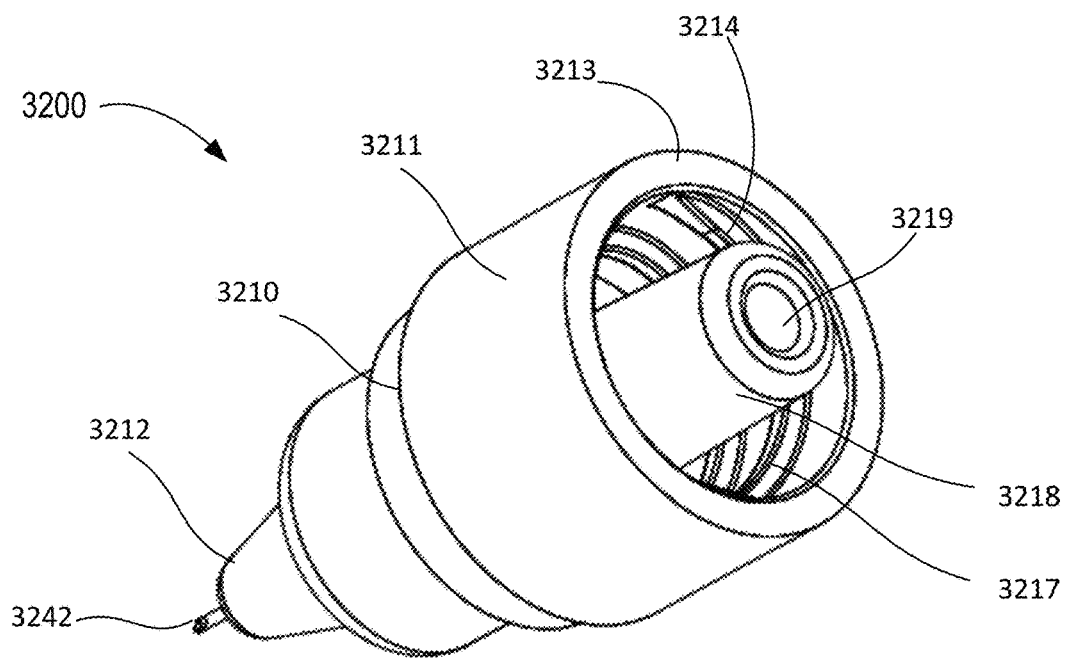

The handle 3110 can be any suitable shape, size, and/or configuration. For example, in some embodiments, the handle 3110 can have an ergonomic shape and/or size, which can enable a user to manipulate the injector 3100 with one hand or with two hands. The handle 3110 has a proximal end portion 3111 and a distal end portion 3112, and defines an inner volume 3113 that receives and/or is configured to house at least a portion of the barrel 3130 and the actuation rod 3120. As shown in FIG. 14, the handle 110 is formed by coupling a first handle member 3115A to a second handle member 3115B. The handle member 3115A and the handle member 3115B can be relatively thin shelled or the like, and can be formed from any suitable material such as the biocompatible materials described herein. In other words, the handle members 3115A and 3115B can be substantially hollow and/or can define the inner volume 3113.

The actuation rod 3120 is configured to be moved within the medicament container 3130 to either produce a vacuum (to draw a dose of medicament into the medicament container 3130) or to produce to a positive pressure (to deliver the dose of medicament out of the medicament container 3130). Referring to FIG. 14, the actuation rod 3120 includes a proximal end portion 3121 and a distal end portion 3122. The proximal end portion 3121 is configured to be disposed within the inner volume 3113 of the handle 3110, and includes an engagement portion 3126. The engagement portion 3126 defines an opening through which a retention member (not shown) of the handle member 3115A is disposed to fixedly couple the actuation rod 3120 to the handle 3110. In this manner, movement of the handle 3110 relative to the medicament container 3130 and/or the needle assembly 3200 results in movement of the actuation rod 3120 relative to and/or within the medicament container 3130.

The distal end portion 3122 of the actuation rod 3120 includes and/or is coupled to an elastomeric member 3128. In some embodiments, the elastomeric member 3128 can be monolithically formed with the actuation rod 3120 (e.g., overmolded or the like). In other embodiments, the elastomeric member 3128 can be formed independently of the actuation rod 3120 and coupled thereto. The elastomeric member 3128 can be constructed from an inert and/or biocompatible material, which can have any suitable hardness and/or durometer. For example, in some embodiments, the elastomeric member 3128 can be formed from and/or constructed out of a rubber, silicone, plastic, nylon, polymers, any other suitable material or combination thereof. The distal end portion 3122 of the actuation rod 3120 is disposed in the medicament container 3130 such that a surface of the elastomeric member 218 is in contact with an inner surface of the medicament container 3130. In some embodiments, the elastomeric member 3128 and the inner surface of the medicament container 3130 collectively form a substantially fluid-tight seal and/or a hermetic seal, which can prevent leakage, out gassing, contamination, and/or the like of a substance (e.g., a medicament) disposed within the medicament container 3130. In this manner, movement of the handle 3110 relative to the medicament container 3130 causes the actuation rod 3120 (and thus, the elastomeric member 3128) to move within the medicament container 3130 either to produce a vacuum (to draw a dose of medicament into the barrel) or to produce to a positive pressure (to deliver the dose of medicament out of the barrel).

Figure 12:
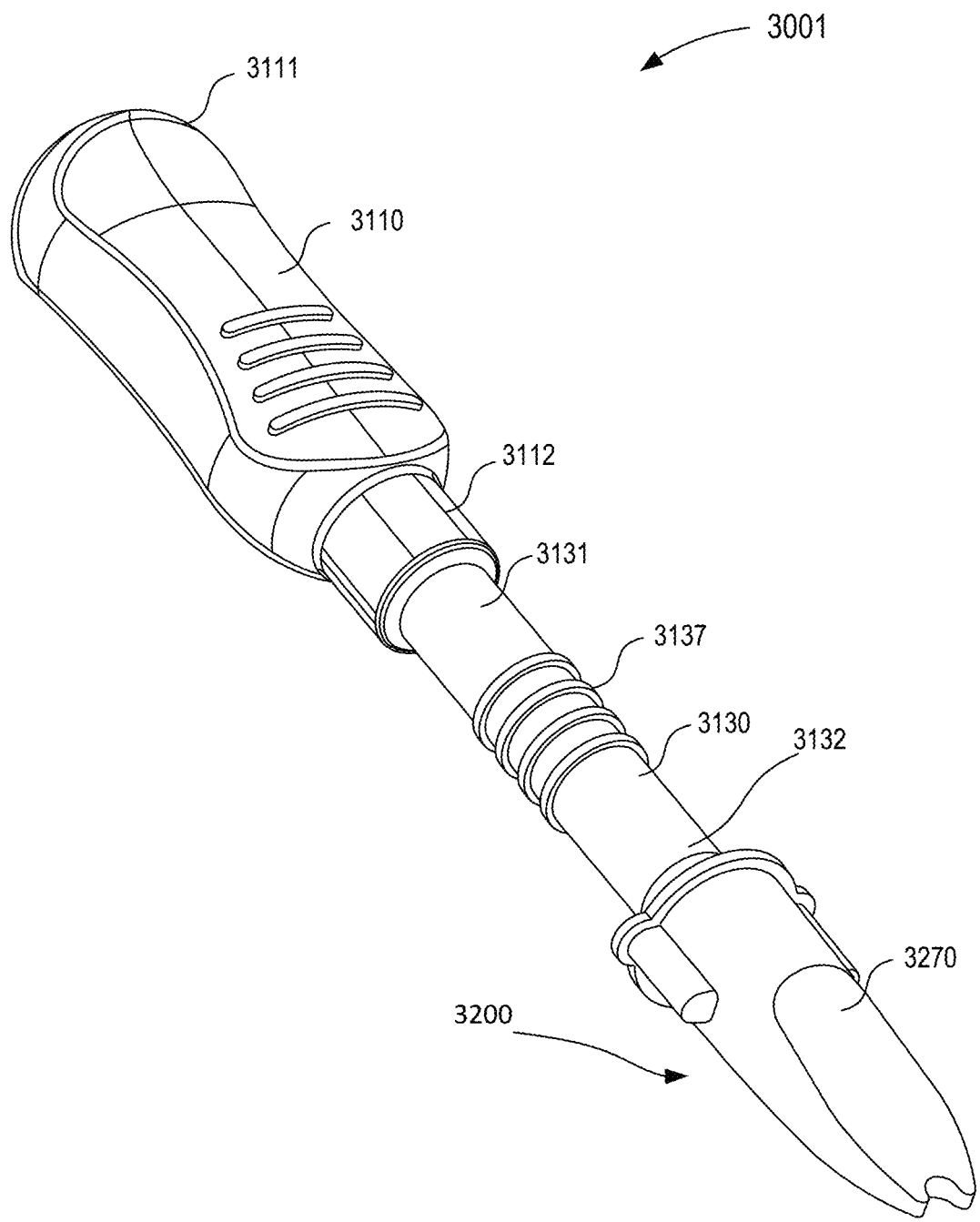
FIGS. 12 and 13 are perspective views of an injector assembly according to an embodiment.
Figure 13:
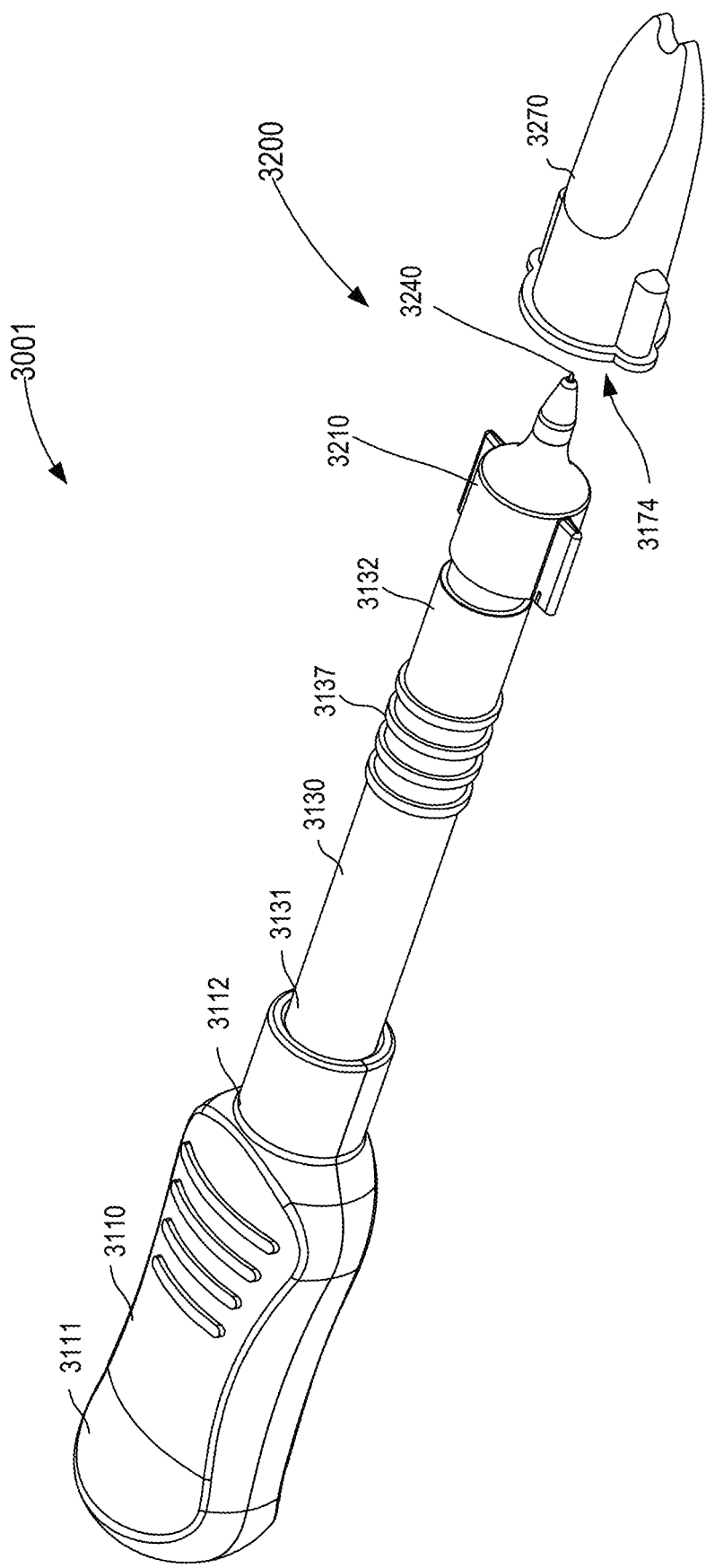

The medicament container (or barrel) 3130 of the injector 3100 can be any suitable shape, size, or configuration. As shown in FIGS. 12-14, the barrel 3130 has a proximal end portion 3131 and a distal end portion 3132, and defines a lumen therethrough. The barrel 3130 has an outer surface that includes a grip portion 3137. The grip portion 3137 can facilitate the use of the medical injector 3001 by providing a user with a predetermined location at which to engage the injector 3001. The grip portion 3137 can have any suitable surface finish or the like, which can, in some instances, increase a friction between the grip portion 3137 and a user's fingers and/or hand. In other embodiments, the barrel 3130 does not include a grip portion.

As described above, the barrel 3130 movably receives at least the distal end portion 3122 of the actuation rod 3120, and defines a medicament volume configured to receive, store, house, and/or otherwise contain a medicament (e.g., a corticosteroid such as triamcinolone acetonide, or any other medicament described herein). For example, in some embodiments, the medicament container 3130 contains at least one of a VEGF, a VEGF inhibitor, a PDGFR inhibitor, or a combination of any of the VEGF, the VEGF inhibitor, and the PDGFR inhibitor. In some embodiments, at least a portion of the barrel 3130 can be substantially transparent and/or can include an indicator or the like configured to allow a user to visually inspect a volume of fluid (e.g., medicament/therapeutic formulation) therein. In some instances, such an indicator can be, for example, any number of lines and/or markings associated with a volume of fluid disposed within the barrel 3130. In other embodiments, the barrel 3130 can be substantially opaque and/or does not include an indicator or the like.

The proximal end portion 3131 of the barrel 3130 includes a flanged end that is disposed within the inner volume 3113 of the handle 3110. Specifically, at least the proximal end portion 3131 of the barrel 3130 can be inserted into the handle 3110 in such a manner that the handle 3110 can be moved relative to the barrel 3130. In other words, at least the proximal end portion 3131 of the barrel 3130 is movably disposed within the inner volume defined by the handle 3110. In this manner, during the injection operation, substantially all of the force applied by the user to the handle 3110 will urge the handle 3110 (and therefore the actuation rod 3120) in the distal direction relative to the medicament container (or barrel) 3120.

The distal end portion 3132 of the barrel 3130 includes the threads 3138 that can facilitate the removable coupling of the barrel 3130 to the needle assembly 3200 or a vial adapter (not shown). The vial adapter can include any of the vial adapters shown and described in U.S. patent application Ser. No. 15/427,823, entitled "Ocular Injection Kit, Packaging, and Methods of Use," Filed Feb. 8, 2017, which is incorporated by reference herein in its entirety, and can be used as part of a dosage preparation operation to prepare a dose of a substance (i.e., drug or medicament) within the barrel 3130 for subsequent delivery. Although the distal end portion 3132 is shown as including the threads 3138, in other embodiments, the distal end portion 3132 can include any suitable coupling mechanism to which the needle assembly 3200 can be coupled (either removably or permanently).

Referring to FIGS. 15-20, the needle assembly 3200 includes a housing (also referred to as a "hub housing" or "hub member") 3210, an adjustment member 3250, a microneedle (also referred to as a puncture member) 3240, and a needle cover (or cap) 3270. The housing 3210 includes a proximal end portion 3211 and a distal end portion 3212, and is configured to be removably coupled to the medicament container 3130. The proximal end portion 3211 includes an outer wall 3213 and a container protrusion 3218. The outer wall 3213 defines an opening (or recess) 3214 and includes threads 3215. The container protrusion 3218 defines a lumen 3219. This arrangement facilitates the removably coupling between the proximal end portion 3211 of the hub housing 3210 and the medicament container 3130. In use, the distal end portion 3132 of the medicament container 3130 is disposed within the recess 3214. More particularly, the threads 3138 are engaged with the threads 3215 to securely couple the hub housing 3210 to the medicament container 3130. When the hub housing 3210 is coupled to the medicament container 3130, the container protrusion 3218 is disposed within the lumen of the medicament container 3130, thereby placing the medicament container 3130 in fluid communication with the needle assembly 3200 via the lumen 3219. In some embodiments, an outer surface of the container protrusion 3218 can be tapered or can include a sealing member to fluidically isolate the medicament container 3130 and the lumen 3219 from external volumes (e.g., to prevent leaks). For example, in some embodiments, the container protrusion 3218 is a tapered Luer fitting that matingly engages an opening of the medicament container 3130.

Figure 21:
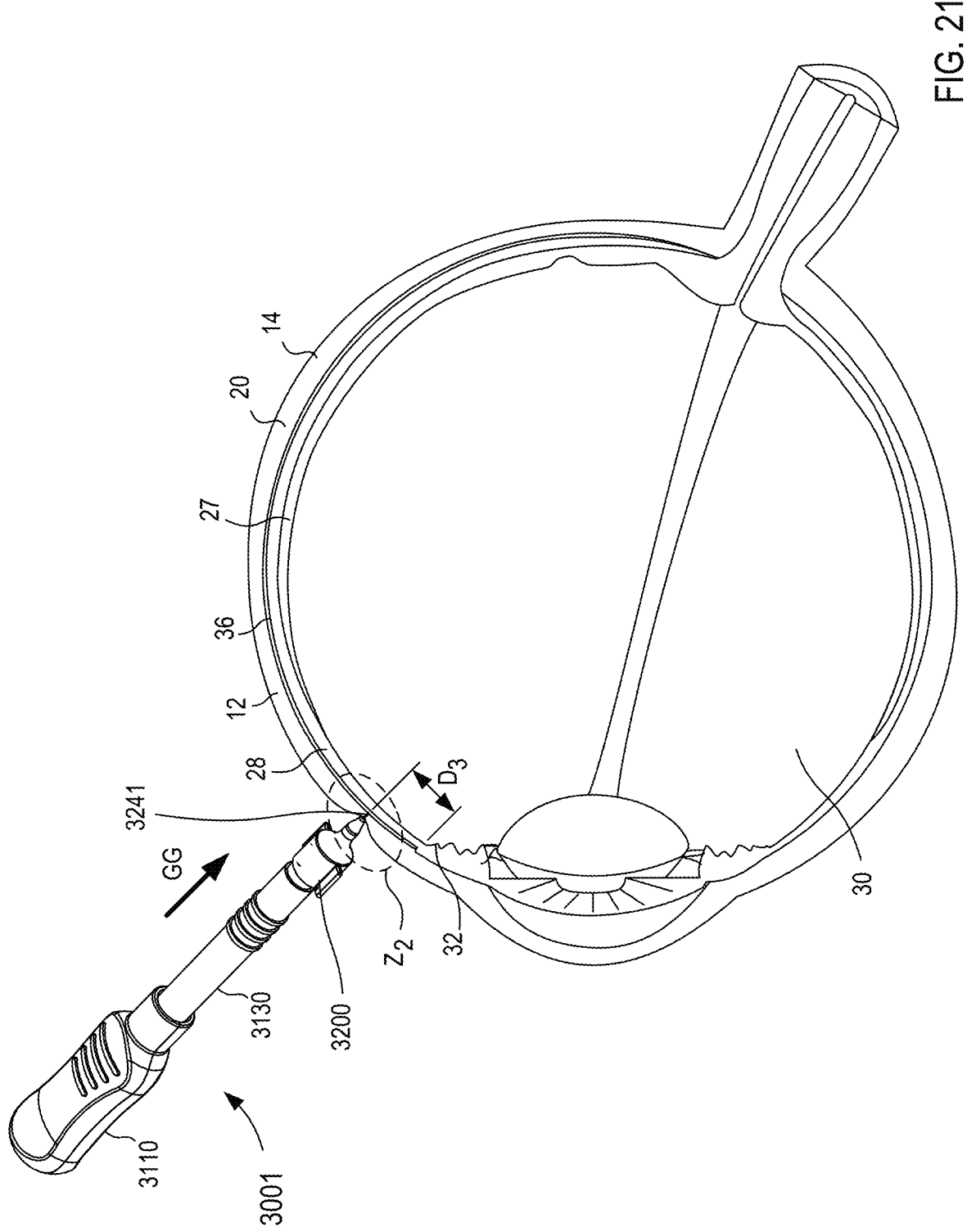
FIG. 21 is a view of the injector assembly of FIGS. 12 and 13 in use during an injection procedure into the human eye.
Figure 22:
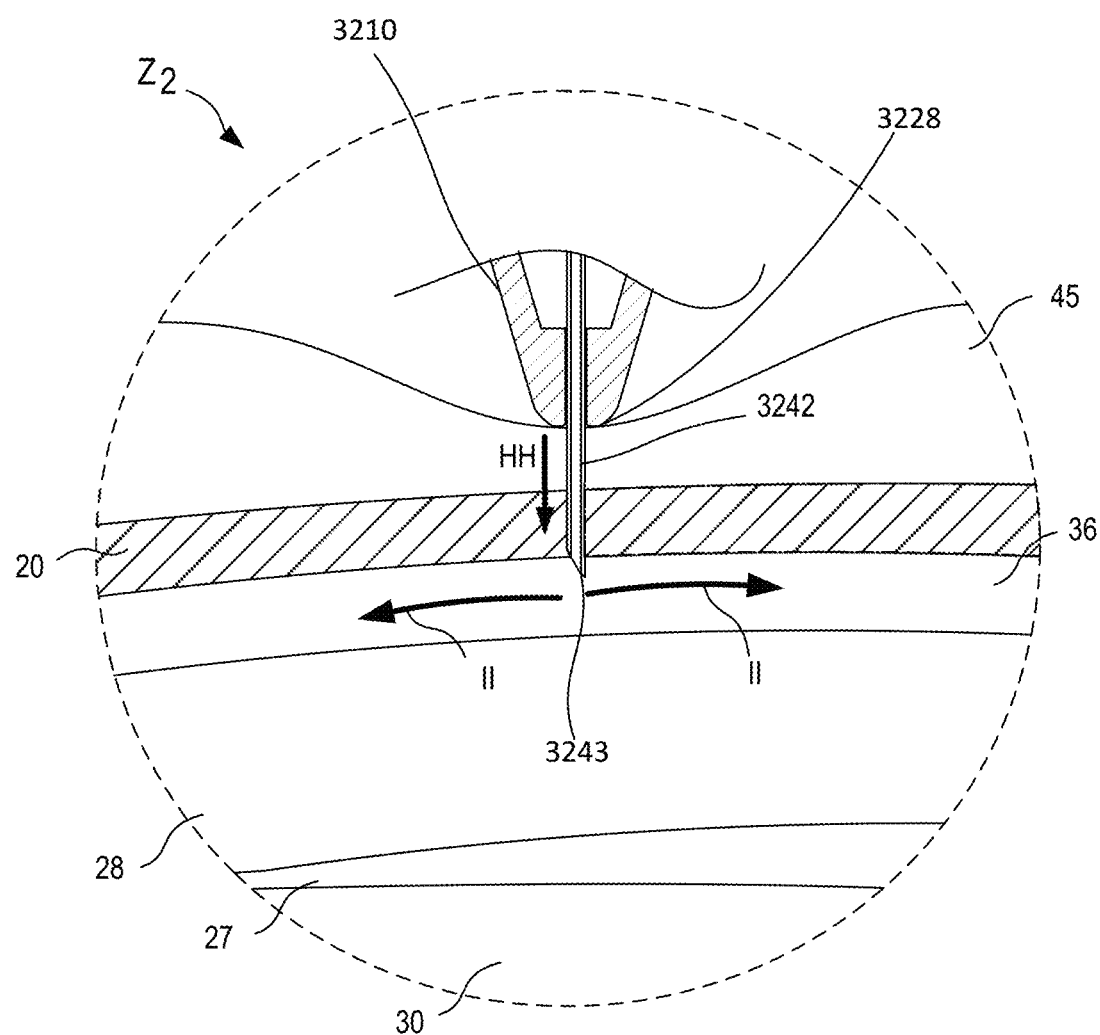
FIG. 22 is an enlarged view of a portion of the medical injector of FIGS. 12 and 13 and the human eye, identified in FIG. 21 by the region $Z_2$.

The distal end portion 3212 of the hub housing 3210 includes a wall 3123 that has an inner surface 3125, and a distal-most hub surface 3228. The inner surface 3125 defines an inner volume 3124 within which the adjustment member 3150 is movably disposed, as described below. The hub surface 3228 defines an opening 3229 in fluid communication with the inner volume 3124 and within which a portion of the microneedle 3240 is movably disposed. The hub surface 3228 is a contact surface having any suitable shape and/or size configured to contact a target surface (e.g., the conjunctiva 45, as shown in FIG. 22) of a target tissue (e.g., the eye) during an injection operation (see FIGS. 21 and 22). For example, in some embodiments, the hub surface 3228 is configured to deform the target surface (e.g., the conjunctiva 45 of the eye) when the distal end portion 3212 is brought into contact with the target surface. In some embodiments, the hub surface 3228 can have a substantially convex shape, for example, a hemispherical shape, and can define a sealing portion that forms a substantially fluid-tight seal with the target surface when the distal end portion 3212 is brought into contact with the target surface. In some embodiments, the hub surface 3228 can deform the target surface to produce a substantially fluid-tight seal between the hub housing 3210 and the target surface, about the opening 3229. In some embodiments, the hub surface 3228 can include any of the characteristics of any of the hubs or hub surfaces shown and described in U.S. Pat. No. 9,180,047, entitled "Apparatus and Methods for Ocular Injection," which is incorporated herein by reference in its entirety.

Figure 18:
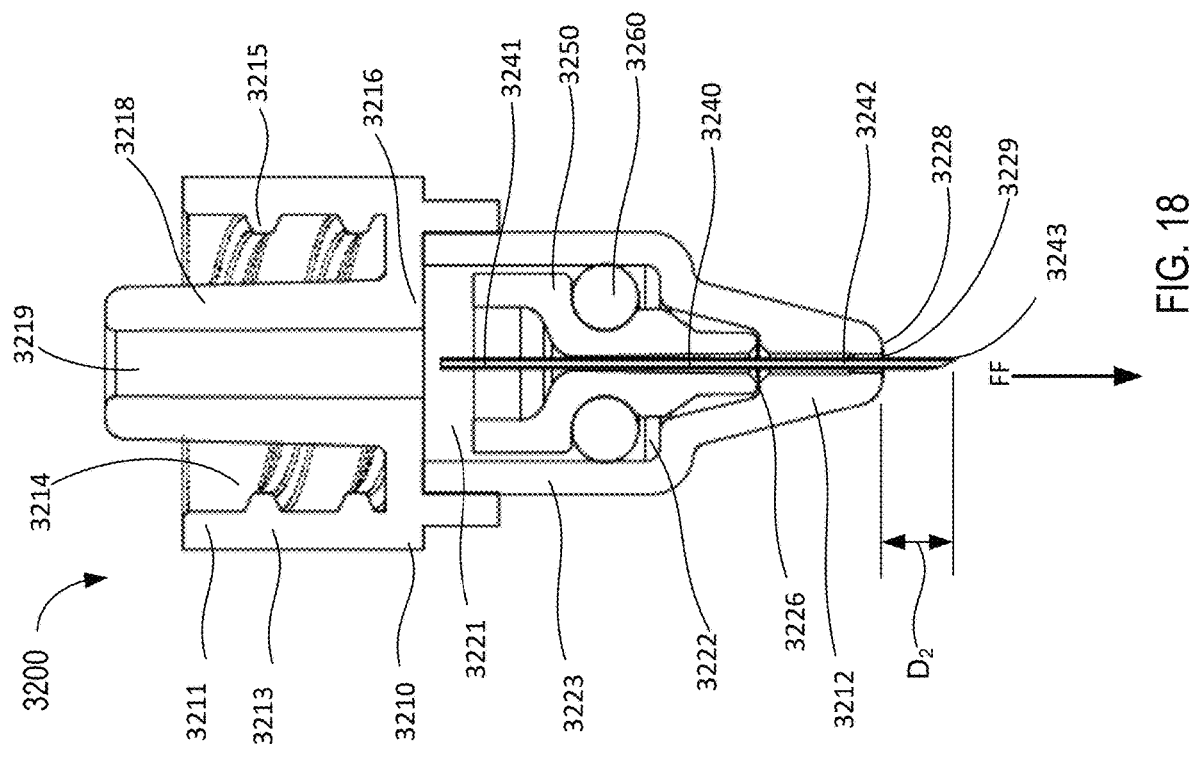
FIGS. 17 and 18 are cross-sectional views of the needle assembly shown in FIGS. 15 and 16 taken along line $X_1$-$X_1$ in FIG. 15, with the needle assembly being in a first configuration and a second configuration, respectively.

The adjustment member 3250 is disposed within an inner volume 3224 defined by the housing 3210, and separates the inner volume into a first chamber 3221 (also referred to as a pressure chamber) and a second chamber 3222. As shown, the first (or pressure) chamber 3221 is in fluid communication with the medicament container 3130 via the lumen 3219 when the housing 3210 is coupled to the medicament container 3130. In this manner, as described herein, a medicament from the medicament container 3130 can be conveyed into the first chamber 3221. Moreover, the medicament within the first chamber 3221 can be pressurized to transition the adjustment member 3250 between a first configuration (FIG. 17) and a second configuration (FIG. 18). Transitioning the adjustment member 3250 produces movement of the microneedle 3240, as described below.

Figure 19:
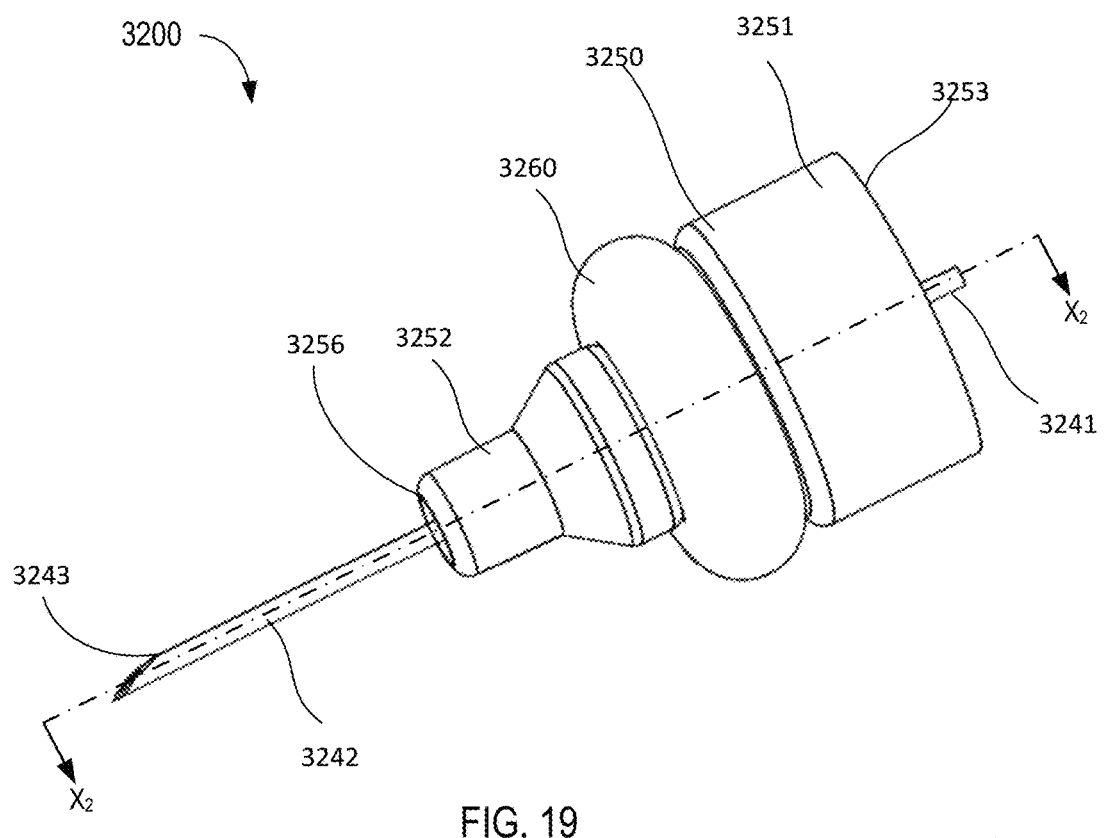
FIG. 19 is a perspective view of an adjustment member of the needle assembly shown in FIGS. 17 and 18.
Figure 20:
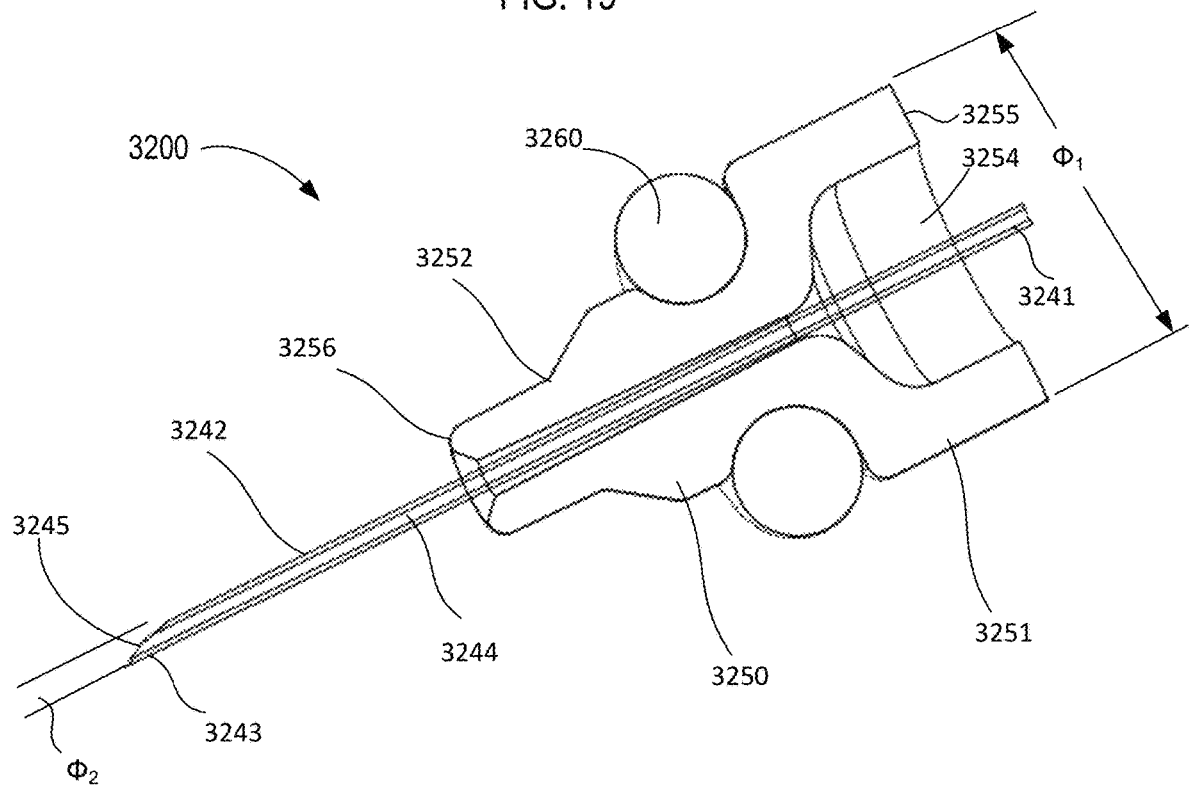
FIG. 20 is a cross-sectional view of the adjustment member shown in FIG. 19 taken along line $X_2$-$X_2$ in FIG. 19.

The adjustment member 3250 includes a proximal end portion 3251 and a distal end portion, and defines a lumen within which the microneedle 3240 is fixedly coupled. The microneedle 3240 can be coupled to and within the adjustment member 3250 via any suitable mechanism, such as by an interference fit, an adhesive, or the like. As shown in FIGS. 19 and 20, the proximal end portion 3251 includes an end surface 3253 that defines a recess 3254 and includes a shoulder 3255. Along with a portion of the inner surface 3225 of the housing 3210, the end surface 3253 (including the portion defining the recess 3254) forms a boundary of the pressure chamber 3221. Thus, the pressure of the medicament within the pressure chamber 3221 acts upon the end surface 3253 to produce a pressure force (similar to the pressure force $F_P$ shown and described above with reference to the adjustment member 1250) to urge the adjustment member to transition from its first configuration (or position) towards its second configuration (or position). The magnitude of the pressure force can be influenced by, among other things, the magnitude of the pressure and the area (or diameter $\Phi_1$) of the end surface 3253.

Figure 17:
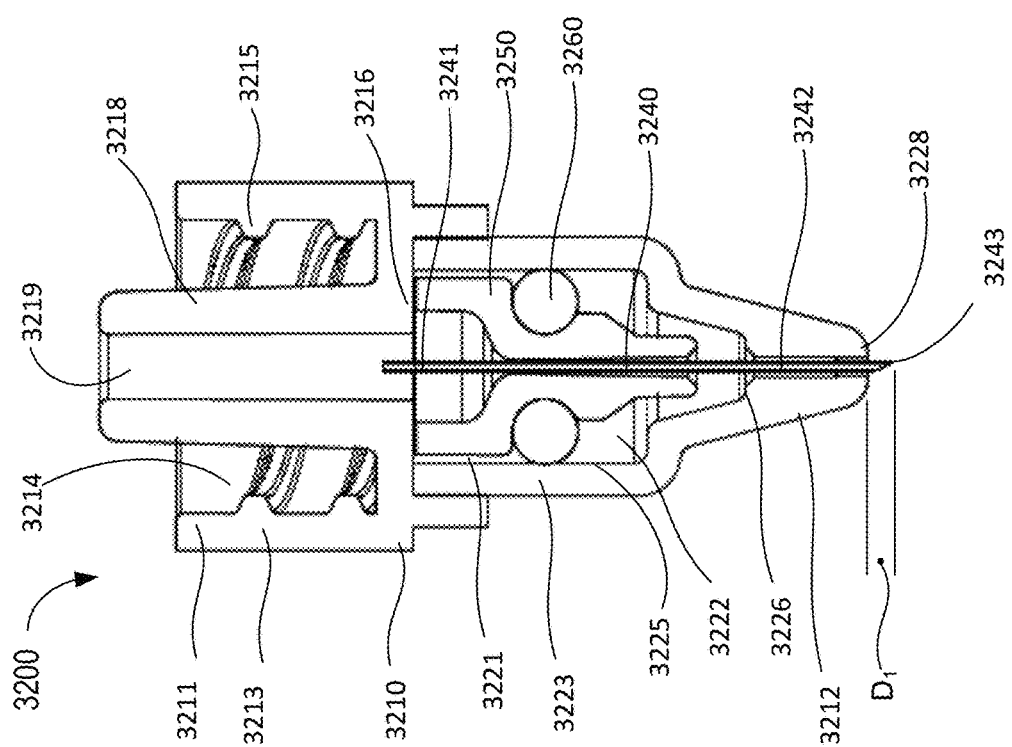

As shown in FIG. 17, the shoulder 3255 is configured to contact a corresponding shoulder 3216 to limit proximal movement of the distal tip 3243 when the adjustment member 3250 is in its first position. In this manner, the proximal force (e.g., the tissue back-pressure force) exerted by the target tissue on the distal end surface 3245 of the microneedle 2340 during initial insertion does not reduce the effective length of the microneedle 3240 to an amount less than the distance $D_1$. Thus, the effective length of the microneedle 3240 is maintained at the distance $D_1$ during the initial insertion operation. The distance $D_1$ can be any suitable value. For example, in some embodiments, the distance $D_1$ can be selected to ensure that the microneedle 3240 can penetrate a sufficient distance within the target tissue during the initial insertion operation without penetrating too far. Specifically, in some embodiments, the distance $D_1$ can be selected to ensure that the microneedle 3240 can penetrate a sufficient distance within the sclera 20 (see FIG. 22), while ensuring that the distal tip 3243 will not likely penetrate the choroid 28 or retina 27. In this manner, the selection of the distance $D_1$ can increase the likelihood that the distal tip 3243 will reach the SCS during the secondary insertion operation. In some embodiments, the distance $D_1$ can be between about 650 µm and about 1100 µm. In other embodiments, the distance $D_1$ can be between about 850 µm and about 1050 µm. In yet other embodiments, the distance $D_1$ can be about 950 µm.

The distal end portion 3252 includes a shoulder 3256 is configured to contact a corresponding shoulder 3226 to limit distal movement of the distal tip 3243 when the adjustment member 3250 is in its second position (see FIG. 18). In this manner, the pressure force exerted on the end surface 3253 during the secondary insertion will not cause the effective length of the microneedle 3240 extend greater than the distance $D_2$. Thus, the effective length of the microneedle 3240 is limited to a maximum amount of the distance $D_2$ during the secondary insertion operation. The distance $D_2$ can be any suitable value. For example, in some embodiments, the distance $D_2$ can be selected to ensure that the microneedle 3240 can penetrate a sufficient distance within the target tissue during the secondary insertion operation without penetrating too far. Specifically, in some embodiments, the distance $D_2$ can be selected to ensure that the microneedle 3240 can penetrate a sufficient distance to reach the SCS 36 (see FIG. 22), while ensuring that the distal tip 3243 will not likely penetrate the choroid 28 or retina 27. In this manner, the selection of the distance $D_2$ can increase the likelihood that the distal tip 3243 will reach the SCS during the secondary insertion operation. In some embodiments, the distance $D_1$ can be between about 1050 µm and about 1450 µm. In other embodiments, the distance $D_1$ can be between about 1150 µm and about 1350 µm. In yet other embodiments, the distance $D_1$ can be about 1250 µm.

The adjustment member 3250 includes a seal 3260 that forms a substantially fluid-tight seal with the inner surface 3225 of the hub housing 3210. In this manner, the seal 3260 can fluidically isolate the first chamber 3221 from the second chamber 3222. Although shown as being an O-ring, in other embodiments, the adjustment member 3250 (or any of the adjustment members described herein) can include any suitable seal. For example, in some embodiments, the adjustment member 3250 (or any of the adjustment members described herein) can include an overmolded seal. In other embodiments, the adjustment member 3250 (or any of the adjustment members described herein) can include multiple sealing members.

The microneedle (or puncture member) 3240 can be any suitable device to puncture the target surface (e.g., the conjunctiva 45 and/or sclera 20) and define a passageway within the target tissue. As shown, the microneedle 3240 includes a proximal end portion 3241 and a distal end portion 3242, and defines a lumen 3244 through which the medicament can be conveyed from the medicament container 3130 and/or the first chamber 3221. The microneedle 3240 is coupled to the adjustment member 3250 such that the proximal end portion 3241 is in fluid communication with the first chamber 3221 and/or the lumen 3219. In this manner, a substance (e.g., a drug or medicament) can be conveyed from the medicament container 3130 through the microneedle 3240 via the first chamber 3221 and/or the lumen 3219. The distal end portion 3242 of the microneedle 3240 includes a distal end surface 3245 that is beveled or a sharpened to facilitate puncturing the target tissue. Further, as shown in FIG. 20, the distal end portion 3242 has a diameter $\Phi_2$, which, as described above, can influence the magnitude of the tissue back-pressure force exerted on the microneedle 3240 during an insertion/injection operation. The distal end surface 3245 can have any suitable shape, size and/or geometry (e.g., bevel angle, bevel height, bevel aspect ratio or the like). For example, in some embodiments, the microneedle 3240 can include any of the beveled surfaces shown and described in International Patent Application Publication No. WO2014/036009, entitled, "Apparatus and Methods for Drug Delivery Using Microneedles," filed on Aug. 27, 2013, the disclosure of which is incorporated by reference herein in its entirety.

The distal end surface 3245 includes a distal tip 3243. Similarly stated, the distal tip 3243 is formed by the intersection of the distal end surface 3245 and an outer side wall of the microneedle 3240. Referring to FIG. 17, the distal tip 3243 of the puncture member extends from the hub surface 3228 (through the opening 3229) by a first distance $D_1$ when the adjustment member 3250 is in the first configuration. Referring to FIG. 18, the distal tip 3243 of the puncture member extends from the hub surface 3228 (or through the opening 3229) by a second distance $D_2$ when the adjustment member 3250 is in the second configuration. In this manner, the position of the microneedle 3240 relative to the hub surface 3228 (i.e., the effective length) can change during an injection operation to ensure that the distal tip 3243 (and therefore the opening in the beveled distal end surface 3245) is placed within the desired region of (or at the desired depth within) the target tissue during medicament delivery. Moreover, as described herein, the position of the distal tip 3243 relative to the hub surface 3228 is changed automatically and in an infinite number of positions (within a predefined range). Said another way, the position of the distal tip 3243 relative to the hub surface 3228 is changed in response to the user actuating the device without any additional input from the user. Thus, the user need not separately manipulate any needle adjustment features, and need not monitor the actual depth of the distal tip 3243 within the target tissue.

The cap 3270 of the needle assembly 3200 is removably coupled to the hub housing 3210, and is configured to substantially house, cover, enclose, protect, isolate, etc. at least a portion of the microneedle 3240. This arrangement limits contact between the user and the distal end 3242 of the microneedle 3240. Moreover, in some embodiments, the distal end of the cap 3270 can be used to measure and/or mark the surface of the eye, and thus minimizing contact between the user and the areas that will directly contact the eye.

The operation of the injector assembly 3001 is similar in many respects to the operation of the injector assembly 1001 as described above. For example, the initial insertion operation of the injector assembly 3001 is similar to that described above for use of the injector assembly 1001. Specifically, in some embodiments, the injector assembly 3001 can be used to perform an injection of a substance into the SCS. Referring to FIG. 21, in some embodiments, the initial insertion operation can be performed at an injection site at predetermined distance from the limbus 32. For example, the injection site can be a distance $D_3$ from the limbus 32 that is about 1 mm, about 2 mm, about 3 mm, about 4 mm, about 5 mm, about 6 mm, about 7 mm, about 8 mm, about 9 mm, about 10 mm, or more. In other instances, an injection site can be relative to any suitable portion of the eye. The initial insertion operation can include inserting the distal tip 3243 until hub surface 3228 contacts the target surface, as shown by the arrow FF in FIG. 21. Thus, the insertion depth of the puncture member 3240 after the initial insertion is the same as the effective length of the puncture member 3240 (which is the distance $D_1$).

Referring to FIG. 22, in some embodiments, initial insertion force can be maintained such that the hub surface 3238 deforms, indents, and/or otherwise forms a "dimple" in the target surface (e.g., the conjunctiva 45 of the eye 10). The "dimple" can facilitate a desired transfer of the medicament from the medicament container 1130 to the target region (e.g., the SCS 36) via the microneedle 3240. The hub surface 3238 can be maintained in such a position throughout the procedure (e.g., the injection of medicament into a SCS 36). In this manner, the "dimple" (e.g., the interface between the distal surface of the hub surface 3238 and the surface of the target location) can limit and/or prevent seepage of the medicament from the target region during injection and post-injection, thereby promoting desirable transfer of the medicament to the target region (e.g., the SCS 36). In some embodiments, the hub surface 3238 can include a sealing portion, which can be a convex surface, a surface having a smooth finish (e.g., with a surface finish of less than Ra=1.6 µm) or the like.

The force to complete the initial insertion can be transferred to the hub surface 3228 and/or the distal tip 3243 via the outer surface (e.g., the ridges 3137) of the medicament container 3130. Moreover, as described above, the shoulder 3255 is maintained in contact with the shoulder 3216 to maintain the effective length at the distance $D_1$ during the initial insertion operation.

After the initial insertion operation, a portion of the medicament from within the medicament container 3130 can then be conveyed from the medicament container 3130 into the lumen 3219 and/or the first chamber 3221. This procedure can be performed by applying a force on the handle 3110 to move the elastomeric member 3128 within the medicament container 3130. The force applied to the handle 3110 can be any suitable force. For example, in some embodiments, the force exerted can be about 2 N, about 3 N, about 4 N, about 5 N, about 6 N or more and inclusive of all ranges therebetween. This pressurizes the medicament within the medicament container 3130, which, in turn, pressurizes the medicament within the lumen 3219 and/or the first chamber 3221. By pressurizing the first chamber 3221, the forces acting on the adjustment member 3250 (and the puncture member 3240) can, under certain circumstances, cause the adjustment member 3250 to transition from its first configuration (FIG. 17) to its second configuration (FIG. 18). Similarly stated, the puncture member 3240 and the adjustment member 3250 are collectively configured such that the adjustment member 3250 can transition within the housing 3210 from its first configuration (or position) towards its second configuration (or position) when the pressure $P_2$ within the first chamber 3221 is greater than a threshold pressure.

After the first chamber 3221 is pressurized, the primary forces acting on the adjustment member 3250 include the pressure force (similar to the pressure force $F_P$ described with reference to FIG. 8), the friction force (similar to the pressure force $F_P$ described with reference to FIG. 8), and the tissue back-pressure force (similar to the back-pressure force $F_{BP}$ described with reference to FIG. 8). The pressure force is produced by the pressurized medicament in the first chamber 3221, and acts in a distal direction on the end surface 3253 of the adjustment member 3250. The friction force is produced by the sliding contact between the seal 3260 and the inner surface 3225 of the hub housing 3210, and acts to oppose the distal movement of the adjustment member 3250. As described above, the tissue back-pressure force is the force exerted by the target tissue on both the distal end surface 3245 and the medicament present at the distal end surface 3245.

Thus, when the pressure force is greater than the sum of the friction force and the tissue back-pressure force, the adjustment member 3250 transitions from its first configuration (FIG. 17) towards its second configuration (FIG. 18). When the pressure within the pressure chamber 3221 is reduced such that the pressure force is less than the sum of the friction force and the tissue back-pressure force, however, the transition of the adjustment member 3250 stops. Thus, depending on the region of tissue within which the distal tip 3243 is disposed and the pressure applied within the first chamber 3221, the adjustment member 3250 can transition between the first configuration, the second configuration, and an infinite number of configurations therebetween. This, in turn, causes the distal tip 3243 to move distally within the target tissue during a secondary insertion operation.

In some embodiments, puncture member 3240 and the adjustment member 3250 are collectively configured such that the adjustment member 3250 transitions from the first configuration towards the second configuration when the pressure within the first chamber 3221 is greater than a threshold pressure. Additionally, the puncture member 3240 is configured such that the substance is maintained within the first chamber 3221 when: A) the distal tip 3243 of the puncture member 3240 is within a region (e.g., the sclera) of the target tissue having a density greater than a threshold density, and B) the pressure within the first chamber 3221 is greater than the threshold pressure. Similarly stated, in some embodiments, when the distal tip 3243 is within a region of tissue having a higher density and/or lower porosity and when the pressure within the pressure chamber 3221 is greater than a threshold pressure, the balance of forces acting on the adjustment member 3250 and the puncture member 3240 can be such that the adjustment member 3250 transitions towards its second configuration, but a flow of medicament through the puncture member 3240 is prevented. In this manner, even though the medicament is pressurized, the distal tip 3243 can move distally (i.e., the secondary insertion) without the medicament flowing out of the puncture member 3240. Said another way, in some embodiments, the injector assembly 3001 can be actuated to pressurize the first chamber 3221 at a pressure that is sufficient to move the distal tip 3243 within the target tissue, while maintaining the medicament within the first chamber 3221 and/or puncture member 3240.

This arrangement can facilitate injection of the drug within a specific region of the target tissue, such as, for example, the SCS. Specifically, after the initial insertion operation, the distal tip 3243 can be within the sclera 20. When the handle 3110 is moved relative to the medicament container 3130, the pressure produced within the pressure chamber 3221 can be such that the adjustment member 3250 transitions towards the second configuration, thereby moving the distal tip 1243 further into the eye, as shown by the arrow GG in FIG. 22. Moreover, because the sclera 36 has a higher density than the SCS (or region where the SCS is to be opened or formed), the pressure is insufficient to cause the medicament to flow out of the puncture member 3240 when the distal tip is within the sclera 45. In other words, the injector assembly 3001 is specifically configured or "calibrated" such that the force applied to the handle 3110 under normal operating conditions is insufficient to convey the drug formulation to the sclera 20.

Referring to FIG. 22, when the distal tip 1243 advances through the sclera 45 and into the SCS 36 (or the region at which the SCS will be produced), as shown by the arrow GG, the density of the target tissue decreases, and the tissue back-pressure on the distal end surface 3245 also decreases. Accordingly, the lower tissue back-pressure allows the medicament to flow from the first chamber 3221 and through the puncture member 1240. This is shown by the arrows HH in FIG. 22, which show the flow in the SCS 36. The flow of the medicament also causes the pressure within the first chamber 3221 to decrease, thereby slowing and/or stopping the transition (or movement) of the adjustment member 3250. Thus, when the distal tip 3243 reaches the SCS 36, movement of the distal tip 3243 slows or stops, and the medicament flows into SCS. Although the flow of the medicament is shown as being within the SCS, in other embodiments, the flow can be conveyed into at least one of a lower portion of the sclera, a choroid of the eye, a subretinal space of the eye, or a retina of the eye.

Figure 23:
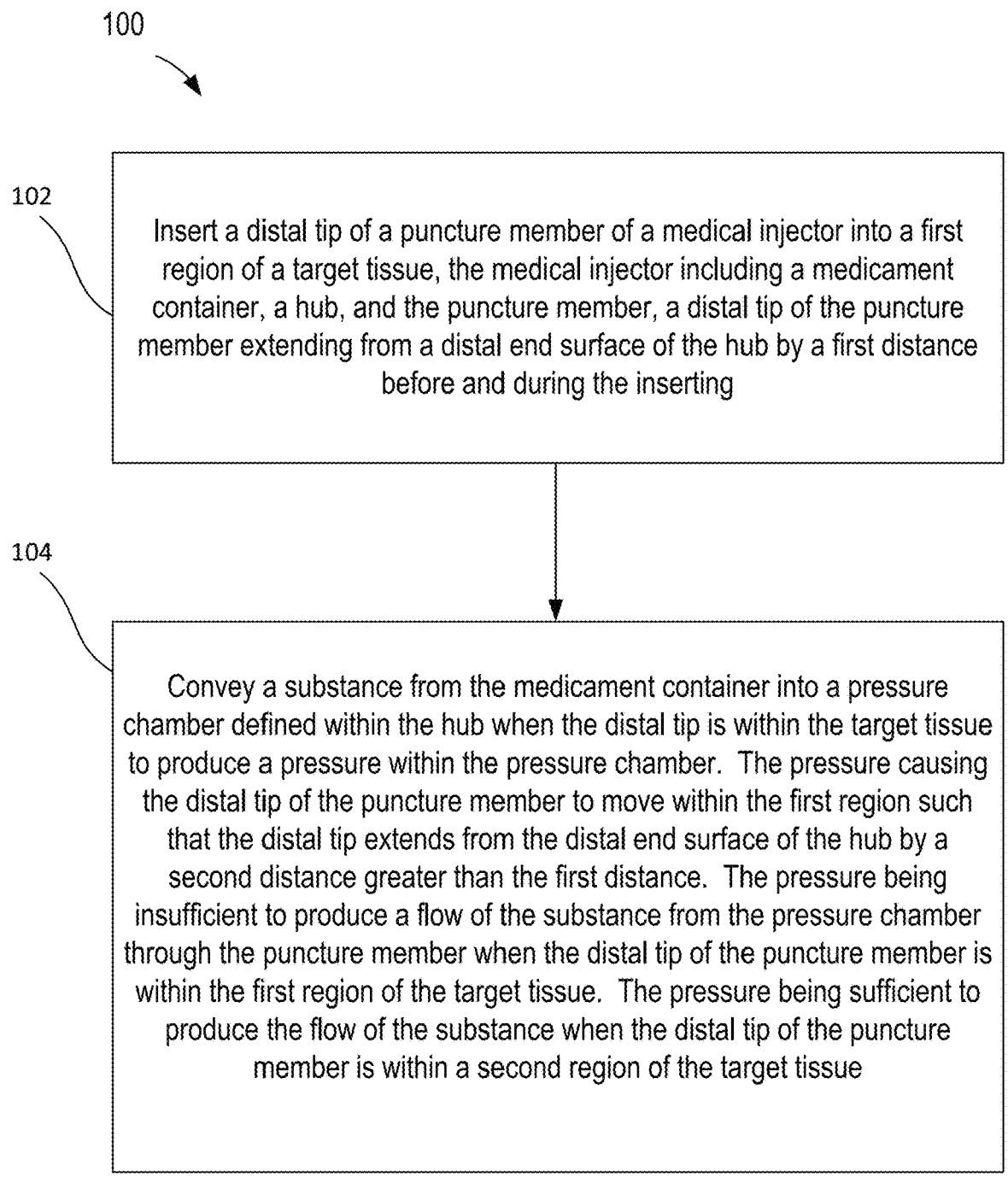
FIG. 23 is a flow chart of a method of injecting a medicament according to an embodiment.

In some embodiments, a method includes delivering a substance to a predetermined region (e.g., the SCS) within a target tissue. Such methods can be performed using any of the injection devices described herein. FIG. 23 is a flow chart of a method 100 of delivering a substance according to an embodiment. Although the method 100 is described in conjunction with the injector assembly 3001 shown and described above, in other embodiments, the method 100 can be performed using any suitable injector. The method includes inserting a distal tip (e.g., the tip 3243) of a puncture member (e.g., the microneedle 3240) of a medical injector (e.g., the injector 3001) into a first region of a target tissue, at 102. The medical injector includes a medicament container, a hub, and the puncture member (e.g., which can be a part of the needle assembly 3200). The distal tip of the puncture member extends from a distal end surface of the hub by a first distance before and during the inserting. This operation is similar to the "initial insertion" operation described above with reference to the injector assemblies 1001, 2001, and 3001.

In some embodiments, the distal tip is inserted such that a centerline of the puncture member and a surface line tangential to the target surface defines an angle of entry of between about 75 degrees and about 105 degrees. Moreover, in some embodiments, the distal tip can be inserted until a hub surface (e.g., the surface 3228) contacts a target surface of the target tissue.

A substance (e.g., a drug) is then conveyed from the medicament container into a pressure chamber defined within the hub when the distal tip is within the target tissue to produce a pressure within the pressure chamber, at 104. The pressure causes the distal tip of the puncture member to move within the first region of the target tissue such that the distal tip of the puncture member extends from the distal end surface of the hub by a second distance greater than the first distance. The pressure is insufficient to produce a flow of the substance from the pressure chamber through the puncture member when the distal tip of the puncture member is within the first region of the target tissue. The pressure is sufficient to produce a flow of the substance from the pressure chamber through the puncture member when the distal tip of the puncture member is within a second region of the target tissue.

In some embodiments, the target tissue is an eye, the first region is an upper portion of the sclera of the eye, and the second region includes at least one of a suprachoroidal space, a lower portion of the sclera, a choroid of the eye, a subretinal space of the eye, or a retina of the eye.

In some embodiments, the substance includes at least one of a VEGF, a VEGF inhibitor, a PDGFR inhibitor, or a combination of any of the VEGF, the VEGF inhibitor, and the PDGFR inhibitor.

In some embodiments, the substance is conveyed by manually exerting a force of less than about 6N on an actuation rod (e.g., the actuation rod 3120) to move a distal end portion of the actuation rod within the medicament container.

In some embodiments, the pressure within the pressure chamber decreases to a second pressure in response to the flow of the substance from the pressure chamber through the puncture member when the distal tip of the puncture member is within the second region of the target tissue. This is shown, for example, in the graph in FIG. 9. In such embodiments, the second pressure is insufficient to move the puncture member relative to the distal end surface of the hub. In this manner, the effective length of the puncture member is changed automatically and in an infinite number of positions (within a predefined range). Said another way, the position of the distal tip relative to the hub surface is changed in response to the user actuating the device without any additional input from the user.

FIG. 24 is a flow chart of a method 200 of delivering a substance according to an embodiment. Although the method 200 is described in conjunction with the injector assembly 3001 shown and described above, in other embodiments, the method 200 can be performed using any suitable injector. The method includes inserting a distal tip (e.g., the tip 3243) of a puncture member (e.g., the microneedle 3240) of a medical injector (e.g., the injector 3001) into a first region of a target tissue, at 202. The medical injector includes a medicament container, a hub, and the puncture member (e.g., which can be part of the needle assembly 3200). The distal tip of the puncture member extends from a distal end surface of the hub by a first distance before and during the inserting. This operation is similar to the "initial insertion" operation described above with reference to the injector assemblies 1001, 2001, and 3001.

A force is manually exerted on a proximal end portion of an actuation rod to move a distal end portion of the actuation rod within the medicament container, at 204. The movement of the distal end portion of the actuation rod causes the following. First, the distal tip of the puncture member moves in a distal direction relative to the distal end surface of the hub from the first region of the target tissue to a second region of the target tissue, at 204A. The force is insufficient to produce a flow of the substance from the pressure chamber through the puncture member when the distal tip of the puncture member is within the first region of the target tissue. Second, the substance flows from the pressure chamber through the puncture member when the distal tip of the puncture member is within a second region of the target tissue, at 204B.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the puncture member 1240 is shown as defining a lumen having a relatively constant diameter, in other embodiments, any of the puncture members and/or microneedles described herein can include a variable diameter lumen of the types shown and described in U.S. Patent Publication No. 2017/0095369, entitled "Variable Diameter Cannula and Methods for Controlling Insertion Depth for Medicament Delivery," the disclosure of which is incorporated by reference herein in its entirety.

Although the needle assembly 3200 is shown and described as being removably coupled to the barrel 3130, in other embodiments, the needle assembly 3200 (or any of the hub housings or needle assemblies described herein) can be coupled to a medicament container in a manner that precludes removal from the medicament container during the intended (or "normal") use of the injector assembly. In such embodiments, the needle assembly can be permanently coupled to the medicament container by a weld joint, an adhesive, a bond, or the like.

In some embodiments, any of the needle assemblies described herein, including the needle assembly 3200, can include a mechanism by which the distance $D_1$ and/or the distance $D_2$ can be adjusted during assembly. For example, in some embodiments, a hub housing can include an opening through which an adjustment tool, shim, or the like can be inserted to adjust either or both of the distance $D_1$ or the distance $D_2$. Such adjustment can be useful to ensure that either or both of the distance $D_1$ or the distance $D_2$ are within the desired tolerance, which can be impacted by slight changes in the position of the microneedle within the adjustment member, changes in the position of the "end stop" shoulders (e.g., the shoulders 3216 and 3226) due the coupling of the distal portion of the needle assembly and the proximal portion of the needle assembly, or the like.

Figure 25:
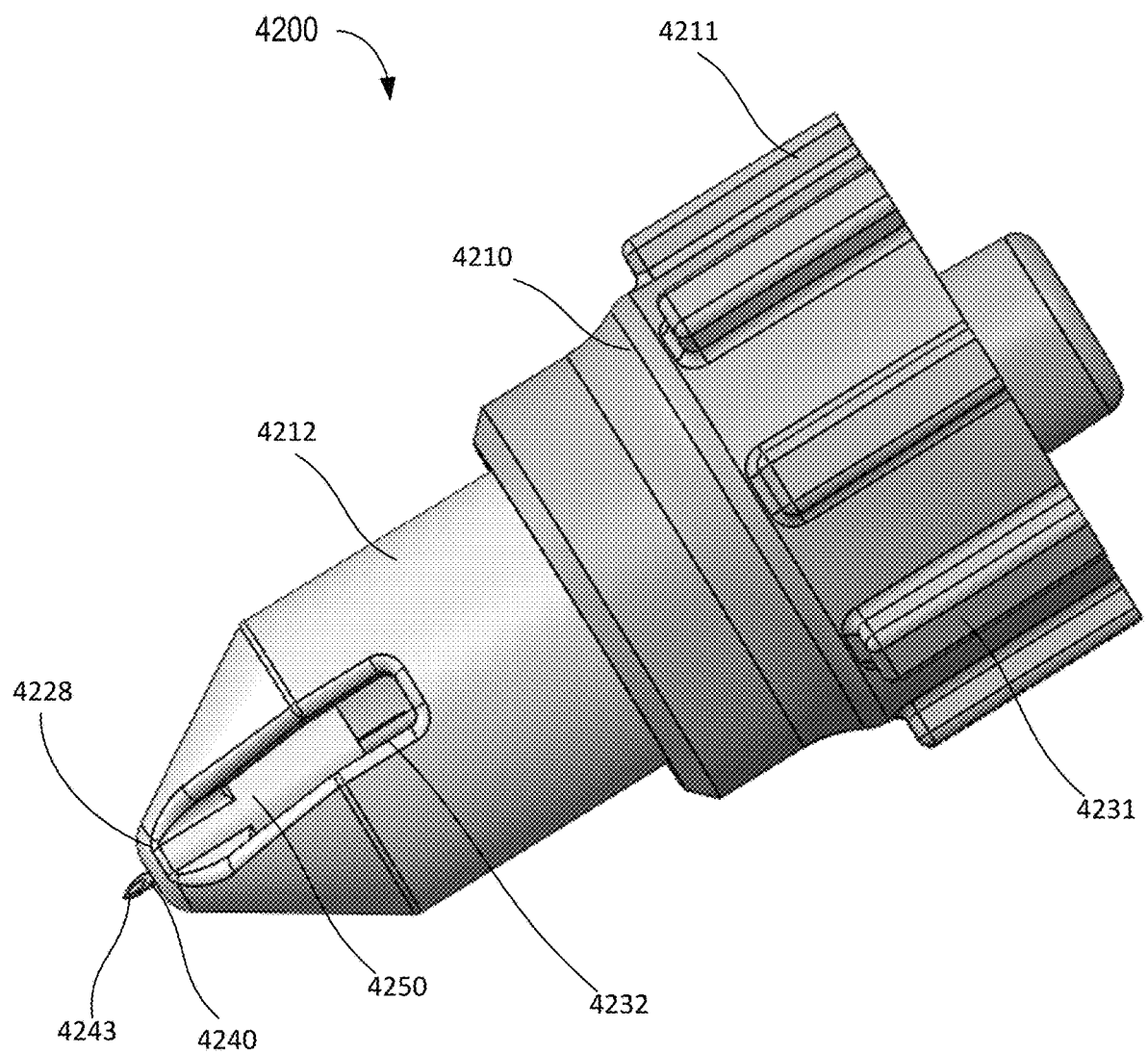
FIG. 25 is a perspective view of a needle assembly according to an embodiment.

For example, FIG. 25 is a side view of a needle assembly 4200 according to an embodiment, which can be used with any of the injector assemblies described herein. The needle assembly 4200 is similar in many respects to the needle assembly 3200, and is therefore not described in detail below. As shown, the needle assembly 4200 includes a housing (also referred to as a "hub housing" or "hub member") 4210, an adjustment member 4250, and a microneedle (also referred to as a puncture member) 4240. The housing 4210 includes a proximal end portion 4211 and a distal end portion 4212, and is configured to be removably coupled to any of the medicament containers described herein (e.g., the medicament container 3130). The proximal end portion 4211 is similar to the portion 3211 described above, and can be removably coupled to a medicament container. Moreover, as shown the outer wall of the proximal end portion 4211 includes a series of ridges (or protrusions) 4231 that can be grasped and/or manipulated by the user during the coupling (or de-coupling) of the needle assembly 4200 from the medicament container.

The distal end portion 4212 of the hub housing 4210 includes a wall that has a distal-most hub surface 4228. Like the hub housing 3210, the distal end portion 4212 defines an inner volume within which the adjustment member 4150 is movably disposed. The hub surface 4228 defines a first opening in fluid communication with the inner volume and within which a portion of the microneedle 4240 is movably disposed. The wall of the distal end portion 4212 defines a second opening 4232, which is also in fluid communication with the inner volume, and through which a portion of the adjustment member 4250 and/or the inner volume can be accessed.

Like the needle assembly 3200 described above, the adjustment member 4250 is fixedly coupled to the microneedle 4240, and is disposed within the inner volume defined by the housing 4210. The adjustment member separates the inner volume into a first chamber (not shown, but similar to the pressure chamber 3221) and a second chamber. Thus, when a substance is pressurized within the first chamber, the adjustment member 4250 is moved from a first position to a second position. Transitioning the adjustment member 4250 produces movement of the microneedle 4240, as described above.

Although not shown in FIG. 25, the needle assembly 4200 includes a mechanism (e.g., shoulders, end stops, or the like) to limit proximal movement of the distal tip 4243 when the adjustment member 4250 is in its first position. In this manner, the proximal force (e.g., the tissue back-pressure force) exerted by the target tissue on the microneedle 2340 during initial insertion does not reduce the effective length of the microneedle 4240 to an amount less than a first distance (e.g., the distance $D_1$ as described above with reference to the needle assembly 3200). Similarly, the needle assembly 4200 includes a mechanism (e.g., shoulders, end stops, or the like) to limit distal movement of the distal tip 4243 when the adjustment member 4250 is in its second position. In this manner, the pressure force exerted on the adjustment member 4250 during the secondary insertion will not cause the effective length of the microneedle 4240 extend greater than a second distance (e.g., the distance $D_2$ as described above with reference to the needle assembly 3200).

During assembly or before an injection operation, a user can access the inner volume and/or the adjustment member 4250 via the opening 4232 to adjust either or both of the distance $D_1$ as or the distance $D_2$. For example, in some embodiments, a shim or other structure can be placed into the inner volume (e.g., in contact with a shoulder therein) to adjust either or both of the distance $D_1$ as or the distance $D_2$. In other embodiments, the needle assembly 4200 can include a threaded calibration mechanism that can be adjusted (e.g., by turning a set screw) via the opening 4232.

In some embodiments, any of the needle assemblies described herein, can include a spring or biasing member to maintain the adjustment member in its first configuration or position. For example, in some embodiments, the needle assembly 3200 can include a biasing member within the inner volume 3224, for example, between the distal shoulder 3226 and the distal-most portion of the adjustment member 3250. In this manner, the adjustment member 3250 will not inadvertently transition distally towards the second configuration (or position) before the pressure in the pressure chamber 3221 reaches a threshold value.

In some embodiments, any of the needle assemblies described herein, can include a magnetic member to maintain the adjustment member in a desired position. For example, in some embodiments, the needle assembly 3200 can include a magnetic member to maintain the adjustment member 3250 in its first configuration or position. In this manner, the adjustment member 3250 is prevented from prematurely transitioning towards its second configuration. In other embodiments, the needle assembly 3200 can include a magnetic member that limits movement of the adjustment member after the distal tip 3243 has reached the second region R2. As described above, when the distal tip 3243 reaches the second region (e.g., the SCS), the substance will begin to flow from the microneedle, resulting in a pressure drop within the pressure chamber 3221. If the user continues applying the distal force (e.g., on the handle 3110) or even increases the distal force, the pressure within the pressure chamber 3221 may increase again. Specifically, in some instances, when the distal tip exits the first region (e.g., the sclera), the space or volume of the second region (e.g., the SCS) is not yet fully formed. In such instances, the flow of the substance can produce or increase the second region (e.g., the SCS), thereby producing the space or volume within which the remainder of the substance can flow. Thus, the fluid pressure to "open up" or produce the second region (e.g., the SCS) can result in a temporary increase in the pressure within the pressure chamber. In such instances, a magnetic member can be used to produce a hysteresis effect that prevents further distal movement of the adjustment member 3250 after the initial pressure drop (indicating that the distal tip 3243 is within the desired tissue region).

In some embodiments, any of the needle assemblies described herein can include any suitable mechanism for producing such a hysteresis effect on the adjustment member therein. For example, although the seal 3260 is shown and described as fluidically isolating the pressure chamber 3221 from the second chamber 3222, in other embodiments, the first chamber 3221 and the second chamber 3222 can be selectively fluidically isolated. For example, in some embodiments, the adjustment member 3250 (or any of the adjustment members shown herein) can include a valve that selectively places the first chamber 3221 in fluid communication with the second chamber 3222. The valve can be actuated, for example, when the pressure within the first chamber 3221 drops below a threshold value after having been elevated. In other words, the valve can be configured to open only when the pressure threshold is crossed from an "upper" direction (e.g., from a high pressure to a low pressure). When opened, the valve can then allow the pressure within the first chamber 3221 to "bleed" thereby preventing further movement of the adjustment member.

Any of the needle assemblies described herein, including the hub housings, the adjustment members and/or the microneedles (or puncture members) described herein, can be formed or constructed from any suitable biocompatible material or combination of materials, including metals, glasses, semi-conductor materials, ceramics, or polymers. Examples of suitable metals include pharmaceutical grade stainless steel, gold, titanium, nickel, iron, gold, tin, chromium, copper, and alloys thereof. The polymer can be biodegradable or non-biodegradable. Examples of suitable biocompatible, biodegradable polymers include polylactides, polyglycolides, polylactide-co-glycolides (PLGA), polyanhydrides, polyorthoesters, polyetheresters, polycaprolactones, polyesteramides, poly(butyric acid), poly (valeric acid), polyurethanes and copolymers and blends thereof. Representative non-biodegradable polymers include various thermoplastics or other polymeric structural materials known in the fabrication of medical devices. Examples include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly (vinyl imidazole), chlorosulphonate polyolefins, polyethylene oxide, blends and copolymers thereof.

A wide range of ocular diseases and disorders may be treated by the methods and with the kits described herein. Non-limiting examples of such ocular diseases include uveitis, glaucoma, diabetic macular edema or retinopathy, macular degeneration, retinoblastoma, and genetic diseases. The methods described herein are particularly useful for the local delivery of drugs that need to be administered to the posterior region of the eye, for example the retinochoroidal tissue, macula, and optic nerve in the posterior segment of the eye. In one embodiment, the delivery methods and devices described herein may be used in gene-based therapy applications. For example, the methods may administer a fluid drug formulation into the suprachoroidal space to deliver select DNA, RNA, or oligonucleotides to targeted ocular tissues Any of the medicament containers (e.g., vials) and/or kits shown and described herein can include and/or be used with any suitable drug, medicament or therapeutic agent of the types mentioned herein. As used herein, the term "drug" refers to any prophylactic, therapeutic, or diagnostic agent (e.g., a contrast agent). The drug may be selected from suitable proteins, peptides and fragments thereof, which can be naturally occurring, synthesized or recombinantly produced. Representative examples of types of drugs for delivery to ocular tissues include antibodies, anti-viral agents, chemotherapeutic agents (e.g., topoisomerase inhibitors), analgesics, anesthetics, aptamers, antihistamines, anti-inflammatory agents, and anti-neoplastic agents. In one embodiment, the drug is triamcinolone or triamcinolone acetonide.

In some embodiments, any of the medicaments or drugs described herein (or used in any of the assemblies or methods described herein) can have any suitable viscosity and/or density. As described above, the viscosity can affect the pressure within the pressure chamber that is required to produce a flow within the puncture member. In some embodiments, for example, the medicament can have a viscosity of at least 100 centiPoise. In other embodiments, the medicament or drug can be a high viscosity substance for treatment of the eye (e.g., gel-like substance, a paste-like substance, an emulsion including both a liquid component and a solid component, or the like). In some embodiments, the medicament can have a viscosity of at least about 1000 centiPoise. In some embodiments, the medicament can have a viscosity of at least about 10,000 centiPoise. In other embodiments, the medicament can have a viscosity of at least 100,000 centiPoise (cps). In other embodiments, the medicament can have a viscosity of between about 40,000 cps and about 60,000 cps.

The term "antibody" is intended to refer broadly to any immunologic binding agent such as IgG, IgM, IgA, IgD and IgE. An antibody can be monoclonal or polyclonal, and in one embodiment, is a humanized antibody. The term "antibody" is also used to refer to any antibody-like molecule that has an antigen binding region, and includes antibody fragments such as Fab', Fab, F(ab')2, single domain antibodies (DABs), Fv, scFv (single chain Fv), and engineering multivalent antibody fragments such as dibodies, tribodies and multibodies. The techniques for preparing and using various antibody-based constructs and fragments are well known in the art (see, e.g., Antibodies: A Laboratory Manual, Cold Spring Harbor Laboratory, 1988; incorporated herein by reference).

Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), topoisomerase inhibitors (e.g., topotecan, irinotecan, camptothecin, lamellarin D, etoposide, teniposide, doxorubicin, mitoxantrone, amsacrine), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration (e.g. pegagtanib sodium, ranibizumab, aflibercept and bevacizumab), and glutocorticoid receptor antagonists (e.g., fosdagrocorat, dagrocorat, mapracorat, mifepristone).

In some embodiments, a kit and/or vial includes an integrin antagonist, a selectin antagonist, an adhesion molecule antagonist (e.g., intercellular adhesion molecule (ICAM)-1, ICAM-2, ICAM-3, platelet endothelial adhesion molecule (PCAM), vascular cell adhesion molecule (VCAM)), a leukocyte adhesion-inducing cytokine or growth factor antagonist (e.g., tumor necrosis factor-α (TNF-α), interleukin-1β (IL-1β), monocyte chemotatic protein-1 (MCP-1), or a vascular endothelial growth factor (VEGF)). In some embodiments, a vascular endothelial growth factor (VEGF) inhibitor is included within a kit and/or administered with one of the microneedles described herein. In some embodiments, two drugs are included within a kit and/or are delivered by the methods described herein. The compounds may be administered in one formulation, or administered serially, in two separate formulations. For example, both a VEGF inhibitor and VEGF are provided. In some embodiments, the VEGF inhibitor is an antibody, for example a humanized monoclonal antibody. In further embodiments, the VEGF antibody is bevacizumab. In another embodiment, the VEGF inhibitor is ranibizumab, aflibercept or pegaptanib. In still other embodiments, the devices and methods described herein can be used to deliver one or more of the following VEGF antagonists: AL8326, 2C3 antibody, AT001 antibody, HyBEV, bevacizumab (Avastin), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, Sutent (sunitinib malate), INDUS815C, R84 antibody, KDO19, NM3, allogenic mesenchymal precursor cells combined with an anti-VEGF agent or antibody, MGCD265, MG516, VEGF-Receptor kinase inhibitors, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble FM receptor, Cediranib (Recentin), AV-951 (Tivozanib, KRN-951), Stivarga (regorafenib), Volasertib (BI6727), CEP11981, KH903, Lenvatinib (E7080), terameprocol (EM1421), ranibizumab (Lucentis), Votrient (pazopanib hydrochloride), PF00337210, PRS050, SPO1 (curcumin), Carboxyamidotriazole orotate, hydroxychloroquine, linifanib (ABT869, RG3635), Iluvien (fluocinolone acetonide), ALG1001, AGN150998, DARPin MP0112, AMG386, ponatinib (AP24534), AVA101, Vargatef (nintedanib), BMS690514, KH902, golvatinib (E7050), Afinitor (everolimus), Dovitinib lactate (TKI258, CHIR258), ORA101, ORA102, Axitinib (Inlyta, AG013736), Plitidepsin (Aplidin), Lenvatinib mesylate, PTC299, aflibercept (Zaltrap, Eylea), pegaptanib sodium (Macugen, LI900015), Visudyne (verteporfin), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PTI101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (YN968D1), and AL3818. In addition, delivery of a VEGF inhibitor or VEGF antagonist using the microneedle devices and methods disclosed herein may be combined with one or more agents listed herein or with other agents known in the art.

In one embodiment, delivery of a VEGF antagonist to the suprachoroidal space of the eye using the kits, devices, and methods disclosed herein is used to treat, prevent and/or ameliorate a disease or disorder selected from leukemia, relapsed/refractory leukemia, acute lymphoblastic leukemia, Acute myelogenous leukemia, relapsed or refractory acute myeloid leukemia, atopic dermatitis, recurrent or metastatic carcinoma of the urothelium, advanced urothelial carcinoma, blood disorders, myelofibrosis, brain tumor, glioblastoma, glioma, meningioma, cancer, carcinomatous meningitis (neoplastic meningitis), choroidal neovascularization (CNV), subfoveal choroidal neovascularization, chronic lymphocytic leukemia, chronic myelogenous leukemia, refractory chronic myelogenous leukemia, colon cancer, colorectal cancer, degenerative nerve diseases, Neurodegenerative diseases, diabetic macular edema, visual Impairment due to diabetic macular edema, diabetic retinopathy, dry eye syndrome (inflammation and corneal tissue damage of dry Eye), endometrial cancer, eye diseases, ocular diseases, ocular neovascularization, eye cancer, Neurofibromatosis Type II, head and neck cancer, hematological malignancies, Kaposi's Sarcoma, Hepatocellular Carcinoma, Lung cancer, macular degeneration, age related macular degeneration, exudative age-related macular degeneration, neovascular (wet) age-related macular degeneration (AMD)), subfoveal Neovascular Age-Related macular degeneration, macular edema, macular edema associated with Branch Retinal Vein Occlusion, macular edema following retinal vein occlusion, macular edema with Retinal Vein Occlusion (RVO), multiple myeloma, relapsed or refractory multiple myeloma, multiple sclerosis, myopia, pathological myopia, neuroendocrine tumor, carcinoid tumor, neuroendocrine tumor, non-Hodgkin's Lymphoma, Diffuse Large B-Cell Lymphoma, Non-Small-Cell Lung cancer, Non-Squamous Non-Small-Cell Lung cancer, Non-small-cell-lung Adenocarcinoma, Squamous Non-Small-Cell Lung cancer, corneal graft rejection, osteoarthritis, recurrent symptomatic malignant ascites, peripheral T-cell lymphoma, androgen Independent Psoriasis, pulmonary Fibrosis, Idiopathic Pulmonary Fibrosis, respiratory diseases, retinal detachment, retinal disorders, retinitis pigmentosa, retinal vein occlusion, branch retinal vein occlusion, central retinal vein occlusion, rheumatoid arthritis, sarcoma, alveolar soft part sarcoma, soft tissue sarcoma, scleroderma/systemic sclerosis, solid tumors, refractory germ cell tumors, thyroid cancer, differentiated or medullar thyroid cancer, and West Syndrome (Infantile Spasm).

In certain embodiments, the drug delivered to the suprachoroidal space using the kits, devices, and methods disclosed herein is rapamycin (Sirolimus, Rapamune). In one embodiment, the devices (e.g., microneedle devices) and methods disclosed herein are used in conjunction with rapamycin to treat, prevent and/or ameliorate a wide range of diseases or disorders including, but not limited to: abdominal neoplasms, acquired immunodeficiency syndrome, acute coronary syndrome, acute lymphoblastic leukemia, acute myelocytic leukemia, acute non-lymphoblastic leukemia, adenocarcinoma, adenoma, adenomyoepithelioma, adnexal diseases, anaplastic astrocytoma, anaplastic large cell lymphoma, anaplastic plasmacytoma, anemia, angina pectoris, angioimmunoblastic lymphadenopathy with dysproteinemia, angiomyolipoma, arterial occlusive diseases, arteriosclerosis, astrocytoma, atherosclerosis, autoimmune diseases, B-cell lymphomas, blood coagulation disorders, blood protein disorders, bone cancer, bone marrow diseases, brain diseases, brain neoplasms, breast beoplasms, bronchial neoplasms, carcinoid syndrome, carcinoid Tumor, carcinoma, squamous cell carcinoma, central nervous system diseases, central nervous system neoplasms, choroid diseases, choroid plexus neoplasms, choroidal neovascularization, choroiditis, chronic lymphocytic leukemia, chronic myeloid leukemia, chronic myelomonocytic leukemia, chronic myeloproliferative disorders, chronic neutrophilic leukemia, clear cell renal cell carcinoma, colonic diseases, colonic neoplasms, colorectal neoplasms, coronary artery disease, coronary disease, coronary Occlusion, coronary restenosis, coronary stenosis, coronary thrombosis, cutaneous T-cell lymphoma, diabetes mellitus, digestive system neoplasms, dry eye syndromes, ear diseases, edema, endocrine gland neoplasms, endocrine system diseases, endometrial neoplasms, Endometrial stromal tumors, Ewing's sarcoma, exanthema, eye neoplasms, fibrosis, follicular lymphoma, gastrointestinal diseases, gastrointestinal neoplasms, genital neoplasms, glioblastoma, glioma, gliosarcoma, graft vs host disease, hematologic diseases, hematologic neoplasms, hemorrhagic disorders, hemostatic disorders, Hodgkin disease, Hodgkin lymphoma, homologous wasting disease, immunoblastic lymphadenopathy, immunologic deficiency syndromes, immunoproliferative disorders, infarction, inflammation, intestinal diseases, intestinal neoplasms, ischemia, kidney cancer, kidney diseases, kidney neoplasms, leukemia, B-Cell, leukemia, lymphoid, liver cancer, liver diseases, lung diseases, lymphatic diseases, lymphoblastic lymphoma, lymphoma, macular degeneration, macular edema, melanoma, mouth neoplasms, multiple myeloma, myelodysplastic syndromes, myelofibrosis, myeloproliferative disorders, neuroectodermal tumors, neuroendocrine tumors, neuroepithelioma, neurofibroma, renal cancer, respiratory tract diseases, retinal degeneration, retinal diseases, retinal neoplasms, retinoblastoma, rhabdomyosarcoma, thoracic neoplasms, uveitis, vascular diseases, Waldenstrom Macroglobulinemia, and wet macular degeneration. In addition, delivery of rapamycin using the microneedle devices and methods disclosed herein may be combined with one or more agents listed herein or with other agents known in the art.

In one embodiment, the drug delivered to ocular tissue, for example the sclera or suprachoroidal space, using the kits, microneedle devices, and methods disclosed herein reduces, inhibits, prevents and/or ameliorates inflammation. Examples of drugs that reduce, inhibit, prevent and/or ameliorate inflammation include (but are not limited to): 19AV Agonists, 19GJ agonists, 2MD Analogs, 4SC101, 4SC102, 57-57, 5-HT2 Receptor Antagonist, 64G12, A804598, A967079, AAD2004, AB1010, AB224050, abatacept, Abegrin, Abevac, AbGn134, AbGn168, Abki, ABN912, ABR215062, ABR224050, Abrammune, Abreva, ABS15, ABS4, ABS6, ABT122, ABT325, ABT494, ABT874, ABT963, ABXIL8, ABXRB2, AC430, Accenetra, Acdeam, ACE772, Acebid, Acebloc, aceclofenac, acetaminophen, chlorzoxazone, serrapeptase, tizanidine hydrochloride, betadex, Aceclogesic Plus, Aceclon, Acecloren, Aceclorism, acecrona, Aceffein, acemetacin, Acenac, Acenterine, Acetal-SP, ibuprofen, Acetyl-G, acetylsalicylate dl-lysine, acetylsalicylic acid, Acicot, Acifine, Acik, Alocen, Acloflam-P, Aclomore, Aclon, A-CQ, ACS15, actarit, Actemra, Acthelea liofilizado, Actifast, Actimab-B, Actiquim, Actirin, Actis PLUS, activated leukocyte cell adhesion molecule antibody, Acular X, AD452, adalimumab, ADAMTSS Inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwiflam, AEB071, Aental, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immune-globulin, alclometasone dipropionate, ALD518, aldesleukin, Aldoderma, alefacept, alemtuzumab, Alequel, Alergolon, Alergosone, Aletraxon, Alfenac, Algason, Algin vek coat, Algioflex, Algirex, Algivin Plus, alicaforsen sodium, Alin, Alinia, Aliviodol, Aliviosin, alkaline phosphatase, ALKS6931, allantoin, Allbupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, Alpha-1-antitrypsin, Alpha2BetA1 Integrin Inhibitors, Alphacort, Alphafen, alpha-hexidine, alpha-trypsin, Alphintern, Alpinamed mobility omega 3, Alpoxen, AL-Rev1, Alterase, ALX0061, ALX0761, ALXN1007, ALXN1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, Amifenac, Amimethacin, amiprilose hydrochloride, Amiprofen, Ammophos, Amoflam, AMP110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Aneol, Anergix, Anervax.RA, Anflene, ANG797, Anilixin, Anmerushin, Annexin 1 peptides, annexin A5, Anodyne, Ansaid, Anspirin, Antarene, Anti BST2 antibody, Anti C5a MAb, Anti ILT7 antibody, Anti VLA1 antibody, Anti-alpha 11 antibody, Anti-CD4 802-2, Anti-CD86 Monoclonal Antibody, Anti-chemokine, Anti-DC-SIGN, Anti-HMGB-1 MAb, Anti-IL-18 Mab, Anti-IL-1R MAb, Anti-IL-1R MAb, Anti-IL23 BRISTOL, Anti-inflammatory Peptides, Anti-interleukin 1Beta antibody, Anti-LIGHT antibody, Anti-LIGHT antibody, Anti-MIF Antibody, Anti-MIF Antibody, Anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazone, APD334, Apentac, APG103, Apidone, apilimod mesylate, Apitac, Apitoxin, Apizel, APN Inhibitor, apo-Azathioprine, Apo-Dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY371797, ARRY614, ARRY872, ART621, Artamin, Arthfree, Artho Tech, Arthrexin, Arthrispray, Arthrotec, Arthrovas, Artifit, Artigo, Artin, Artinor, Artisid, Artoflex, Artren Hipergel, Artridol, Artrilase, Artrocaptin, Artrodiet, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASF1096, ASK8007, ASKP1240, ASLAN003, Asmo ID, Asonep, ASP015K, ASP2408, ASP2409, Aspagin, Aspeol, Aspicam, Aspirimex, aspirin, AST120, astaxanthin, AstroCort, Aszes, AT002 antibody, AT007, AT008 antibody, AT008 antibody, AT010, AT1001, atacicept, Ataspin, Atepadene, Atgam, ATG-Fresenius, Athrofen, ATIO03, atiprimod, ATL1222, ATN103, ATN192, ATR107, Atri, Atrmin, Atrosab antibody, ATX3105, AU801, auranofin, Aurobin, Auropan, Aurothio, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azacortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF Inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, Benlysta, benorilate, Benoson, benoxaprofen, Bentol, benzydamine hydrochloride, Benzymin, Beofenac, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason, Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, BI695500, BI695501, BIA12, Big-Joint-D, BIIB023 antibody, Bi-ksikam, Bingo, BioBee, Bio-Cartilage, Bio-C-Sinkki, Biodexone, Biofenac, Bioreucam, Biosone, Biosporin, BIRB796, Bitnoval, Bitvio, Bivigam, BKT140, BKTP46, BL2030, BL3030, BL4020, BL6040, BL7060, BLI1300, blisibimod, Blokium B12, Blokium Gesic, Blokium, BMS066, BMS345541, BMS470539, BMS561392, BMS566419, BMS582949, BMS587101, BMS817399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BRO2001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BTI9, BTK kinase inhibitors, BTT1023 antibody, BTT1507, bucillamine, Bucillate, Buco Reigis, bucolome, Budenofalk, budesonide, Budex, Bufect, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, C5aQb, c7198, c9101, C9709, c9787, CAB101, cadherin 11 antibody, caerulomycin A, CAL263, Calcort, Calmate1, CAM3001, Camelid Antibodies, Camlox, Camola, Campath, Camrox, Camtenam, canakinumab, *candida albicans* antigen, Candin, cannabidiol, CAP1.1, CAP1.2, CAP2.1, CAP2.2, CAP3.1, CAP3.2, Careram, Carimune, Cariodent, Cartifix, CartiJoint, Cartilago, Cartisafe-DN, Cartishine, Cartivit, Cartril-S, Carudol, CaspaCIDe, CaspaCIDe, Casyn, CAT1004, CAT1902, CAT2200, Cataflam, Cathepsin S inhibitor, Catlep, CB0114, CB2 agonist, CC0478765, CC10004, CC10015, CC1088, CC11050, CC13097, CC15965, CC16057, CC220, CC292, CC401, CC5048, CC509, CC7085, CC930, CCR1 Antagonist, CCR6 Inhibitor, CCR7 Antagonist, CCRL2 antagonist, CCX025, CCX354, CCX634, CD Diclofenac, CD102, CD103 Antibody, CD103 Antibody, CD137 antibody, CD16 antibody, CD18 antibody, CD19 antibody, CDld Antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CDK9-Inhibitor, CDP146, CDP323, CDP484, CDP6038, CDP870, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, CellCept, Cellmune, Celosti, Celoxib, Celprot, Celudex, cenicriviroc mesylate, cenplace1-1, CEP11004, CEP37247, CEP37248, Cephyr, Ceprofen, Certican, certolizumab pegol, Cetofenid, Cetoprofeno, cetylpyridinium chloride, CF101, CF402, CF502, CG57008, CGEN15001, CGEN15021, CGEN15051, CGEN15091, CGEN25017, CGEN25068, CGEN40, CGEN54, CGEN768, CGEN855, CGI1746, CGI560, CGI676, Cgtx-Peptides, CH1504, CH4051, CH4446, chaperonin 10, chemokine C-C motif ligand 2, chemokine C-C motif ligand 2 antibody, chemokine C-C motif ligand 5 antibody, chemokine C-C motif receptor 2 antibody, chemokine C-C motif receptor 4 antibody, chemokine C-X-C motif ligand 10 antibody, chemokine C-X-C motif ligand 12 aptamer, Chemotaxis Inhibitor, Chillmetacin, chitinase 3-like 1, Chlocodemin, Chloquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Ciclopren, Cicporal, Cilamin, Cimzia, cinchophen, cinmetacin, cinnoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Claversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPX1023, Cnac, CND0201, CNI1493, CNTO136, CNTO148, CNT01959, Cobefen, CoBenCoDerm, Cobix, Cofenac, Cofenac, COG241, COL179, colchicine, *Colchicum* Dispert, Colchimax, Colcibra, Coledes A, Colesol, Colifoam, Colirest, collagen, type V, Comcort, complement component (3b/4b) receptor 1, Complement Component Cls Inhibitors, complement component C3, complement factor 5a receptor antibody, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Cortan, Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO Inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM Ion Channel Inhibitor, Cratisone, CRB15, CRC4273, CRC4342, C-reactive protein 2-methoxyethyl phosphorothioate oligonucleotide, CreaVax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSF1R Kinase Inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrevia, Cyrin CLARIS, CYT007TNFQb, CYT013IL1bQb, CYT015IL17Qb, CYT020TNFQb, CYT107, CYT387, CYT99007, cytokine inhibitors, Cytopan, Cytoreg, CZC24832, D1927, D9421C, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declophen, Decopen, Decorex, Decorten, Dedema, Dedron, Deexa, Defcort, De-flam, Deflamat, Deflan, Deflanil, Deflaren, Deflaz, deflazacort, Defnac, Defnalone, Defnil, Defosalic, Defsure, Defza, Dehydrocortison, Dekort, Delagil, delcasertib, delmitide, Delphicort, Deltacorsolone, Deltacortril, Deltafluorene, Deltasolone, Deltasone, Deltastab, Deltonin, Demarin, Demisone, Denebola, denileukin diftitox, denosumab, Denzo, Depocortin, Depo-medrol, Depomethotrexate, Depopred, Deposet, Depyrin, Derinase, Dermot, Dermolar, Dermonate, Dermosone, Dersone, Desketo, desonide, desoxycorticosterone acetate, Deswon, Dexa, Dexabene, Dexacip, Dexacort, Dexacortisone, Dexacotisil, Dexadic, Dexadrin, Dexadron, Dexafar, Dexahil, Dexalab, Dexalaf, Dexalet, Dexalgen, Dexallion, Dexalocal, Dexalone, Dexa-M, Dexamecortin, Dexamed, Dexamedis, Dexameral, Dexameta, Dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexony, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Diclogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Dolaren, Dolchis, Dolex, Dolflam, Dolfre, Dolgit, Dolmax, Dolmina, Dolo Ketazon, Dolobest, Dolobid, Doloc, Dolocam, Dolocartigen, Doloflt, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, ECO286, EC0565, EC0746, Ecax, *echinacea purpurea* extract, EC-Naprosyn, Econac, Ecosprin 300, Ecosprin 300, Ecridoxan, eculizumab, Edecam, efalizumab, Efcortesol, Effigel, Eflagen, Efridol, EGFR Antibody, EGS21, eIF5A1 siRNA, Ekarzin, elafin, Eldoflam, Elidel, Eliflam, Elisone, Elmes, Elmetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor antibody, epidermal growth factor receptor 2 antibody, Epidixone, Epidron, Epiklin, EPPA1, epratuzumab, EquiO, Erac, Erazon, ERB041, ERB196, Erdon, EryDex, *escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra Feverlet, Extrapan, Extrauma, Exudase, F16, F991, Falcam, Falcol, Falzy, Farbovil, Farcomethacin, Farnerate, Farnezone, Farnezone, Farotrin, fas antibody, Fastflam, FasTRACK, Fastum, Fauldmetro, FcgammaRlA antibody, FE301, Febrofen, Febrofld, felbinac, Feldene, Feldex, Feloran, Felxicam, Fenac, Fenacop, Fenadol, Fenaflan, Fenamic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flanzen, Flaren, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Flurometholone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-I.V., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquin, Genotropin, Genz29155, Gerbin, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Hanall Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemner, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF1020, HFT-401, hG-CSFR ED Fc, Hiberna, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hyaron, Hycocin, Hycort, Hy-Cortisone, hydrocortisone, hydrocortisone acetate, hydrocortisone butyrate, hydrocortisone hemisuccinate, hydrocortisone sodium phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ, Hysonate, HZN602, I.M.75, IAP Inhibitors, Ibalgin, Ibalgin, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, Ibuscent, Ibusoft, Ibusuki Penjeong, Ibususpen, Ibutard, Ibutop, Ibutop, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hy1, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, ILV095, Imaxetil, IMD0560, IMD2560, Imesel Plus, Iminoral, Immodin, IMMU103, IMMU106, Immucept, Immufine, Immunex Syrup, immunoglobulin, immunoglobulin G, Immunoprin, ImmunoRel, Immurin, IMO8400, IMP731 antibody, Implanta, Imunocell, Imuran, Imurek, Imusafe, Imusporin, Imutrex, IN0701, Inal, INCB039110, INCB18424, INCB28050, INCB3284, INCB3344, Indexon, Indic, Indo, Indo-A, Indobid, Indo-Bros, Indocaf, Indocarsil, Indocid, Indocin, Indomehotpas, Indomen, Indomet, Indometacin, indomethacin, Indomethasone, Indometin, Indomin, Indopal, Indoron, Indotroxin, INDUS830, INDUS83030, Infladase, Inflamac, Inflammasome inhibitor, Inflavis, Inflaxen, Inflectra, infliximab, Ingalipt, Inicox dp, Inmecin, Inmunoartro, Innamit, InnoD06006, INO7997, Inocin, Inoten, Inovan, Inpra, Inside Pap, Insider-P, Instacyl, Instracool, Intafenac, Intaflam, Inteban, Inteban Spansule, integrin, alpha 1 antibody, integrin, alpha 2 antibody, Intenurse, interferon alfa, interferon beta-1a, interferon gamma, interferon gamma antibody, Interking, interleukin 1 Hy1, interleukin 1 antibody, interleukin 1 receptor antibody, interleukin 1, beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, lomab B, IOR-T3, IP751, IPH2201, IPH2301, IPH24, IPH33, IPI145, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, IVIG-SN, IWOOL Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofen, Ketofen, Ketolgan, Ketonal, Ketoplus Kata Plasma, ketoprofen, Ketores, Ketorin, ketorolac, ketorolac tromethamine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 Inhibitor, Klofen-L, Klotaren, KLS-40or, KLS-40ra, KM277, Knavon, Kodolo orabase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv1.3 Blocker, Kv1.3 4SC, Kv1.3 inhibitor, KVK702, Kynol, L156602, Labizone, Labohydro, Labopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LentiRA, LEO15520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LJP1207, LJP920, Lobafen, Lobu, Locafluo, Localyn, Locaseptil-Neo, Locpren, Lodine, Lodotra, Lofedic, Loflam, Lofnac, Lolcam, Lonac, lonazolac calcium, Loprofen, Loracort, Lorcam, Lorfenamin, Lorinden Lotio, Lorncrat, lornoxicam, Lorox, losmapimod, loteprednol etabonate, Loteprednol, Lotirac, Low Molecular *Ganoderma Lucidum* Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozyme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, MapKap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxy12, Maxy30, MAXY4, Maxy735, Maxy740, Mayfenamic, MB 11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MEDI552, MEDI571, Medicox, Medifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melurjin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, Methaderm, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methylprednisolone, Methysol, Metindol, Metoart, Metoject, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHC class II beta chain peptide, Micar, Miclofen, Miclofenac, Micofenolato Mofetil, Micosone, Microdase, microRNA 181 a-2 oligonucleotide, MIF Inhibitors, MIFQb, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, MISTB04, Mitilor, mizoribine, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 100, Momesone, Momesun, Mometamed, mometasone, mometasone furoate, Monimate, monosodium alpha-luminol, Mopik, MOR103, MOR104, MOR105, MOR208 antibody, MORAb022, Moricam, morniflumate, Mosuolit, Motoral, Movaxin, Mover, Movex, Movix, Movoxicam, Mox Forte, Moxen, moxifloxacin hydrochloride, Mozobil, MP, MP0210, MP0270, MP1000, MP1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase, muramidase hydrochloride, muromonab-CD3, Muslax, Muspinil, Mutaze, Muvera, MX68, Mycept, Mycocell, Mycocept, Mycofenolatmofetil Actavis, Mycofet, Mycofit, Mycolate, Mycoldosa, Mycomun, Myconol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Naklofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Naprox, naproxen, naproxen sodium, Naproxin, Naprozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, Newfenstop, NewGam, Newmafen, Newmatal, Newsicam, NEX1285, sFcRIIB, Nextomab, NF-kappaB Inhibitor, NF-kB inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nimnat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNC014100000100, NNC051869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NPI1342, NPI1387, NPI1390, NPRCS1, NPRCS2, NPRCS3, NPRCS4, NPRCSS, NPRCS6, NPS3, NPS4, nPT-ery, NU3450, nuclear factor NF-kappa-B p65 subunit oligonucleotide, Nucort, Nulojix, Numed-Plus, Nurokind Ortho, Nusone-H, Nutrikemia, Nuvion, NV07alpha, NX001, Nyclobate, Nyox, Nysa, Obarcort, OC002417, OC2286, ocaratuzumab, OCTSG815, Oedemase, Oedemase-D, ofatumumab, Ofgyl-O, Ofvista, OHR118, OKi, Okifen, Oksamen, Olai, olokizumab, Omeprose E, Omnacortil, Omneed, Omniclor, Omnigel, Omniwel, onercept, ON04057, ONS1210, ONS1220, Ontac Plus, Ontak, ONX0914, OPC6535, opebacan, OPN101, OPN201, OPN302, OPN305, OPN401, oprelvekin, OPT66, Optifer, Optiflur, OptiMIRA, Orabase Hca, Oradexon, Oraflex, OralFenac, Oralog, Oralpred, Ora-sed, Orasone, orBec, Orbone forte, Orcl, ORE10002, ORE10002, Orencia, Org214007, Org217993, Org219517, Org223119, Org37663, Org39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II, Orthomac, Ortho-Plus, Ortinims, Ortofen, Orudis, Oruvail, OS2, Oscart, Osmetone, Ospain, Ossilife, Ostelox, Osteluc, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, Oxyphenbutazone, ozoralizumab, P13 peptide, P1639, P21, P2X7 Antagonists, p38 Alpha Inhibitor, p38 Antagonist, p38 MAP kinase inhibitor, p38alpha MAP Kinase Inhibitor, P7 peptide, P7170, P979, PA401, PA517, Pabi-dexamethasone, PAC, PAC10649, paclitaxel, Painoxam, Paldon, Palima, pamapimod, Pamatase, Panafcort, Panafcortelone, Panewin, PanGraf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaject Busulfan, pateclizumab, Paxceed, PBI0032, PBI1101, PBI1308, PBI1393, PBI1607, PBI1737, PBI2856, PBI4419, PBI4419, P-Cam, PCI31523, PCI32765, PCI34051, PCI45261, PCI45292, PCI45308, PD360324, PD360324, PDA001, PDE4 inhibitor, PDE-IV Inhibitor, PDL241 antibody, PDL252, Pediapred, Pefree, pegacaristim, Peganix, Peg-Interleukin 12, pegsunercept, Pegsunercept, PEGylated arginine deiminase, peldesine, pelubiprofen, Penacle, penicillamine, Penostop, Pentalgin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PHS, PH797804, PHA408, Pharmaniaga Mefenamic acid, Pharmaniaga Meloxicam, Pheldin, Phenocept, phenylbutazone, PHY702, PI3K delta inhibitor, PI3K Gamma/Delta Inhibitor, PI3K Inhibitor, Picalm, pidotimod, piketoprofen, Pilelife, Pilopil, Pilovate, pimecrolimus, Pipethanen, Piractam, Pirexyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygam S/D, Polyphlogin, Poncif, Ponstan, Ponstil Forte, Porine-A Neoral, Potaba, potassium aminobenzoate, Potencort, Povidone, povidone iodine, pralnacasan, Prandin, Prebel, Precodil, Precortisyl Forte, Precortyl, Predfoam, Predicort, Predicorten, Predilab, Predilone, Predmetil, Predmix, Predna, Prednesol, Predni, prednicarbate, Prednicort, Prednidib, Prednifarma, Prednilasca, prednisolone, prednisolone acetate, prednisolone sodium phosphate, prednisolone sodium succinate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Proponol, propyl nicotinate, Prostaloc, Prostapol, Protacin, Protase, Protease Inhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Pulminiq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix Isatidis, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TIMP-2, recombinant human alkaline Phosphatase, recombinant Interferon Gamma, Recominant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade, Remsima, Remsima, Remsima, ReN1869, Renacept, Renfor, Renodapt, Renodapt-S, Renta, Reosan, Repare-AR, Reparilexin, reparixin, Repertaxin, Repisprin, Resochin, Resol, resolvin E1, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin, Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rituxan, rituximab, RNS60, RO1138452, Ro313948, RO3244794, RO5310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, ROR Gamma T Antagonist, ROR gamma t inverse agonists, Rosecin, rosiglitazone, Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ445380, RX10001, Rycloser MR, Rydol, S1P Receptor Agonists, S1P Receptor Modulators, S1P1 Agonist, S1P1 receptor agonist, 52474, S3013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SBI087, SC080036, SC12267, SC409, Scaflam, SCD ketoprofen, SCI0323, SCI0469, SD-15, SD281, SDP051 antibody, Sd-rxRNA, secukinumab, Sedase, Sedilax, Sefdene, Seizyme, SEL113, Seladin, Selecox, selectin P ligand antibody, Glucocorticoid Receptor Agonist, Selectofen, Selektine, SelK1 antibody, Seloxx, Selspot, Selzen, Selzenta, Selzentry, semapimod, semapimod hydrochloride, semparatide, Semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shincort, Shiosol, ShK186, Shuanghuangxiaoyan, SI615, SI636, Sigmasporin, Sigmasporin, SIM916, Simpone, Simulect, Sinacort, Sinalgia, Sinapol, Sinatrol, Sinsia, siponimod, Sirolim, sirolimus, Siropan, Sirota, Sirova, sirukumab, Sistal Forte, SKF105685, SKF105809, SKF106615, SKF86002, Skinalar, Skynim, Skytrip, SLAM family member 7 antibody, Slo-indo, SM101, SM201 antibody, SM401, SMAD family member 7 oligonucleotide, SMART Anti-IL-12 Antibody, SMP114, SNO030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepcizumab, Sonexa, Sonim, Sonim P, Soonil, Soral, Sorenil, sotrastaurin acetate, SP-10, SP600125, Spanidin, SP-Cortil, SPD550, Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSSO7 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Steno, Sterisone, Steron, stichodactyla helianthus peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, sulfasalazine, Sulfovit, Sulidac, Sulide, sulindac, Sulindex, Sulinton, Sulphafine, Sumilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFcS, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapainbeta, Tapoein, Tarenac, tarenflurbil, Tarimus, Tarproxen, Tauxib, Tazomust, TBR652, TC5619, T-cell, immune regulator 1, ATPase, H+ transporting, lysosomal V0 subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenil, Therafectin, Therapyace, thiarabine, Thiazolopyrimidines, thioctic acid, thiotepa, THR090717, THR0921, Threenofen, Thrombate III, Thymic peptide, Thymodepressin, Thymogam, Thymoglobulin, Thymoglobuline, Thymoject thymic peptides, thymomodulin, thymopentin, thymopolypetides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, ToleriMab, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Troycort, TRX1 antibody, TRX4, Trymoto, Trymoto-A, TT301, TT302, TT32, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member 1B antibody, tumor necrosis factor receptor superfamily1B oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767, Uremol-HC, Urigon, U-Ritis, ustekinumab, V85546, Valcib, Valcox, valdecoxib, Valdez, Valdixx, Valdy, Valentac, Valoxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, VenimmunN, Venoforte, Venoglobulin-IH, Venozel, Veral, Verax, vercirnon, vero-Dexamethasone, Vero-Kladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab, Votan-SR, VR909, VRA002, VRP1008, VRS826, VRS826, VT111, VT214, VT224, VT310, VT346, VT362, VTX763, Vurdon, VX30 antibody, VX467, VX5, VX509, VX702, VX740, VX745, VX745, VX850, W54011, Walacort, Walix, WC3027, Wilgraf, Winflam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XPro1595, XtendTNF, XTol1, Xtra, Xylex-H, Xynofen SR, Yang Shu-IVIG, YHB14112, YM974, Youfeline, Youfenac, Yuma, Yumerol, Yuroben, YY piroxicam, Z104657A, Zacy, Zaltokin, zaltoprofen, Zap70 Inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte. In addition, the anti-inflammatory drugs, as listed above, may be combined with one or more agents listed above or herein or with other agents known in the art.

In some embodiments, a drug that reduces, inhibits, prevents and/or ameliorates inflammation, for example, one of the drugs provided above, is delivered to the suprachoroidal space of the eye using the kits, microneedle devices, and methods disclosed herein, and is used to treat, prevent and/or ameliorate a disease or disorder selected from arthritis, degenerative arthritis, psoriatic arthritis, arthritic disorders, arthritic pain, arthrosis, autoimmune arthritis, autoimmune diseases, autoimmune disorders, axial spondyloarthritis, chronic prosthetic joint infection, collagen induced arthritis, osteoarthritis, rheumatoid arthritis, senile arthritis, seronegative oligoarthritis of the knee, allergic and autoimmune inflammatory diseases, inflammatory diseases, inflammatory disorders, collagen diseases, discoid Lupus Erythematosus, immune deficiencies, immune diseases, immune disorders, immunodeficiency diseases, immunodeficiency disorders, immunoglobulin (IgG2) deficiency, immunoglobulin deficiency, Inflammation, Lambert-Eaton myasthenia syndrome, polymyositis, dermatomyositis, polyneuritis, post-operative ocular inflammation, polychondritis, sporadic inclusion body myositis, Systemic Lupus Erythematosus, T cell deficiency, TNF-receptor associated periodic syndrome, tropical spastic paraparesis, Wegener Granulomatosis, X-linked severe combined immunodeficiency disease, Behcet's disease, Crohn's disease, Crohn's Fistula, cutaneous Lupus Erythematosus, acute inflammation, acute inflammatory edema, adrenocortical insufficiency, cerebral inflammation, chronic lung inflammation, corticoid-responsive inflammatory skin disorders, cutaneous inflammation, dermal inflammation, dry skin inflammatory disease, ear edema, ear inflammation, glossitis, inflammatory bowel disease, inflammatory degenerative disease, inflammatory disorders of the eye and/or ear, inflammatory lesions in fungal infections, inflammatory lesions, inflammatory pain, inflammatory skin diseases or disorders, mouth and gum inflammation, mouth and throat inflammation, musculoskeletal disorders, otitis, pelvic inflammatory disease, perianal inflammation, post operative inflammation, pulmonary inflammation, rectal inflammation, refractory idiopathic inflammatory myopathies, seborrhoeic dermatitis, swelling, aphthous ulcerations, chronic polyarthritis, juvenile rheumatoid arthritis, rheumatic diseases, Sjogren's syndrome, opthalmic for Sjogren's syndrome, transplant rejection, acute allograft rejection, chronic graft rejection, graft versus host disease, humoral rejection in heart transplantation, humoral rejection in kidney transplantation, organ rejection in renal transplantation, solid organ transplant rejection, bronchiolitis obliterans after lung transplantation, rejection of bone marrow transplant, chronic lung transplant rejection, Corneal graft rejection, delayed graft function in kidney transplantation, heart transplant rejection, Homotransplantation rejection, immune rejection of hESC-derived therapeutic grafts, kidney transplant rejection, liver transplant rejection, lung transplant rejection, organ rejection, pancreatic islet transplantation rejection in type I diabetes, renal transplant rejection and xenograft rejection.

In some embodiments, the drug delivered to the suprachoroidal space using the kits, microneedle devices, and methods disclosed herein treats, prevents, and/or ameliorates macular degeneration (e.g., age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, Subfoveal wet Age-Related macular degeneration, and Vitreomacular Adhesion (VMA) associated with Neovascular Age Related macular degeneration). Examples of drugs that treat, prevent and/or ameliorate macular degeneration that can be used in conjunction with the devices and methods described herein include, but are not limited to: A0003, A36 peptide, AAV2-sFLT01, ACE041, ACU02, ACU3223, ACU4429, AdPEDF, aflibercept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC1905, ARC1905 with Lucentis, ATG3, ATP-binding cassette, sub-family A, member 4 gene, ATXS10, Avastin with Visudyne, AVT101, AVT2, bertilimumab, bevacizumab with verteporfin, bevasiranib sodium, bevasiranib sodium; with ranibizumab, brimonidine tartrate, BVA301, canakinumab, Cand5, Cand5 with Lucentis, CERE140, ciliary neurotrophic factor, CLT009, CNT02476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD4514S, fenretinide, fluocinolone acetonide, fluocinolone acetonide with ranibizumab, fms-related tyrosine kinase 1 oligonucleotide, fms-related tyrosine kinase 1 oligonucleotide with kinase insert domain receptor 169, fosbretabulin tromethamine, Gamunex, GEM220, GS101, GSK933776, HC31496, Human n-CoDeR, HYB676, IBI-20089 with Lucentis, iCo-008, Iconl, I-Gold, Ilaris, Iluvien, Iluvien with Lucentis, immunoglobulins, integrin alpha5betAlimmunoglobulin fragments, Integrin inhibitor, IRIS Lutein, I-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with myrtillus extract, Lutein with zeaxanthin, M200, M200 with Lucentis, Macugen, MC1101, MCT355, mecamylamine, Microplasmin, motexafin lutetium, MP0112, NADPH oxidase inhibitors, Neoretna, neurotrophin 4 gene, Nova21012, Nova21013, NT501, NT503, Nutri-Stulln, ocriplasmin, OcuXan, Oftan Macula, Optrin, ORA102 with Avastin, P144, P17, Palomid 529, PAN90806, Panzem, Panzem, PARP Inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005, PMX53, POT4, PRS055, PTK787, ranibizumab, ranibizumab with triamcinolone acetonide, ranibizumabwith verteporfin, ranibizumab with volociximab, RD27, Rescula, Retaane, retinal pigment epithelial cells, RetinoStat, RG7417, RN6G, RT101, RTU007, SB267268, serpin peptidase inhibitor, clade F, member 1 gene, shark cartilage extract, Shef1, SIR1046, SIR1076, Sirna027, sirolimus, SMTD004, Snelvit, SOD Mimetics, Soliris, sonepcizumab, squalamine lactate, ST602, StarGen, T2TrpRS, TA106, talaporfin sodium, Tauroursodeoxycholic acid, TG100801, TM, TLCx99, TRC093, TRC105, triamcinolone acetonide with verteporfin, Trivastal Retard, TT30, Ursa, ursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF Inhibitor, verteporfin, Visudyne, Visudyne with Lucentis and dexamethasone, Visudyne with triamcinolone acetonide, Vivis, volociximab, Votrient, XV615, zeaxanthin, ZFP TF, zinc-monocysteine and Zybrestat. In one embodiment, one or more of the macular degeneration treating drugs described above is combined with one or more agents listed above or herein or with other agents known in the art.

In one embodiment, the kits, methods, and devices provided herein are used to deliver triamcinolone or triamcinolone acetonide to the suprachoroidal space of an eye of a patient in need thereof. In a further embodiment, the triamcinolone or triamcinolone acetonide is delivered for the treatment of sympathetic ophthalmia, temporal arteritis, uveitis and/or ocular inflammatory conditions. In one embodiment, triamcinolone or triamcinolone acetonide is delivered to the suprachoroidal space of the eye in a patient in need of treatment of sympathetic opthalmia with the methods and devices described herein. In another embodiment, triamcinolone or triamcinolone acetonide is delivered to the suprachoroidal space of the eye in a patient in need of treatment of temporal arteritis with the methods and devices described herein. In yet another embodiment, triamcinolone or triamcinolone acetonide is delivered to the suprachoroidalspace of the eye in a patient in need of treatment of uveitis, with the methods and devices described herein. In another embodiment, triamcinolone or triamcinolone acetonide is delivered to the suprachoroidal space of the eye in a patient in need of treatment of one or more ocular inflammatory conditions, with the methods and devices described herein.

The triamcinolone composition provided herein, in one embodiment, is a suspension comprising microparticles or nanoparticles of triamcinolone or triamcinolone acetonide. The microparticles, in one embodiment, have a D50 of about 3 μm or less. In a further embodiment, the D50 is about 2 μm. In another embodiment, the D50 is about 2 μm or less. In even another embodiment, the D50 is about 1000 nm or less. The microparticles, in one embodiment, have a D99 of about 10 μm or less. In another embodiment, the D99 is about 10 μm. In another embodiment, the D99 is less than about 10 μm or less than about 9 μm or less.

In one embodiment, the triamcinolone composition comprises triamcinolone microparticles. In a further embodiment, the composition comprises polysorbate 80. In another embodiment, the triamcinolone composition comprises one or more of CaCl2, MgCl2, sodium acetate and sodium citrate. In one embodiment, the composition comprises polysorbate 80 at a w/v % of 0.02% or about 0.02%, 0.015% or about 0.015%.

In certain embodiments, the drug delivered to ocular tissues using the kits, microneedle devices, and methods disclosed herein treats, prevents, and/or ameliorates fibrosis (e.g. myelofibrosis, fibrosis in diabetic nephropathy, cystic fibrosis, scarring, and skin fibrosis).

In some embodiments, a drug that treats, prevents and/or ameliorates fibrosis is used in conjunction with the kits, devices, and methods described herein, and is delivered to the suprachoroidal space of the eye. In a further embodiment, the drug is Actimmune with Pirfenidone, ACUHTR028, AlphaVBeta5, aminobenzoate potassium, amyloid P, ANG1122, ANG1170, ANG3062, ANG3281, ANG3298, ANG4011, Anti-CTGF RNAi, Aplidin, astragalus membranaceus extract with salvia and schisandra chinensis, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB119, JKB121, JKB122, KRX168, LPAlreceptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RXI109, secretin, STX100, TGF-beta Inhibitor, transforming growth factor, beta receptor 2 oligonucleotide, VA999260 or XV615. In one embodiment, one or more of the fibrosis treating drugs described above is combined with one or more agents listed above or herein or with other agents known in the art.

In some embodiments, a drug that treats, prevents and/or ameliorates diabetic macular edema is used in conjunction with the kits, devices, and methods described herein, and is delivered to the suprachoroidal space of the eye. In a further embodiment, the drug is AKB9778, bevasiranib sodium, Candy5, choline fenofibrate, Cortiject, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0503 or Tri-Lipix. In one embodiment, one or more of the diabetic macular edema treating drugs described above is combined with one or more agents listed above or herein or with other agents known in the art.

In some embodiments, a drug that treats, prevents and/or ameliorates macular edema is used in conjunction with the kits, devices, and methods described herein, and is delivered to the suprachoroidal space of the eye. In a further embodiment, the drug is denufosol tetrasodium, dexamethasone, ecallantide, pegaptanib sodium, ranibizumab or triamcinolone. In addition, the drugs delivered to ocular tissues using the microneedle devices and methods disclosed herein which treat, prevent, and/or ameliorate macular edema, as listed above, may be combined with one or more agents listed above or herein or with other agents known in the art.

In some embodiments, a drug that treats, prevents and/or ameliorates ocular hypertension is used in conjunction with the kits, devices, and methods described herein and is delivered to the suprachoroidal space of the eye. In a further embodiment, the drug is 2-MeS-beta gamma-CC12-ATP, Aceta Diazol, acetazolamide, Aristomol, Arteoptic, AZD4017, Betalmic, betaxolol hydrochloride, Betimol, Betoptic S, Brimodin, Brimonal, brimonidine, brimonidine tartrate, Brinidin, Calte, carteolol hydrochloride, Cosopt, CS088, DE092, DE104, DE111, dorzolamide, dorzolamide hydrochloride, Dorzolamide hydrochloride with Timolol maleate, Droptimol, Fortinol, Glaumol, Hypadil, Ismotic, isopropyl unoprostone, isosorbide, Latalux, latanoprost, Latanoprost with Timolol maleate, levobunolol hydrochloride, Lotensin, Mannigen, mannitol, metipranolol, mifepristone, Mikelan, Minims Metipranolol, Mirol, nipradilol, Nor Tenz, Ocupress, olmesartan, Ophtalol, pilocarpine nitrate, Piobaj, Rescula, RU486, Rysmon TG, SAD448, Saflutan, Shemol, Taflotan, tafluprost, tafluprost with timolol, Thiaboot, Timocomod, timolol, Timolol Actavis, timolol hemihydrate, timolol maleate, Travast, travoprost, Unilat, Xalacom, Xalatan or Zomilol. In addition, the drugs delivered to ocular tissues using the microneedle devices and methods disclosed herein which treat, prevent, and/or ameliorate ocular hypertension, as listed above, may be combined with one or more agents listed above or herein or with other agents known in the art.

In some embodiments, a drug that inhibits angiogenesis is used in conjunction with the kits, devices, and methods described herein and is delivered to the suprachoroidal space of the eye. In some embodiments, the angiogenesis inhibitor is an antagonist of a member of the platelet derived growth factor (PDGF) family, for example, a drug that inhibits, reduces or modulates the signaling and/or activity of PDGF-receptors (PDGFR). For example, the PDGF antagonist delivered to the suprachoroidal space for the treatment of a choroidal malady, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

In certain embodiments one or more drugs may be delivered to ocular tissues and/or into the suprachoroidal space via the systems and devices described herein. Delivery of one or more drugs into the suprachoroida lspace using the microneedle device described herein may be accomplished by using one or more microneedles. In addition, combinations of one of more drugs may be delivered to the suprachoroidal space using the microneedle device described herein in combination with delivery of one or more drugs via intravitreal (IVT) administration (e.g., intravitreal injection, intravitreal implant or eye drops). Methods of IVT administration are well known in the art. Examples of drugs that can be administered via IVT include, but are not limited to: A0003, A0006, Acedolone, AdPEDF, aflibercept, AG13958, aganirsen, AGN208397, AKB9778, AL78898A, amyloid P, Angiogenesis Inhibitor Gene Therapy, ARC1905, Aurocort, bevasiranib sodium, brimonidine, Brimonidine, brimonidine tartrate, bromfenac sodium, Candy5, CERE140, Ciganclor, CLT001, CLT003, CLT004, CLT005, complement component 5 aptamer (pegylated), complement factor D antibody, Cortiject, c-raf 2-methoxyethyl phosphorothioate oligonucleotide, cyclosporine, triamcinolone, DE109, denufosol tetrasodium, dexamethasone, dexamethasone phosphate, disitertide, DNA damage inducible transcript 4 oligonucleotide, E10030, ecallantide, EG3306, Eos013, ESBA1008, ESBA105, Eylea, FCFD4514S, fluocinolone acetonide, fms-related tyrosine kinase 1 oligonucleotide, fomivirsen sodium, fosbretabulin tromethamine, FOV2301, FOV2501, ganciclovir, ganciclovir sodium, GS101, GS156, hyaluronidase, IBI20089, iCo007, Iluvien, INS37217, Isonep, JSM6427, Kalbitor, KH902, lerdelimumab, LFG316, Lucentis, M200, Macugen, Makyueido, Microplasmin, MK0140, MP0112, NCX434, neurotrophin 4 gene, OC10X, ocriplasmin, ORA102, Ozurdex, P144, P17, Palomid 529, pazopanib hydrochloride, pegaptanib sodium, Plasma Kallikrein Inhibitors, platelet-derived growth factor beta polypeptide aptamer (pegylated), POT4, PRM167, PRS055, QPI1007, ranibizumab, resveratrol, Retilone, retinal pigment epithelium-specific protein 65 kDa gene, Retisert, rod derived cone viability factor, RPE65 Gene Therapy, RPGR Gene Therapy, RTP801, Sd-rxRNA, serpin peptidase inhibitor clade F member 1 gene, Sirna027, sirolimus, sonepcizumab, SRT501, STP601, TG100948, Trabio, triamcinolone, triamcinolone acetonide, Trivaris, tumor necrosis factor antibody, VEGF/rGel-Op, verteporfin, Visudyne, Vitrase, Vitrasert, Vitravene, Vitreals, volociximab, Votrient, XG102, Xibrom, XV615, and Zybrestat. Accordingly, the methods of the present invention include administrating via IVT one or more of the drugs listed above in combination with one or more drugs disclosed herein administered into the suprachoroidal space using the microneedle device described herein.

In some embodiments, the drug is formulated for storage and delivery via the kits, microneedle devices, and methods described herein. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. In one embodiment, the excipient may include or consist of water or saline.

In some embodiments, the fluid drug formulation includes microparticles or nanoparticles, each of which can include at least one drug. Desirably, the microparticles or nanoparticles provide for the controlled release of drug into the ocular tissue. As used herein, the term "microparticle" encompasses microspheres, microcapsules, microparticles, and beads, having a number average diameter of 1 to 100 μm, most preferably 1 to 25 μm. The term "nanoparticles" are particles having a number average diameter of 1 to 1000 nm. Microparticles may or may not be spherical in shape. "Microcapsules" are defined as microparticles having an outer shell surrounding a core of another material. The core can be liquid, gel, solid, gas, or a combination thereof. In one case, the microcapsule may be a "microbubble" having an outer shell surrounding a core of gas, wherein the drug is disposed on the surface of the outer shell, in the outer shell itself, or in the core. Microbubbles may respond to acoustic vibrations as known in the art for diagnosis and/or can be used to burst the microbubble to release its payload at/into a select ocular tissue site. "Microspheres" can be solid spheres, can be porous and include a sponge-like or honeycomb structure formed by pores or voids in a matrix material or shell, or can include multiple discrete voids in a matrix material or shell. The microparticle or nanoparticles may further include a matrix material. The shell or matrix material may be a polymer, amino acid, saccharide, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc., which are known in the art to control the kinetics of drug release from particles.

In one embodiment, the fluid drug formulation further includes an agent effective to degrade collagen or GAG fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of the drug. The enzyme and drug are administered at the same site.

In another embodiment, the drug formulation is one that undergoes a phase change upon administration. For instance, a liquid drug formulation may be injected through hollow microneedles into the suprachoroidal space, where it then gels and the drug diffuses out from the gel for controlled release.

While the embodiments and methods herein describe delivering a medicament to a target tissue, the embodiments described herein can be configured to facilitate a biopsy procedure and/or removal of a substance from a target location.

While the embodiments have been described above in use on ocular tissue, in some instances, the embodiments and methods described herein can be used on any other suitable bodily tissue. For example, in some instances, the use of an adjustable length needle can be beneficial in conjunction with standard phlebotomy techniques during drug infusion and/or blood draw from a vein. Thus, while the embodiments and methods are specifically described above in use on ocular tissue, it should be understood that the embodiments and methods have been presented by way of example only, and not limitation Although various embodiments have been described as having particular features and/or combinations of components, other embodiments are possible having a combination of any features and/or components from any of embodiments where appropriate. For example, in some embodiments, the needle assembly 3200 can include a housing having an opening similar to the housing 4210 (having the opening 4232).

What is claimed is:

1. A method, comprising: inserting a distal tip of a puncture member of a medical injector into a first region of a target tissue, the medical injector including a medicament container, a hub, an adjustment member, and the puncture member fixedly coupled to and extending distally from the adjustment member, the distal tip of the puncture member extending from a distal end surface of the hub by a first distance before and during the inserting, the adjustment member disposed within an inner volume of the hub such that the inner volume is separated into a first chamber and a second chamber fluidically isolated from the first chamber by the adjustment member, the first chamber being in fluid communication with the medicament container, the adjustment member configured to transition within the inner volume between a first configuration and a second configuration; and conveying a substance from the medicament container into the first chamber defined within the hub when the distal tip is within the first region of the target tissue to produce a pressure within the first chamber, the pressure causing the adjustment member to transition to the second configuration, thereby causing the distal tip of the puncture member to move within the first region of the target tissue such that the distal tip of the puncture member extends from the distal end surface of the hub by a second distance greater than the first distance and into a second region of the target tissue, the pressure insufficient to produce a flow of the substance from the first chamber through the puncture member when the distal tip of the puncture member is within the first region of the target tissue, the pressure producing the flow of the substance from the first chamber through the puncture member when the distal tip of the puncture member is within the second region of the target tissue.

2. The method of claim 1, wherein: the first region is an upper portion of a sclera of an eye; and the second region includes at least one of a suprachoroidal space, a lower portion of the sclera of the eye, a choroid of the eye, a subretinal space of the eye, or a retina of the eye.

3. The method of claim 1, wherein:
the first region of the target tissue has a first density; and
the second region of the target tissue has a second density, the second density being less than the first density.

4. The method of claim 1, wherein the substance includes at least one of a VEGF, a VEGF inhibitor, a PDGFR inhibitor, or a combination of any of the VEGF, the VEGF inhibitor, and the PDGFR inhibitor.

5. The method of claim 1, wherein the conveying the substance includes manually exerting a force of less than about 6N on an actuation rod to move a distal end portion of the actuation rod within the medicament container.

6. The method of claim 1, wherein, the pressure is a first pressure; and the first pressure within the first chamber decreases to a second pressure in response to the flow of the substance from the first chamber through the puncture member when the distal tip of the puncture member is within the second region of the target tissue, the second pressure insufficient to move the puncture member relative to the distal end surface of the hub.

7. The method of claim 1, wherein the hub is removably coupled to the medicament container.

8. The method of claim 1, further comprising: manipulating an actuation rod disposed within the medicament container to convey the substance from the medicament container into the first chamber and thereby produce the pressure within the first chamber, a distal end of the actuation rod terminating within the medicament container and proximal to the hub.

9. The method of claim 1, wherein the adjustment member includes an edge fixedly coupled to an inner surface of the hub, and an expandable portion configured to expand distally when the adjustment member is transitioned from the first configuration to the second configuration.

10. The method of claim 1, wherein the adjustment member includes an edge slidably coupled to an inner surface of the hub, the pressure in the first chamber causing the adjustment member to slide distally relative to the medicament container and the hub to increase the size of the first chamber and extend the puncture member distally relative to the medicament container and the hub.

11. The method of claim 1, wherein the conveying the substance includes exerting a force on an actuation rod to move a distal end portion of the actuation rod within the medicament container.

12. The method of claim 11, wherein the exerting the force includes manually exerting the force by manipulating a proximal end portion of the actuation rod.

13. The method of claim 1, wherein the inserting the distal tip of the puncture member includes: inserting the distal tip such that a centerline of the puncture member and a surface line tangential to a target surface of the first region of the target tissue defines an angle of entry of between about 75 degrees and about 105 degrees; and contacting the distal end surface of the hub with the target surface of the target tissue.

14. The method of claim 13, wherein the contacting includes deforming the target surface with the distal end surface of the hub.

15. A method, comprising: inserting a distal tip of a puncture member of a medical injector into a first region of a target tissue, the medical injector including a medicament container, a hub, an adjustment member, and the puncture member fixedly coupled to and extending distally from the adjustment member, the distal tip of the puncture member extending from a distal end surface of the hub before and during the inserting, the adjustment member disposed within an inner volume of the hub such that the inner volume is separated into a first chamber and a second chamber fluidically isolated from the first chamber by the adjustment member, the first chamber being in fluid communication with the medicament container, the adjustment member configured to transition within the inner volume between a first configuration. and a second configuration; and exerting a force on the medical injector to cause the adjustment member to transition to the second configuration, thereby causing the distal tip of the puncture member to move in a distal direction relative to the distal end surface of the hub from the first region of the target tissue to a second region of the target tissue, the force being insufficient to produce a flow of a substance from the first chamber defined at least in part within the hub through the puncture member when the distal tip of the puncture member is within the first region of the target tissue, the force being sufficient to cause the substance to flow through the puncture member when the distal tip of the puncture member is within the second region of the target tissue.

16. The method of claim 15, wherein a density of the first region is greater than a density of the second region.

17. The method of claim 15, wherein the exerting the force includes manually exerting the force, the force being than about 6N.

18. The method of claim 15, wherein a movement of a distal end portion of an actuation rod causes the substance to flow from the medicament container into the first chamber, the pressure urging the adjustment member to move the distal tip of the puncture member in the distal direction.

19. The method of claim 15, wherein the exerting the force includes exerting a force on an actuation rod to move a distal end portion of the actuation rod within the medicament container.

20. The method of claim 15, wherein: the first region is an upper portion of a sclera of an eye; and the second region includes at least one of a suprachoroidal space, a lower portion of the sclera of the eye, a choroid of the eye, a subretinal space of the eye, or a retina of the eye.

21. The method of claim 20, wherein the substance includes at least one of a VEGF, a VEGF inhibitor, a PDGFR inhibitor, or a combination of any of the VEGF, the VEGF inhibitor, and the PDGFR inhibitor.

* * * * *